US006423829B1

(12) United States Patent
Belt et al.

(10) Patent No.: US 6,423,829 B1
(45) Date of Patent: Jul. 23, 2002

(54) NITROBENZYLMERCAPTOPURINE-RIBOSIDE (NBMPR)-INSENSITIVE, EQUILIBRATIVE, NUCLEOSIDE TRANSPORT PROTEIN, NUCLEIC ACIDS ENCODING THE SAME AND METHODS OF USE

(75) Inventors: Judith A. Belt; Charles R. Crawford; Divyen H. Patel, all of Memphis, TN (US)

(73) Assignee: St. Jude Children's Research Hosital, Memphis, TN (US)

( * ) Notice: Subject to any disclaimer, the term of this patent is extended or adjusted under 35 U.S.C. 154(b) by 0 days.

(21) Appl. No.: 09/611,781

(22) Filed: Jul. 7, 2000

Related U.S. Application Data

(62) Division of application No. 09/058,389, filed on Apr. 9, 1998, now Pat. No. 6,130,065.
(60) Provisional application No. 60/043,659, filed on Apr. 11, 1997.

(51) Int. Cl.[7] .......................... C07K 14/00; C07H 21/04
(52) U.S. Cl. .......................... 530/350; 530/350; 514/2; 435/69.1; 435/69.7; 435/252.3; 435/325; 435/320.1; 435/366; 536/23.1; 536/24.33
(58) Field of Search .......................... 514/2; 530/350; 435/69.1, 69.7, 252.3, 325, 320.1, 366; 536/23.1, 24.33

(56) References Cited

FOREIGN PATENT DOCUMENTS

WO          98/29437        7/1998

OTHER PUBLICATIONS

Griffiths et al., Molecular Cloning and characterization of a nitrobenzylthioinosine–insensitive (ei) equilibrative nucleoside transporter from human placenta. Biochem. J. (1997) 328, 739–743.*
Gene Bank AF029358 (Jan. 7, 1998).*
New England Biolabs Catalog1996/1997, p. 111.
Belt, *Mol. Pharmacol.*, 24:479–484 (1983).
Belt et al. Advan. Enzyme Regul., 33:235–252 (1993).
Cass, in *Drug Transport in Antimicrobial Therapy and Anticancer Therapy* (N.H. Georgopapadakou, ed.(Marcel Dekker)), 403–451 (1995).
Crawford et al., 1998, J Biol Chem, 273:5288–93.
Dahlig–Harley et al., Biochem J. 200:295–305 (1981).
Fang et al., Biochem. J., 317:457–465 (1996).
Gati and Paterson, in *The red cell membrane: structure, function, and clinical implications*, P. Agre and J.C. Parker, ed., (New York: Marcel Decker), pp. 635–661 (1989).
Griffith et al., Biochim. Bioph. Acta 1286:153–181 (1996).
Griffiths et al., Nature Med. 3:89–93 (1997).
Hammond, *J. Pharmacol. Exp. Ther.*, 259:799–807 (1991).
Huang et al., *J. Biol. Chem.*, 268:20613–20620 (1993).
Huang et al., J. Biol. Chem., 269:17757–17760 (1994).
Jarvis, in *Adenosine Receptors*, D.M.F. Cooper and C. Londos, eds., (New York: Alan R. Liss, Inc.), pp. 113–123 (1988).
Jarvis, *Mol. Pharmacol.*, 30:659–665 (1986).
New England Biolabs Catalog, 1993/94, pp93–94.
Paterson et al., *Mol. Parmacol.*, 18:40–44 (1980).
Paterson and Cass, in *Membrane Transport of Antineoplastic Agents*, I.D. Goldman, ed., (New York: Pergamon Press), pp. 309–329 (1986).
Pajor et al., *J. Biol. Chem.*, 267:3557–3560 (1992).
Parkinson et al., *Gen. Pharmacol.* 25:1053–1058 (1994).
Plagemann et al., *Biochim. Biophys. Acta.*, 969:1–8 (1988).
Plagemann and Wohlheuter, *Biochim. Biophys. Acta.*, 773:39–52 (1984).
Plagemann and Wohlheuter, *Curr. Topics Membr. Trans.*, 14:225–330 (1980).
Ritzel et al. *Am. J. Physiol.* (1997).
Rongen et al., *J. Clin. Invest.* 95:658–668 (1995).
Ullman et al., J. Biol. Chem. 263:12391–12396 (1988).
Vijayalakshmi et al., *J. Biol. Chem.*, 263:19419–19423 (1988).
Williams et al., *Biochem. J.*, 264:223–231 (1991).
Williams et al. (1995) Biochem. Biophys. Res. Comm. 213:325–33.
Wu et al., *J. Biol. Chem.*, 267:8813–8818 (1992).
Yao et al., 1997, J Biol Chem, 272:28423–30.

\* cited by examiner

*Primary Examiner*—Karen Cochrane Carlson
*Assistant Examiner*—Chih Min Kam
(74) *Attorney, Agent, or Firm*—Klauber & Jackson; Shawn A. Hawkins

(57) ABSTRACT

An isolated NBMPR-insensitive equilibrative nucleoside transport protein (iENTP) and the nucleic acid encoding it is disclosed. The iENTP can be used in screening assays to identify both natural nucleoside perrneants and/or inhibitors and analogs thereof. In addition, transfected or transduced cell lines are disclosed which use the iENTP as the sole nucleoside transport protein. Methods of employing such cell lines for drug screening are also included. Furthermore methods of using hematopoietic stem cells transduced with an iENTP in a chemotherapy protocol is also described. In addition, methods of using these cells to selectively express a heterologous gene for gene therapy is disclosed.

3 Claims, 11 Drawing Sheets

```
hENT2  : MARGDAPRDSYHLVGISFFILGLGTLLPWNFFITAIPYF  :  39
hHNP36 : ---------------------------------------  :   -
hENT1  : MTTSHQPQDRYKAVWLIFFMLGLGTLLPWNFFMTATQYF  :  39
                      <=====TM1=======>

* * * *
hENT2  : QARLAGAGNSTARILSTNHTGPEDAFN------------  :  66
hHNP36 : ---------------------------------------  :   -
hENT1  : TNRLDMSQNVSLVTAELSKDAQASAAPAAPLPERNSLSA  :  78 hENT2  : -FNNWVTLLSQLPLLLFTLLNSFLYQCVPETVRILGSLL  : 104
hHNP36 : ---------------------------------------  :   -
hENT1  : IFNNVMTLCAMLPLLLFTYLNSFLHQRIPQSVRILGSLV  : 117
             <==========TM2==========>     <==== hENT2  : AILLLFALTAALVKVDMSPGPFFSITMASVCFINSFSAV  : 143
hHNP36 : --------------------------MASVCFINSFSAV  :  13
hENT1  : AILLVFLITAILVKVQLDALPFFVITMIKIVLINSFGAI  : 156
         TM3========>      <=======TM4======= hENT2  : LQGSLFGQLGTMPSTYSTLFLSGQGLAGIFAALAMLLSM  : 182
hHNP36 : LQGSLFGQLGTMPSTYSTLFLSGQGLAGIFAALAMLLSM  :  52
hENT1  : LQGSLFGLAGLLPASYTAPIMSGQGLAGFFASVAMICAI  : 195
               >              <=========TM5======== hENT2  : ASGVDAETSALGYFITPCVGILMSIVCYLSLPHLKFARY  : 221
hHNP36 : ASGVDAETSALGYFITPYVGILMSIVCYLSLPHLKFARY  :  91
hENT1  : ASGSELSESAFGYFITACAVIILTIICYLGLPRLEFYRY  : 234
         ===>        <=========TM6=======> hENT2  : YLANKSSQAQAQELETKAELLQSDENGIPSSPQKVALTL  : 260
hHNP36 : YLANKSSQAQAQELETKAELLQSDENGIPSSPQKVALTL  : 130
hENT1  : YQQLK--LEGPGEQETKLDLISKGEEPRAGK--------  : 263 hENT2  : DLDLEKEPESEPDEPQKPGKPSVFTVFQKIWLTALCLVL  : 299
hHNP36 : DLDLEKEPESEPDEPQKPGKPSVFTVFQKIWLTALCLVL  : 169
hENT1  : ----EESGVSVSNSQPTNESHSIKAILKNISVLAFSVCF  : 298
                                              <======
```

FIG. 2A

```
hENT2   : VFTVTLSVFPAITAMVTSS-TSPGKWSQFFNPICCFLLF : 337
hHNP36  : VFTVTLSVFPAITAMVTSS-TSPGKWSQFFNPICCFLLF : 207
hENT1   : IFTITIGMFPAVTVEVKSSIAGSSTWERYFIPVSCFLTF : 337
          ==TM7=======>              <=====TM8=== hENT2   : NIMDWLGRSLTSYFLWPDEDSRLLPLLVCLRFLFVPLFM : 376
hHNP36  : NIMDWLGRSLTSYFLWPDEDSRLLPLLVCLRFLFVPLFM : 246
hENT1   : NIFDWLGRSLTAVFMWPGKDSRWLPSLVLARLVFVPLIL : 376
          ====>                 <=======TM9====== hENT2   : LCHVPQRSRLPILFPQDAYFITFMLLFAVSNGYLVSLTM : 415
hHNP36  : LCHVPQRSRLPILFPQDAYFITFMLLFAVSNGYLVSLTM : 285
hENT1   : LCNIKPRRYLTVVFEHDAWFIFFMAAFAFSNGYLASLCM : 415
          =>           <======TM10=========> hENT2   : CLAPRQVLPHEREVAGALMTFFLALGLSCGASLSFLFKA : 454
hHNP36  : CLAPRQVLPHEREVAGALMTFFLALGLSCGASLSFLFKA : 324
hENT1   : CFGPKKVKPAEAETAGAIMAFFLCLGLALGAVFSFLFRA : 454
                       <======TM11=========> hENT2   : LL : 456
hHNP36  : LL : 326
hENT1   : IV : 456
```

FIG. 2B

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 2522 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:1:

```
GGATCCGCGG TGGCGCGACC CTCTGTCCCC GCCTCGGGGC GGAGCCCAGG TCCCAGCCTG      60
CGGAGCGCGA GACACGCCGA AATCCGCCCG AGGCTACCTG TGCGACTCCA GCCGCCCTGC     120
ACCGGAATCT GGGGAGACCC GCCCCCCGCC CCACCGGTCT GCGGCCCTCC GCCCCAGCGC     180
AGGTGCAGGT GCGGCTTCTC TGCCCCTTTC ACCCCAGGCG CATCCGCCGC GGCGGCCATG     240
GCGCGAGGAG ACGCCCCGCG GGACAGCTAC CACCTGGTCG GGATCAGCTT CTTCATCCTG     300
GGGCTGGGCA CCCTCCTTCC CTGGAACTTC TTCATCACCG CCATCCCGTA CTTCCAGGCG     360
CGACTGGCCG GGGCCGGCAA CAGCACAGCC AGGATCCTGA GCACCAACCA CACGGGTCCC     420
GAGGATGCCT TCAACTTCAA CAATTGGGTG ACGCTGCTGT CCCAGCTGCC CCTGCTGCTC     480
TTCACCCTCC TCAACTCCTT CCTGTACCAG TGCGTCCCGG AGACGGTGCG CATTCTGGGC     540
AGCCTGCTGG CCATACTGCT GCTCTTTGCC CTGACAGCAG CGCTGGTCAA GGTGGACATG     600
AGCCCCGGAC CCTTCTTCTC CATCACCATG GCCTCCGTCT GCTTCATCAA CTCCTTCAGT     660
GCAGTCCTAC AGGGCAGCCT CTTCGGGCAG CTGGGCACCA TGCCCTCCAC CTACAGCACC     720
CTCTTCCTCA GCGGCCAGGG CCTGGCTGGG ATCTTTGCTG CCCTTGCCAT GCTCCTGTCC     780
ATGGCCAGTG GCGTGGACGC CGAGACCTCT GCCCTGGGGT ACTTTATCAC GCCCTGTGTG     840
GGCATCCTCA TGTCCATCGT GTGTTACCTG AGCCTGCCTC ACCTGAAGTT TGCCCGCTAC     900
TACCTGGCCA ATAAATCATC CCAGGCCCAA GCTCAGGAGC TGGAGACCAA AGCTGAGCTC     960
CTCCAGTCTG ATGAGAACGG GATTCCCAGT AGTCCCCAGA AAGTAGCTCT GACCCTGGAT    1020
CTTGACCTGG AGAAGGAGCC GGAATCAGAG CCAGATGAGC CCCAGAAGCC AGGAAAACCT    1080
TCAGTCTTCA CTGTCTTCCA GAAGATCTGG CTGACAGCGC TGTGCCTTGT GTTGGTCTTC    1140
ACAGTCACCC TGTCCGTCTT CCCCGCCATC ACAGCCATGG TGACCAGCTC CACCAGTCCT    1200
```

```
GGGAAGTGGA GTCAGTTCTT CAACCCCATC TGCTGCTTCC TCCTCTTCAA CATCATGGAC    1260

TGGCTGGGAC GGAGCCTGAC CTCTTACTTC CTGTGGCCAG ACGAGGACAG CCGGCTGCTG    1320

CCCCTGCTGG TCTGCCTGCG GTTCCTGTTC GTGCCCCTCT TCATGCTGTG CCACGTGCCC    1380

CAGAGGTCCC GGCTGCCCAT CCTCTTCCCA CAGGATGCCT ACTTCATCAC CTTCATGCTG    1440

CTCTTTGCCG TTTCTAATGG CTACCTGGTG TCCCTCACCA TGTGCCTGGC GCCCAGGCAG    1500

GTGCTGCCAC ACGAGAGGGA GGTGGCCGGC GCCCTCATGA CCTTCTTCCT GGCCCTGGGA    1560

CTTTCCTGTG GAGCCTCCCT CTCCTTCCTC TTCAAGGCGC TGCTCTGAAG TGGCCCCTCC    1620

AGGCTCTTTG GCAGCCTCTT CTCGACGTCT CCTTCCGGAG CTGAGATCCA GCCCAGGGCG    1680

AATGGCGAGC TTGGCTCAGG CCTCTGCGGG GTGGAGGCCC CTGGGCCTGA GGCTGCCAGC    1740

AGCGGGCAGG AGCTGCTCTT CATCCACTTG GAGTGCTGCG GGAAGAAAT  CACCACCGGT    1800

CATTCTAACC CTCACCCAGG AATGGGGGTG ACTCGCACAA GACCTCATGG AAAGGGTGAT    1860

GACTAGGGAA AAGAGGGTGC AGGGCACGGC TGCTCCCCAC CACCAGGTCT GCATTTGTTC    1920

ATCATCATCA GGAGCAGAGG TGACCAGAGG GTTCAGAGTG GGAGGCAGGG CCAGCCCAGG    1980

CCAGGAGCGC CTCATCTTCC CAGGCCTCAG CCACCCAGGG TAAAAGGTGC CAGGGAAGTT    2040

GTGGGCACCT GAGAGGAGGA ACAGATGTGG AGGACCTGAG GGTGCTCAAA GGGCCAGGCT    2100

CAGCCTCAAG CAGTGTTTTC ATTGCCAACA CTTACTGTAC CCACTCCGCA GAGCCCCGCT    2160

GGGCCTGGGC CCCAGGGCCA CAGCTAGCCT GCATGTGTGT ACTGCACTTT ACAGTTTGCA    2220

AAGCTCTTCC ATACCCACTC TCTCACCGAA GCCTAATTGA GGCTCTTGGA AGGAGTCAGG    2280

CAAGGATTGT GCTTCCCCCA TTATACAGGT GACAAAACTG AGTCCTGGGG AAAGTGACTG    2340

GTCCGTGGTA GAGCCGGGAC CCAATCCCCT CTCTCTCCTC CCTGTTGGTG CTGTTCTTCC    2400

TGCCCAACAC CTGTTTCTCT TTTCCTCAAG GGGTTTGGGG CAGGAGCCTG GGCACTTACT    2460

CCCCGTTTTT GCTGTTTCTC CTTCTGACCC TGCTCTTGGG TCTAATAACC CCATTTATTT    2520

GT                                                                    2522
```

(2) INFORMATION FOR SEQ ID NO:2:

(i) SEQUENCE CHARACTERISTICS:
        (A) LENGTH: 456 amino acids
        (B) TYPE: amino acid
        (C) STRANDEDNESS: single
        (D) TOPOLOGY: linear (ii) MOLECULE TYPE: protein
        (A) DESCRIPTION: hENT2

(iii) HYPOTHETICAL: NO (v) FRAGMENT TYPE:

(vi) ORIGINAL SOURCE:
        (A) ORGANISM: Homo sapiens (xi) SEQUENCE DESCRIPTION: SEQ ID NO:2:

```
Met Ala Arg Gly Asp Ala Pro Arg Asp Ser Tyr His Leu Val Gly Ile
1               5                   10                  15

Ser Phe Phe Ile Leu Gly Leu Gly Thr Leu Leu Pro Trp Asn Phe Phe
                20                  25                  30

Ile Thr Ala Ile Pro Tyr Phe Gln Ala Arg Leu Ala Gly Ala Gly Asn
        35                  40                  45

Ser Thr Ala Arg Ile Leu Ser Asn His Thr Gly Pro Glu Asp Ala
    50                  55                  60
```

```
Phe Asn Phe Asn Asn Trp Val Thr Leu Leu Ser Gln Leu Pro Leu Leu
 65                  70                  75                  80

Leu Phe Thr Leu Leu Asn Ser Phe Leu Tyr Gln Cys Val Pro Glu Thr
                 85                  90                  95

Val Arg Ile Leu Gly Ser Leu Leu Ala Ile Leu Leu Leu Phe Ala Leu
                100                 105                 110

Thr Ala Ala Leu Val Lys Val Asp Met Ser Pro Gly Pro Phe Phe Ser
        115                 120                 125

Ile Thr Met Ala Ser Val Cys Phe Ile Asn Ser Phe Ser Ala Val Leu
        130                 135                 140

Gln Gly Ser Leu Phe Gly Gln Leu Gly Thr Met Pro Ser Thr Tyr Ser
145                 150                 155                 160

Thr Leu Phe Leu Ser Gly Gln Gly Leu Ala Gly Ile Phe Ala Ala Leu
                165                 170                 175

Ala Met Leu Leu Ser Met Ala Ser Gly Val Asp Ala Glu Thr Ser Ala
            180                 185                 190

Leu Gly Tyr Phe Ile Thr Pro Cys Val Gly Ile Leu Met Ser Ile Val
            195                 200                 205

Cys Tyr Leu Ser Leu Pro His Leu Lys Phe Ala Arg Tyr Tyr Leu Ala
210                 215                 220

Asn Lys Ser Ser Gln Ala Gln Ala Gln Glu Leu Glu Thr Lys Ala Glu
225                 230                 235                 240

Leu Leu Gln Ser Asp Glu Asn Gly Ile Pro Ser Ser Pro Gln Lys Val
                245                 250                 255

Ala Leu Thr Leu Asp Leu Asp Leu Glu Lys Glu Pro Glu Ser Glu Pro
            260                 265                 270

Asp Glu Pro Gln Lys Pro Gly Lys Pro Ser Val Phe Thr Val Phe Gln
        275                 280                 285

Lys Ile Trp Leu Thr Ala Leu Cys Leu Val Leu Val Phe Thr Val Thr
        290                 295                 300

Leu Ser Val Phe Pro Ala Ile Thr Ala Met Val Thr Ser Ser Thr Ser
305                 310                 315                 320

Pro Gly Lys Trp Ser Gln Phe Phe Asn Pro Ile Cys Cys Phe Leu Leu
                325                 330                 335

Phe Asn Ile Met Asp Trp Leu Gly Arg Ser Leu Thr Ser Tyr Phe Leu
            340                 345                 350

Trp Pro Asp Glu Asp Ser Arg Leu Leu Pro Leu Leu Val Cys Leu Arg
            355                 360                 365

Phe Leu Phe Val Pro Leu Phe Met Leu Cys His Val Pro Gln Arg Ser
370                 375                 380

Arg Leu Pro Ile Leu Phe Pro Gln Asp Ala Tyr Phe Ile Thr Phe Met
385                 390                 395                 400

Leu Leu Phe Ala Val Ser Asn Gly Tyr Leu Val Ser Leu Thr Met Cys
                405                 410                 415

Leu Ala Pro Arg Gln Val Leu Pro His Glu Arg Glu Val Ala Gly Ala
            420                 425                 430

Leu Met Thr Phe Phe Leu Ala Leu Gly Leu Ser Cys Gly Ala Ser Leu
            435                 440                 445

Ser Phe Leu Phe Lys Ala Leu Leu
            450                 455
```

(2) INFORMATION FOR SEQ ID NO:3:

(i) SEQUENCE CHARACTERISTICS:

```
          (A) LENGTH: 326 amino acids
          (B) TYPE: amino acid
          (C) STRANDEDNESS: single
          (D) TOPOLOGY: linear (ii) MOLECULE TYPE: protein
          (A) DESCRIPTION: hHNP36

(iii) HYPOTHETICAL: NO (v) FRAGMENT TYPE:

(vi) ORIGINAL SOURCE:
          (A) ORGANISM: Homo sapiens (xi) SEQUENCE DESCRIPTION: SEQ ID NO:3:
```

| | | | | | | | | | | | | | | | |
|---|---|---|---|---|---|---|---|---|---|---|---|---|---|---|---|
| Met | Ala | Ser | Val | Cys | Phe | Ile | Asn | Ser | Phe | Ser | Ala | Val | Leu | Gln | Gly |
| 1 | | | | 5 | | | | | 10 | | | | | 15 | |
| Ser | Leu | Phe | Gly | Gln | Leu | Gly | Thr | Met | Pro | Ser | Thr | Tyr | Ser | Thr | Leu |
| | | | 20 | | | | | 25 | | | | | 30 | | |
| Phe | Leu | Ser | Gly | Gln | Gly | Leu | Ala | Gly | Ile | Phe | Ala | Ala | Leu | Ala | Met |
| | | | | 35 | | | | | 40 | | | | | 45 | |
| Leu | Leu | Ser | Met | Ala | Ser | Gly | Val | Asp | Ala | Glu | Thr | Ser | Ala | Leu | Gly |
| | 50 | | | | | 55 | | | | | 60 | | | | |
| Tyr | Phe | Ile | Thr | Pro | Tyr | Val | Gly | Ile | Leu | Met | Ser | Ile | Val | Cys | Tyr |
| 65 | | | | | 70 | | | | | 75 | | | | | 80 |
| Leu | Ser | Leu | Pro | His | Leu | Lys | Phe | Ala | Arg | Tyr | Tyr | Leu | Ala | Asn | Lys |
| | | | | 85 | | | | | 90 | | | | | 95 | |
| Ser | Ser | Gln | Ala | Gln | Ala | Gln | Glu | Leu | Glu | Thr | Lys | Ala | Glu | Leu | Leu |
| | | | | 100 | | | | | 105 | | | | | 110 | |
| Gln | Ser | Asp | Glu | Asn | Gly | Ile | Pro | Ser | Ser | Pro | Gln | Lys | Val | Ala | Leu |
| | | | 115 | | | | | 120 | | | | | 125 | | |
| Thr | Leu | Asp | Leu | Asp | Leu | Glu | Lys | Glu | Pro | Glu | Ser | Glu | Pro | Asp | Glu |
| | 130 | | | | | 135 | | | | | 140 | | | | |
| Pro | Gln | Lys | Pro | Gly | Lys | Pro | Ser | Val | Phe | Thr | Val | Phe | Gln | Lys | Ile |
| 145 | | | | | 150 | | | | | 155 | | | | | 160 |
| Trp | Leu | Thr | Ala | Leu | Cys | Leu | Val | Leu | Val | Phe | Thr | Val | Thr | Leu | Ser |
| | | | | 165 | | | | | 170 | | | | | 175 | |
| Val | Phe | Pro | Ala | Ile | Thr | Ala | Met | Val | Thr | Ser | Ser | Thr | Ser | Pro | Gly |
| | | | 180 | | | | | 185 | | | | | 190 | | |
| Lys | Trp | Ser | Gln | Phe | Phe | Asn | Pro | Ile | Cys | Cys | Phe | Leu | Leu | Phe | Asn |
| | | | 195 | | | | | 200 | | | | | 205 | | |
| Ile | Met | Asp | Trp | Leu | Gly | Arg | Ser | Leu | Thr | Ser | Tyr | Phe | Leu | Trp | Pro |
| | 210 | | | | | 215 | | | | | 220 | | | | |
| Asp | Glu | Asp | Ser | Arg | Leu | Leu | Pro | Leu | Leu | Val | Cys | Leu | Arg | Phe | Leu |
| 225 | | | | | 230 | | | | | 235 | | | | | 240 |
| Phe | Val | Pro | Leu | Phe | Met | Leu | Cys | His | Val | Pro | Gln | Arg | Ser | Arg | Leu |
| | | | | 245 | | | | | 250 | | | | | 255 | |
| Pro | Ile | Leu | Phe | Pro | Gln | Asp | Ala | Tyr | Phe | Ile | Thr | Phe | Met | Leu | Leu |
| | | | 260 | | | | | 265 | | | | | 270 | | |
| Phe | Ala | Val | Ser | Asn | Gly | Tyr | Leu | Val | Ser | Leu | Thr | Met | Cys | Leu | Ala |
| | | | 275 | | | | | 280 | | | | | 285 | | |
| Pro | Arg | Gln | Val | Leu | Pro | His | Glu | Arg | Glu | Val | Ala | Gly | Ala | Leu | Met |
| | 290 | | | | | 295 | | | | | 300 | | | | |
| Thr | Phe | Phe | Leu | Ala | Leu | Gly | Leu | Ser | Cys | Gly | Ala | Ser | Leu | Ser | Phe |
| 305 | | | | | 310 | | | | | 315 | | | | | 320 |
| Leu | Phe | Lys | Ala | Leu | Leu | | | | | | | | | | |
| | | | | 325 | | | | | | | | | | | |

(2) INFORMATION FOR SEQ ID NO:4:

(i) SEQUENCE CHARACTERISTICS:
        (A) LENGTH: 456 amino acids
        (B) TYPE: amino acid
        (C) STRANDEDNESS: single
        (D) TOPOLOGY: linear (ii) MOLECULE TYPE: protein
        (A) DESCRIPTION: hENT1

(iii) HYPOTHETICAL: NO (v) FRAGMENT TYPE:

(vi) ORIGINAL SOURCE:
        (A) ORGANISM: Homo sapiens (xi) SEQUENCE DESCRIPTION: SEQ ID NO:4:

```
Met Thr Thr Ser His Gln Pro Gln Asp Arg Tyr Lys Ala Val Trp Leu
 1               5                  10                  15

Ile Phe Phe Met Leu Gly Leu Gly Thr Leu Leu Pro Trp Asn Phe Phe
                20                  25                  30

Met Thr Ala Thr Gln Tyr Phe Thr Asn Arg Leu Asp Met Ser Gln Asn
            35                  40                  45

Val Ser Leu Val Thr Ala Glu Leu Ser Lys Asp Ala Gln Ala Ser Ala
50                  55                  60

Ala Pro Ala Ala Pro Leu Pro Glu Arg Asn Ser Leu Ser Ala Ile Phe
65                  70                  75                  80

Asn Asn Val Met Thr Leu Cys Ala Met Leu Pro Leu Leu Leu Phe Thr
                85                  90                  95

Tyr Leu Asn Ser Phe Leu His Gln Arg Ile Pro Gln Ser Val Arg Ile
                100                 105                 110

Leu Gly Ser Leu Val Ala Ile Leu Leu Val Phe Leu Ile Thr Ala Ile
            115                 120                 125

Leu Val Lys Val Gln Leu Asp Ala Leu Pro Phe Phe Val Ile Thr Met
130                 135                 140

Ile Lys Ile Val Leu Ile Asn Ser Phe Gly Ala Ile Leu Gln Gly Ser
145                 150                 155                 160

Leu Phe Gly Leu Ala Gly Leu Leu Pro Ala Ser Tyr Thr Ala Pro Ile
                165                 170                 175

Met Ser Gly Gln Gly Leu Ala Gly Phe Phe Ala Ser Val Ala Met Ile
                180                 185                 190

Cys Ala Ile Ala Ser Gly Ser Glu Leu Ser Glu Ser Ala Phe Gly Tyr
            195                 200                 205

Phe Ile Thr Ala Cys Ala Val Ile Ile Leu Thr Ile Ile Cys Tyr Leu
210                 215                 220

Gly Leu Pro Arg Leu Glu Phe Tyr Arg Tyr Tyr Gln Gln Leu Lys Leu
225                 230                 235                 240

Glu Gly Pro Gly Glu Gln Glu Thr Lys Leu Asp Leu Ile Ser Lys Gly
                245                 250                 255

Glu Glu Pro Arg Ala Gly Lys Glu Glu Ser Gly Val Ser Val Ser Asn
                260                 265                 270

Ser Gln Pro Thr Asn Glu Ser His Ser Ile Lys Ala Ile Leu Lys Asn
            275                 280                 285

Ile Ser Val Leu Ala Phe Ser Val Cys Phe Ile Phe Thr Ile Thr Ile
290                 295                 300
```

```
Gly Met Phe Pro Ala Val Thr Val Glu Val Lys Ser Ser Ile Ala Gly
305                 310                 315                 320

Ser Ser Thr Trp Glu Arg Tyr Phe Ile Pro Val Ser Cys Phe Leu Thr
                325                 330                 335

Phe Asn Ile Phe Asp Trp Leu Gly Arg Ser Leu Thr Ala Val Phe Met
                340                 345                 350

Trp Pro Gly Lys Asp Ser Arg Trp Leu Pro Ser Leu Val Leu Ala Arg
                355                 360                 365

Leu Val Phe Val Pro Leu Leu Leu Cys Asn Ile Lys Pro Arg Arg
                370                 375                 380

Tyr Leu Thr Val Val Phe Glu His Asp Ala Trp Phe Ile Phe Met
385                 390                 395                 400

Ala Ala Phe Ala Phe Ser Asn Gly Tyr Leu Ala Ser Leu Cys Met Cys
                405                 410                 415

Phe Gly Pro Lys Lys Val Lys Pro Ala Glu Ala Glu Thr Ala Gly Ala
                420                 425                 430

Ile Met Ala Phe Phe Leu Cys Leu Gly Leu Ala Leu Gly Ala Val Phe
                435                 440                 445

Ser Phe Leu Phe Arg Ala Ile Val
450                 455

(2) INFORMATION FOR SEQ ID NO:5:

(i) SEQUENCE CHARACTERISTICS:
        (A) LENGTH:6354 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO:5:

GGATCCGCGG TGGCGCGACC CTCTGTCCCC GCCTCGGGGC GGAGCCCAGG TCCCAGCCTG      60

CGGAGCGCGA GACACGCCGA AATCCGCCCG AGGCTACCTG TGCGACTCCA GCCGCCCTGC    120

ACCGGAATCT GGGGAGACCC GCCCCCCGCC CCACCGGTCT GCGGCCCTCC GCCCCAGCGC    180

AGGTGCAGGT GCGGCTTCTC TGCCCCTTTC ACCCCAGGCG CATCCGCCGC GGCGGCCATG    240

GCGCGAGGAG ACGCCCCGCG GGACAGGTGA GTGGGCCCGG GTGCGTTGCA AGTGGCCGGG    300

GGCGTTGCAG ACCCGCTCCC TGAAGGCGCT CCGAGGCTCA GAGAAGACCG GATCGAACTA    360

CAATTCCCAT CAGCCGACTC CCTCGGCCGC CGGAACCGGG GTGATGGGGG TTGTAGTCCG    420

CTCCGGAGGG GGTGGCCTGG GAGGCGGGAG GGCCTGCGGA GGCGGGTGCG TCCTCGGGGT    480

GACCTTCCCA CCGATCCCCA CAGCTACCAC CTGGTCGGGA TCAGCTTCTT CATCCTGGGG    540

CTGGGCACCC TCCTTCCCTG GAACTTCTTC ATCACCGCCA TCCCGGTGAG ACTCCTGGCG    600

GCGTGGCAGC CTCGTGGCCA CAGCCAGCAC CCCTCCCTCC AGCCCTTTGG ATGAAGCTTA    660

GCGGGCGCTT CCTCACCGCG CACCTGTGAC CCCTCGTTGA GCTCATTATG GGCTGAAGCT    720

CGGAGAGGGG AATGCTTCCC CCGTGGCTAG GAAAGTAGAA CTTCAGCAAT GCCCACATCT    780

CAGAGGGCA AGGCCACCAG CCCACAGGGT CTGGAATGAG CAAAGGCGCT GCCACCCCTC    840

TCTGTGTGTC GTTATTCCTG AGTCAGTCAC CCCAAAAGTC GGTTATCGAA CGTTTGATTT    900

TCTTTGAAAT ACCATGAATT TCATTCATTC ACTCATTCAT TCAACAAACT TTTTTTTTTT    960

TTTTTTTTTT GAGACAGAGT CTGGCTCTTT CGCCCAGGCT GGAGTGCAGT GGCGCCATCT   1020
```

```
                                              -continued

CGGCTCACTG CAAGCTCCGC CTCCCGGGTT CACGCCATTC TCCTGCCTCA CCCTCCCGAG    1080

TAGCTGGGAC TACAGGCGCC CGCCGCCACG CGCGGCTATT TTTTTTTGTA TTTTTAGTAG    1140

AGACGGGGTT TCACCGTGTT AGCCAGGATG GTCTCGATCT CCTGACCTCG TGATCCTCCC    1200

GCCTCGGCCT CCCAAAGTGC TGGGATTACA GGCGTGAGCC ACCGTGCCCA GCCTCATTCA    1260

ACAAACTTTT AGTGTGCATC TACTGTGGAG CAGGCACTGG GGACACAGGA GGAAACAGCA    1320

GGGAGGCTCT TCAGGGAAGG CAGAAATGTG GGGTTTGCAT TGTCTTTGGG ACCGGGTTAT    1380

TCATCTGTAT TCACTGCAAC AACTTTGCAA ATGCTTCTTG GGTACTGGCT CTGTGCTGGG    1440

CCCTGGAAAC CCAGAGATGA ATCAGCCCCT GGGCTTGAGA GCAAGAAGGG GCCAAAGAGC    1500

TATTAATAAT GTAACATGAT GCGTGACATT CCAGGCTTGC AGCAGAGTGC AGTGGGTCCC    1560

CAGGGAAGGA GAAAGTTCCT TCTGCTTCAT GGAAGAGGAG ATTTGTAAAT TGGGAGTAGG    1620

GTAGGCAAAG TGCGTGTGGA GGGGTGTGGT CAGTAGGGCA TTCCAAGCCG AGGCGACAGC    1680

CATGCCAAAG GCAGGCAGGC AAGAGACGAT CAGCCTGTTT AGAGGGAGAT TCCACAGCCA    1740

GGGCTGCCTG GAGCTTAGCA GGATGGAGCA GAAGATGGGG CACAAAGGGA GACTAGGATC    1800

TGATTCTGAA GAGCTGTTCC ATTTGGGGCT TTGCCCTGCA GGCAATAGGG AGGCATGAAT    1860

CGGGGTGTTG AGGAGTGAGG AGGTTAAGCA GAGGAGTGGC AGGCTATGTG CTCTAGAGAG    1920

AATGCAGTTG TTCAGCACTT AGGCCAAAGC CTGGCTTGAC AGTAGGCGCT CAATAAATAC    1980

CCGTGGAATG AATGAATGTA GCAGCTGCTG CAGGAGTGGG GATGGGGGCT GGAACCAGGG    2040

CACTGAAGAG GAGGGGCCGT CCAAGGCTGG ATCGAGGCTC TTGCTGGGGG CTCTTAATGC    2100

TTAGGCTGTG TCCCAGACTT CAGCCATTTA ACTCAGCACA CATTCATGGA GCTCCGACTG    2160

TGTGCCGGCT GCTGGGAACA GAACAAGGGC AAGGCAGACA AGTCCCCACA GACATTAGAA    2220

AGCAATCACA AGTGAGGGGG AAGGCAGCGG GGGAAGGCTG AGAGGTGCTG ACCCTCCACC    2280

ACCTCCCTAC CTGGCAGTAC TTCCAGGCGC GACTGGCCGG GGCCGGCAAC AGCACAGCCA    2340

GGATCCTGAG CACCAACCAC ACGGGTCCCG AGGATGCCTT CAACTTCAAC AATTGGGTGA    2400

CGCTGCTGTC CCAGCTGCCC CTGCTGCTCT TCACCCTCCT CAACTCCTTC CTGTACCAGT    2460

GGTGAGAGGC CTGCCCTGGC TCCTGCGCCC TCTGCCGAGG CAGCTTCATT GAGGCCCTCC    2520

CCTGCGCCCC CTGCCCTCCA GCCCTACTGC CCAGCCCCAG GTGTCGAGCC TCCTTCCCCA    2580

GCCCCCTCTG GCCTGGGCCC CACTGATGCA CTCTGCCTGC TTCTGAGCAA GCGTCCCGGA    2640

GACGGTGCGC ATTCTGGGCA GCCTGCTGGC CATACTGCTG CTCTTTGCCC TGACAGCAGC    2700

GCTGGTCAAG GTGGACATGA GCCCCGGACC CTTCTTCTCC ATCACCATGG CCTCCGTCTG    2760

CTTCATCAAC TGTGAGCACC TCCACCCCCT CTCCAGCCAG CCTATGCAGG GCTTCAGCCT    2820

GGCCTCATCA TTGAAAGGGC CCAGCATATC CGAGAAGGGC AGACAGCATC ATGGTCGCTC    2880

ATATCCCTGG TGAAGAAACT GAGGCCCACA GGGAGGGGAA GAGTCACTTG TCCGGTGACC    2940

TAGGAGCAGG CCTCCTGGTC AACAGCCCCA CAGACCAATG GCTGCACCTC AGAAGAGGAC    3000

TGAATAGCGG GTGTTGCCCC CGAGTGCTCA GAGTCCCTAG GGAAGCTCAC ACCTGCGCAA    3060

CCTTGTCCAG AGTCCCCTGT GTATCCTGCC GGCACCTCCT CCAGGGAGCC TCTGAGTCTT    3120

GCCTAGTTGA GCAGCAGCCC CCATCCCTGT CCTCCACAGC CTTCAGTGCA GTCCTACAGG    3180

GCAGCCTCTT CGGGCAGCTG GCACCATGC CCTCCACCTA CAGCACCCTC TTCCTCAGCG    3240

GCCAGGGCCT GGCTGGGATC TTTGCTGCCC TTGCCATGCT CCTGTCCATG GCCAGTGAGT    3300

GCACTTGGGT GGCTGGGAGG GCTGGGGTGG CCTCTGAGGT TTGGGGAAGA GAGAGGGCAT    3360

GTGAGAGCAA GACACATGGG TTCTGGGTGA AGATGGAGGT AAGCGGGTGA TATGGAAATG    3420
```

```
GGGATTGGTC TGGGGCTAGG GAATGGGGCT CATGGGCCCT GCAGTGAGGA GTAATAACCA    3480

AGTGAGGACT GGGTTAACTC AGGGACAGGG GCAGGATTCC TGGGGCTAAT ACTGGCATGT    3540

GGCAGCAGGT TGAAGTTGAA GGATAAGGGG ATGGGTTTGG GATTCAGATA GTCTTGGGTT    3600

TGAATCTGCT TCACCGCTTA CCAGCTAGGG GTGTTGGACA AGGCTTGTCA CCTCTCTGTG    3660

CTAGCTTCCC CACCGATGTG ATTGGTACAG CTCCCTGCTC AGATTGTAAT GAGCATGCAA    3720

TGAGAGAAGG CTACTGGCAC ATAGTACGTG CTCAACAAAA ATGACACATG GGAAAGTGA     3780

GAGAAGTGCA GGGCTGCTCT GGGGCCCTGT ACAAGATTCC CATTTGTCAG TGAAGGGAGG    3840

AGCGGAAGAG GCTGGGAGTG GGTCTGAGAA GTACACAATG GGAAGTGGGA CAAGAGTTGG    3900

AAGCCCCGTG GGAGCCGGCG GGACCAGGTG CCTCTCTTCT GCAGCTGAAG TTCCTCCGCA    3960

GGTGGCGTGG ACGCCGAGAC CTCTGCCCTG GGTACTTTA TCACGCCCTG TGTGGGCATC     4020

CTCATGTCCA TCGTGTGTTA CCTGAGCCTG CCTCACCTGG TGAGCCTGCT GTTGGGCTCG    4080

AGGCCCCACC TCAAAGCATC TTGGATAGAG TCCTGAGCCT GAAGCCCTGA GAGAGGCCAG    4140

GGGAGGTGGA GGAGACCTGG TCTCAGCCCT GACCCCAGA GAAGACACTG AGGGGCCCCA     4200

GCCTCCAGGC CAATGGTATG GGGAGGGATC CAGACACCTC AGGCAAGCCA GGCAGGCCCA    4260

ACACTTTCCT GTCCTTCTGC AGAAGTTTGC CCGCTACTAC CTGGCCAATA AATCATCCCA    4320

GGCCCAAGCT CAGGAGCTGG AGACCAAAGC TGAGCTCCTC CAGTCTGGTA AGCCCTGAGA    4380

CCCTCCTGGG GAGGTGGGAG ATGCAGAGGA AGCTAGAGCC ACCTCCCCTG GGAAGCTGTT    4440

CCATCTGTTC CCAGCCAGAG CCCACCCCTA GTAGCCTTGT GCAAACAGGA AGATCATGAA    4500

GGGAAGTTGG TAGGATTAAA GTCATCCCTG CTGTTGTTTG GGCCTCAGTT TCCACCTCTA    4560

TAAAATGGGG AGGCGACAGA AGTTCCATGC ATGCAAACTT TGGATCGAAG ACCTCTGAAT    4620

TGGAATACTA GTTTCACAAC ATCCCRGCTG TGTGGCCTGA GACAAACCAC TTAGCCACTG    4680

CACCCCTCTG AACCTCAATG TGTCATTTGT AAAGCAATGG TAATGAGATA ATCCATCTAA    4740

GGTGCTTCGC TCATCACCCG ACCCATGCAC GCGCTTCTGG TAGCTATGCA TATTTCCATC    4800

ATGAATTCCC TTCGCCTGCA GCCTCAGCTT AGGCTGGAGG AAGATCACCT TTTTTGTTT    4860

TGGGGTGAGG GGGTTGTTGT TATTTTGAGT CAGGATCTCA CTCTGTCACC TAGGCTGCAC    4920

TGCAGTGCTA TCACAACTCA ACTGCAGCTT CGACCTTCTG GGCTCAAGTG AGCCACCTCA    4980

GTCTCCCGAG TAGCTGGGAC TATAGGTGCA GGCTGCCATG CCCGGCTAAT TTTTTTATTT    5040

TTGTAGAGAT GGTGATTCAC CATGTTGCCC AGGCTGGTCT CGAACTCCTG GCTCAAGCA     5100

ATATGCCCGC TTCGGCCTTC CAAAATGTTG GGATTACAGG CGTGAGCCAC CATGCCGAGC    5160

TGAGGATCAC TTGTTTTAAC TGCTGGGAAT CTCCCTTCGT TGGGCCTGGC TGTCGGGAAA    5220

CCTGGGTCAC AAGCATGACC CTTCCCCGTC CCCCCTCACC CCAGATGAGA ACGGGATTCC    5280

CAGTAGTCCC CAGAAAGTAG CTCTGACCCT GGATCTTGAC CTGGAGAAGG AGCCGGAATC    5340

AGAGCCAGAT GAGCCCCAGA AGCCAGGAAA ACCTTCAGTC TTCACTGTCT TCCAGAAGGT    5400

TTGGCTTGGA TACAGCCCCC AACCACCATC TTTGGGAAG AATGGGGCTC ACATTGACTC     5460

CAAGGTCATA GGGTCACAGT GGGTCAGGGA CACAGCTGGG CCAGGCCCCA AGTGTCCTGC    5520

TCCCACATGG GGCTTGGGCA AGAGGGTGGG GCCCTGGGAC TGCCCTGCCT GCTCACACCC    5580

CTGCCTCYGG CTCCCAGATC TGGCTGACAG CGCTGTGCCT TGTGTTGGTC TTCACAGTCA    5640

CCCTGTCCGT CTTCCCCGCC ATCACAGCCA TGGTGACCAG CTCCACCAGT CCTGGGAAGT    5700

GGAGTGAGTG TCAGGGTGGA GAAGACGGCA GGGCAGGGGG TACAAAGGGG AGAGGACGGG    5760
```

```
AGAGGGGAGT TGGAGACCAG TATGAGCTGC AGCCGTTTCC CTCCCAGGTC AGTTCTTCAA      5820

CCCCATCTGC TGCTTCCTCC TCTTCAACAT CATGGACTGG CTGGGACGGA GCCTGACCTC      5880

TTACTTCCTG TGGGTAAGCA CACCAGGGCT GGGTGATCCG ATGTTTTAGG AAGCAGTTTG      5940

GGATCCGAGG GCTTGAAAGA GCACGGAGGT GATTTTCTGG TAGTCCAAGT GGCCTGGTAA      6000

TGCAACCACT GGCCAAGCAG CAGGGAGCAC TTGGGCCCTG GAGGCGTGCA AGGCCAGGGC      6060

TTGCACTGTG AGCTCCCTGA AAGCAAAAAT CATGTCCAGC TGACCTCTGT GTCCCCAGCA      6120

TCCAGCCTTT GCTGCTCAGA GAATGTTACA TGGAGGTTCC TGCACCAGGT GAGGGACTGA      6180

GCAAGATCTT AGTTTTGGGG TTGGTTTTAG CCATGGTGCT GTATCTTTAA ATGAAATCTT      6240

CCAAAGAGAC AATACATAAC GCAGGTGAAA GANGANCTGG TCTCATCCAA GTCAGGACAN      6300

NGAGCTGATC TACAGCTTCC AATCCCACTC AGAAACCCTC TGCCCCCAAN GGGG            6354

(2) INFORMATION FOR SEQ ID NO:6:

(i) SEQUENCE CHARACTERISTICS:
        (A) LENGTH: 2140 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO:6:

CATAGGGACC TAGTAAAACA AATTAAAGTG GTAGTTATTT GGATCAGTGA TAACTAATTC        60

TTATAATTTT TGCAGATGGA ATTGGCTGCT CTAGAAAAAA TTAAATCTAC TTGGATTAAA       120

AACCAAGATG ACAGCTTGAC TGAAACAGAC ACTCTGGTAT GTATGGGTCA GTTTCCTGTT       180

TCAGCTGTTT CAAATAGTGT TTGTCCCTTT AGAAATAACG GCAGAAGGAC CCTCAGGACC       240

ACCATAGAAA TTTCACCTAA ATCTGCAGGC TTATGAATGT CCTGCACTCT CNTTCTCCTG       300

AAATCCTTAC CCCGTGGAAT GCAACCTACT ACCTGGGTGT AGACACCAAG TTGCTCTCAA       360

ACTTAGTATA CCAGAAATGT CCTCATTCTG CCCTTTAATA AGAGCTGACC AAATGCTAGC       420

TGGGAAAACT TCTCACCATC TGTCACCAGC GTTCTCCCTG GAAAACATCC CTTCCTCAAT       480

TGGGATGTTG CTGTTTCCCG TGGGCCAAGG CAACCCACAA CATTCAAGTC TCGACTGGTA       540

CTGGTCCGTG TTCTTAAGAG GTGCTGGAGC TGCCCAAGGA GTGCAGGCTT AARCCCCAGT       600

GAAGTGGAAT TGAGTTGGTT GGGATGCCCA GTTTTTTTAC AGGGTCGAAT TGCACAAACA       660

TTTACTGTGC CCCTGCTTGT GTTGGGCACT GAAGATGCAA ACATGAGTGA GCCACAGTTT       720

GCATCCCCTG TACCTCCGGC CCCAGGGAGG TACAGGGGAT GCAAACTGGA GAAGCGACAT       780

CTGAGCTGGG CTTTGCGGGT TACGTCAAAG TTCATCCCGT GGGACCAGAG GCAGGACCCT       840

TGTGGGAAG GAGCATAGAA CTTTACAGAA TGCCATCTAG GGATGAGCCT CACGGTGGGA        900

CCTGCTGGA GTTGACTAGA ATCTGTGAAA GAATTATTTT AAGCCTTATG TTTTCTATAG        960

TAAATAAGAC TACATTTAAA GATCTTATGT ATTTAGGCTT GATTCAAGAT TAATTTGAAA      1020

CTCACTACCC TAACTTACAT TTTCTAGTTC ACCAGGTAAT CTGAATAATC CTACTTCCAC      1080

CGTGGCCCCA CTGTAGTCCG TACTCACGT GGCAAGTACA GTGTGSCCTT TTCAAAATTA       1140

AATTCCAATT GTGTCACTTC CTGATTAAAA CTCTTCAGTG ATTGGCCAAA TCTCAGCAAT      1200

TTAATGTTGA GTGAGTAAAA AGAAGCCGGA ATGCCAAAAA ATGCACGCCA TAGGATTCCA      1260

GTTCTGTGAA ACTCACAAAC AGGCAAAACT AATCCATGAG GGTGACGTCA GCATACCTTG      1320
```

-continued

```
TTACCCCAGG GGGAGAGGGA GGGGCATCGG GAGGCCTCAG GAATGCTGGA ACGTTCTGTC   1380

TTGATCTGGT TAATGGTCAC CTGGGGGCAT ATTTGCATAA AAATTCAAGT TGACTATTNT   1440

AGATTTGTGC TTCTTACTTT ATAGAAGTTA TTCCCTCAGT AAACATTTTG AAAACATAAA   1500

GACCAGGCAG AGGCAGGGAA GTAGGCAGGT GTGCGGCCTG TATTGGTAGC AGAGTCCTCC   1560

CTGAGGGCTG GATCATTAGG GAGGTAGTGG GCCCAGGGAG GAGGCACGGG AGGTTAATTT   1620

AGAAAGGTGG CCCAGGCTGG GTCATGGTGG CCTCAGAGGC CCCACTAAAG AATCAGACTT   1680

GGCCAGGTGT GGTGGCTCAC ACCTGTAATC CCAGTACTTT TGGGAGGCTG AGGCAGGCAC   1740

ATTGTTTGAG CCTGGGGATT CAAGACCAGC CCGGGCAACA TGGGAAAAAC CCSGTCTCTA   1800

CAAAAAAAAA AAAAAAAAAA AATAGTAATA CAAAAAAATT AGCCAGGCAT GCTGACATGC   1860

ACCTGTACTT GGAAGGCTGA GGTAAGATAA CCACTTGAGC CCAGGAGTTC AAGGCTGCAG   1920

TGAGCTGAGA CCATGCCACT GCACTNCAGG CTGTGCAAGA GAGCAAGACC CTGTCTAAAA   1980

AAAATTTAAA AGGATGTCAG GAATTAGGCT GGGGGCGGTG GTTCATGCCT GTAATCCCAG   2040

CACTTTGGGA GGCCGAGGCG GCGGGTTCC GCAGGCCCCT AGGTGGGCG GGCCCGAGC     2100

CAGAGTCGAG TCCCTGAGGC GGGTGGGGGA AGGAGAGACG                       2140
```

(2) INFORMATION FOR SEQ ID NO:7:

(i) SEQUENCE CHARACTERISTICS:
        (A) LENGTH: 1272 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO:7:

```
CTAGAATTCA GCGGCCGCTG AATTCTAGGG CATCCTCATG TCCATCGTGT GTTACCTGAG     60

CCTGCCTCAC CTGAAGTTTG CCCGCTACTA CCTGGCCAAT AAATCATCCC AGGCCCAAGC    120

TCAGGAGCTG GAGACCAAAG CTGAGCTCCT CCAGTCTGGT AAGCCCTGAG ACCCTCCTGG    180

GGAGGTGGGA GATGCAGAGG AAGCTAGAGC CACCTCCCCT GGGAAGCTGT TCCATCTGTT    240

CCCAGCCAGA GCCCACCCCT AGTAGCCTTG TGCAAACAGG AAGATCATGA AGGGAAGTTG    300

GTAGGATTAA AGTCATCCCT GCTGTTGTTT GGGCCTCAGT TTCCACCTCT ATAAAATGGG    360

GAGGCGACAG AAGTTCCATG CATGCAAACT TTGGATCGAA GACCTCTGAA TTGGAATACT    420

AGTTTCACAA CATCCCRGCT GTGTGGCCTG AGACAAACCA CTTAGCCACT GCACCCCTCT    480

GAACCTCAAT GTGTCATTTG TAAAGCAATG GTAATGAGAT AATCCATCTA AGGTGCTTCG    540

CTCATCACCC GACCCATGCA CGCGCTTCTG GTAGCTATGC ATATTTCCAT CATGAATTCC    600

CTTCGCCTGC AGCCTCAGCT TAGGCTGGAG GAAGATCACC TTTTTTTGTT TTGGGGTGAG    660

GGGGTTGTTG TTATTTTGAG TCAGGATCTC ACTCTGTCAC CTAGGCTGCA CTGCAGTGCT    720

ATCACAACTC AACTGCAGCT TCGACCTTCT GGGCTCAAGT GAGCCACCTC AGTCTCCCGA    780

GTAGCTGGGA CTATAGGTGC AGGCTGCCAT GCCCGGCTAA TTTTTTTATT TTTGTAGAGA    840

TGGTGATTCA CCATGTTGCC CAGGCTGGTC TCGAACTCCT GGGCTCAAGC AATATGCCCG    900

CTTCGGCCTT CCAAAATGTT GGGATTACAG GCGTGAGCCA CCATGCCGAG CTGAGGATCA    960

CTTGTTTTAA CTGCTGGGAA TCTCCCTTCG TTGGGCCTGG CTGTCGGGAA ACCTGGGTCA   1020

CAAGCATGAC CCTTCCCCGT CCCCCCTCAC CCCAGATGAG AACGGGATTC CCAGTAGTCC   1080
```

```
CCAGAAAGTA GCTCTGACCC TGGATCTTGA CCTGGAGAAG GAGCCGGAAT CAGAGCCAGA    1140

TGAGCCCCAG AAGCCAGGAA AACCTTCAGT CTTCACTGTC TTCCAGAAGA TCTGGCTGAC    1200

AGCGCTGTGC CTTGTGTTGG TCTTCACAGT CACCCTGTCC GTCTTCCCCG CCATCACAGC    1260

CATGGTGACC AG                                                        1272
```

(2) INFORMATION FOR SEQ ID NO:8:

(i) SEQUENCE CHARACTERISTICS:
        (A) LENGTH: 247 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:8:

```
Met Ala Arg Gly Asp Ala Pro Arg Asp Ser Tyr His Leu Val Gly Ile
1               5                  10                  15

Ser Phe Phe Ile Leu Gly Leu Gly Thr Leu Leu Pro Trp Asn Phe Phe
            20                  25                  30

Ile Thr Ala Ile Pro Tyr Phe Gln Ala Arg Leu Ala Gly Ala Gly Asn
        35                  40                  45

Ser Thr Ala Arg Ile Leu Ser Thr Asn His Thr Gly Pro Glu Asp Ala
50                  55                  60

Phe Asn Phe Asn Asn Trp Val Thr Leu Leu Ser Gln Leu Pro Leu Leu
65                  70                  75                  80

Leu Phe Thr Leu Leu Asn Ser Phe Leu Tyr Gln Cys Val Pro Glu Thr
                85                  90                  95

Val Arg Ile Leu Gly Ser Leu Leu Ala Ile Leu Leu Phe Ala Leu
            100                 105                 110

Thr Ala Ala Leu Val Lys Val Asp Met Ser Pro Gly Pro Phe Phe Ser
            115                 120                 125

Ile Thr Met Ala Ser Val Cys Phe Ile Asn Ser Phe Ser Ala Val Leu
130                 135                 140

Gln Gly Ser Leu Phe Gly Gln Leu Gly Thr Met Pro Ser Thr Tyr Ser
145                 150                 155                 160

Thr Leu Phe Leu Ser Gly Gln Gly Leu Ala Gly Ile Phe Ala Ala Leu
                165                 170                 175

Ala Met Leu Leu Ser Met Ala Ser Gly Val Asp Ala Glu Thr Ser Ala
            180                 185                 190

Leu Gly Tyr Phe Ile Thr Pro Cys Val Gly Ile Leu Met Ser Ile Val
            195                 200                 205

Cys Tyr Leu Ser Leu Pro His Leu Lys Phe Ala Arg Tyr Tyr Leu Ala
210                 215                 220

Asn Lys Ser Ser Gln Ala Gln Ala Gln Glu Leu Glu Thr Lys Ala Glu
225                 230                 235                 240

Leu Leu Gln Ser Gly Lys Pro
                245
```

(2) INFORMATION FOR SEQ ID NO:9:

(i) SEQUENCE CHARACTERISTICS:
        (A) LENGTH: 1847 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO:9:

```
ATGGCGCGAG GAGACGCCCC GCGGGACAGC TACCACCTGG TCGGGATCAG CTTCTTCATC      60

CTGGGGCTGG GCACCCTCCT TCCCTGGAAC TTCTTCATCA CCGCCATCCC GTACTTCCAG     120

GCGCGACTGG CCGGGGCCGG CAACAGCACA GCCAGGATCC TGAGCACCAA CCACACGGGT     180

CCCGAGGATG CCTTCAACTT CAACAATTGG GTGACGCTGC TGTCCCAGCT GCCCCTGCTG     240

CTCTTCACCC TCCTCAACTC CTTCCTGTAC CAGTGCGTCC CGGAGACGGT GCGCATTCTG     300

GGCAGCCTGC TGGCCATACT GCTGCTCTTT GCCCTGACAG CAGCGCTGGT CAAGGTGGAC     360

ATGAGCCCCG GACCCTTCTT CTCCATCACC ATGGCCTCCG TCTGCTTCAT CAACTCCTTC     420

AGTGCAGTCC TACAGGGCAG CCTCTTCGGG CAGCTGGGCA CCATGCCCTC CACCTACAGC     480

ACCCTCTTCC TCAGCGGCCA GGGCCTGGCT GGGATCTTTG CTGCCCTTGC CATGCTCCTG     540

TCCATGGCCA GTGGCGTGGA CGCCGAGACC TCTGCCCTGG GGTACTTTAT CACGCCCTGT     600

GTGGGCATCC TCATGTCCAT CGTGTGTTAC CTGAGCCTGC CTCACCTGAA GTTTGCCCGC     660

TACTACCTGG CCAATAAATC ATCCCAGGCC CAAGCTCAGG AGCTGGAGAC CAAAGCTGAG     720

CTCCTCCAGT CTGGTAAGCC CTGAGACCCT CCTGGGGAGG TGGGAGATGC AGAGGAAGCT     780

AGAGCCACCT CCCCTGGGAA GCTGTTCCAT CTGTTCCCAG CCAGAGCCCA CCCCTAGTAG     840

CCTTGTGCAA ACAGGAAGAT CATGAAGGGA AGTTGGTAGG ATTAAAGTCA TCCCTGCTGT     900

TGTTTGGGCC TCAGTTTCCA CCTCTATAAA ATGGGGAGGC GACAGAAGTT CCATGCATGC     960

AAACTTTGGA TCGAAGACCT CTGAATTGGA ATACTAGTTT CACAACATCC CRGCTGTGTG    1020

GCCTGAGACA AACCACTTAG CCACTGCACC CCTCTGAACC TCAATGTGTC ATTTGTAAAG    1080

CAATGGTAAT GAGATAATCC ATCTAAGGTG CTTCGCTCAT CACCCGACCC ATGCACGCGC    1140

TTCTGGTAGC TATGCATATT TCCATCATGA ATTCCCTTCG CCTGCAGCCT CAGCTTAGGC    1200

TGGAGGAAGA TCACCTTTTT TTGTTTTGGG GTGAGGGGGT TGTTGTTATT TTGAGTCAGG    1260

ATCTCACTCT GTCACCTAGG CTGCACTGCA GTGCTATCAC AACTCAACTG CAGCTTCGAC    1320

CTTCTGGGCT CAAGTGAGCC ACCTCAGTCT CCCGAGTAGC TGGGACTATA GGTGCAGGCT    1380

GCCATGCCCG GCTAATTTTT TTATTTTTGT AGAGATGGTG ATTCACCATG TTGCCCAGGC    1440

TGGTCTCGAA CTCCTGGGCT CAAGCAATAT GCCCGCTTCG GCCTTCCAAA ATGTTGGGAT    1500

TACAGGCGTG AGCCACCATG CCGAGCTGAG GATCACTTGT TTTAACTGCT GGGAATCTCC    1560

CTTCGTTGGG CCTGGCTGTC GGGAAACCTG GGTCACAAGC ATGACCCTTC CCCGTCCCCC    1620

CTCACCCCAG ATGAGAACGG GATTCCCAGT AGTCCCCAGA AAGTAGCTCT GACCCTGGAT    1680

CTTGACCTGG AGAAGGAGCC GGAATCAGAG CCAGATGAGC CCCAGAAGCC AGGAAAAACCT    1740

TCAGTCTTCA CTGTCTTCCA GAAGATCTGG CTGACAGCGC TGTGCCTTGT GTTGGTCTTC    1800

ACAGTCACCC TGTCCGTCTT CCCCGCCATC ACAGCCATGG TGACCAG                  1847
```

(2) INFORMATION FOR SEQ ID NO:10:

(i) SEQUENCE CHARACTERISTICS:
        (A) LENGTH: 2396 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (xi) SEQUENCE DESCRIPTION: SEQ ID NO:10:

```
GCACTTTTGG GAGGCCAAGG GCAAGAGAAT CGCTTGAGCT CAGGAGTTCA AAACCAGCCT      60
TGGGCAACAC AGTGAGACTT TGTCTGTACA CACACACACA CACACAAATT TTTAATGAAG     120
AAAATAGAGG CCGGGTATGG TGGCTCACGC CTGTAATCCC AGCACTTTGG GAGGCTGAGG     180
CAGGTGGATC ACTCGAGGTC AGAAGTTCGA GACCAGCCTG GCCAACATGA TGAAACCTGG     240
CTCTACTAAA AATACAAAAA TTATCTGGGC ATGGTGGTGG CGGGCGCCTA TAGTCCCAGC     300
TACTCAGGAG GCTGAAGCAG GAGGATTTCT TGAACCCAGG AGGTGGAGGT TGCAGTGAGC     360
TGAGATCAGG GCCACTGCAC TCCAGCCTGG GCAACAGAGC GAGACTCCAT CTAAAAAAAA     420
AAAAAAAAAG TACTCTATGG GTGTCCTGAG ATGCCCTGGA GCAGAGACCT GGCTCCAGGG     480
ACCATGCTGA CTTCAGCCTC TACCACAGCC AGACGAGGAC AGCCGGCTGC TGCCCCTGCT     540
GGTCTGCCTG CGGTTCCTGT TCGTGCCCCT CTTCATGCTG TGCCACGTGC CCAGAGGTC     600
CCGGCTGCCC ATCCTCTTCC CACAGGATGC CTACTTCATC ACCTTCATGC TGCTCTTTGC     660
CGTTTCTAAT GGCTACCTGG TGTCCCTCAC CATGTGCCTG GCGCCCAGGT CCGGGCAATG     720
GGTGGGTGGG GGGCTGGATT AGGAGGTGGT TTATCTTNGG GAAGGACCGC TGCAATGGAG     780
GGACGGCCAT CCTGTTCTGG CCAGCCCAAC CTAGCTGTCT GCAGCCTTGC TGGCGCCCCN     840
TACTGGCCAA GCTTAACTGC AGGGGAGAGA ACTGGGTAGG GAGGTACCCG CCCAACCAAG     900
TAGCCCAGGC ACTGGTTCTG GGCCGCCTCA ATGTGCNTCA GTTTCCCCAT CTGTAAAAAA     960
AAAAATGGGT TGAACTGTCA TCCCTCAGGG CCCATCTAAC TGTAAAATTC TCAGTTGAAG    1020
GAGAGCTAAG GTTTTGACCA AAAACAAGGT CATGGGCTAT TTCCTCAAGG GGCAATGGAG    1080
TGGAGAATCC AGAGAGAATG AAGCTGGCAG GGCAGACAGG CTGAGAGCAC TGTGGAAAGG    1140
GCAGGCTGTG GAATCTGGAA TCCCATCATG TTAGACTCAG AGGCCCTGAG AGACATCCTT    1200
ATCCAGCAGC TCATTTACA GACCAGGAAA CTGAGGCCCA GAAAGAAGGG GCCAGTTATG    1260
GTGACAGAGG GGTTGGGTCA GAGCCCAGAC TGGATGGGCA GAGGGCAGTG GAGCTGGGTC    1320
CAGATTTAGA CCCAGCATTT TCTAAGAGCT CCTGTTCCCG GGTGTTTTAG GCAGGTGCTG    1380
CCACACGAGA GGGAGGTGGC CGGCGCCCTC ATGACCTTCT TCCTGGCCCT GGGACTTTCC    1440
TGTGGAGCCT CCCTCTCCTT CCTCTTCAAG GCGCTGCTCT GAAGTGGCCC CTCCAGGCTC    1500
TTTGGCAGCC TCTTCTCGAC GTCTCCTTCC GGAGCTGAGA TCCAGCCCAG GGCGAATGGC    1560
GAGCTTGGCT CAGGCCTCTG CGGGGTGGAG GCCCCTGGGC CTGAGGCTGC CAGCAGCGGG    1620
CAGGAGCTGC TCTTCATCCA CTTGGAGTGC TGCGGGAAG AAATCACCAC CGGTCATTCT    1680
AACCCTCACC CAGGAATGGG GGTGACTCGC ACAAGACCTC ATGGAAAGGG TGATGACTAG    1740
GGAAAAGAGG GTGCAGGGCA CGGCTGCTCC CCACCACCAG GTCTGCATTT GTTCATCATC    1800
ATCAGGAGCA GAGGTGACCA GAGGGTTCAG AGTGGGAGGC AGGGCCAGCC CAGGCCAGGA    1860
GCGCCTCATC TTCCCAGGCC TCAGCCACCC AGGGTAAAAG GTGCCAGGGA AGTTGTGGGC    1920
ACCTGAGAGG AGGAACAGAT GTGGAGGACC TGAGGGTGCT CAAAGGGCCA GGCTCAGCCT    1980
CAAGCAGTGT TTTCATTGCC AACACTTACT GTACCCACTC CGCAGAGCCC CGCTGGGCCT    2040
GGGCCCCAGG GCCACAGCTA GCCTGCATGT GTGTACTGCA CTTTACAGTT TGCAAAGCTC    2100
TTCCATACCC ACTCTCTCAC CGAAGCCTAA TTGAGGCTCT TGGAAGGAGT CAGGCAAGGA    2160
TTGTGCTTCC CCCATTATAC AGGTGACAAA ACTGAGTCCT GGGGAAAGTG ACTGGTCCGT    2220
```

```
GGTAGAGCCG GGACCCAATC CCCTCTCTCT CCTCCCTGTT GGTGCTGTTC TTCCTGCCCA      2280

ACACCTGTTT CTCTTTTCCT CAAGGGGTTT GGGGCAGGAG CCTGGGCACT TACTCCCCGT      2340

TTTTGCTGTT TCTCCTTCTG ACCCTGCTCT TGGGTCTAAT AACCCCATTT ATTTGT          2396
```

(2) INFORMATION FOR SEQ ID NO:11:

(i) SEQUENCE CHARACTERISTICS:
        (A) LENGTH: 237 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "intron 1"

(iii) HYPOTHETICAL: NO (xi) SEQUENCE DESCRIPTION: SEQ ID NO:11:

```
GTGAGTGGGC CGGGTGCGT TGCAAGTGGC CGGGGGCGTT GCAGACCCGC TCCCTGAAGG        60

CGCTCCGAGG CTCAGAGAAG ACCGGATCGA ACTACAATTC CCATCAGCCG ACTCCCTCGG      120

CCGCCGGAAC CGGGGTGATG GGGGTTGTAG TCCGCTCCGG AGGGGTGGC CTGGGAGGCG       180

GGAGGGCCTG CGGAGGCGGG TGCGTCCTCG GGGTGACCTT CCCACCGATC CCCACAG        237
```

(2) INFORMATION FOR SEQ ID NO:12:

(i) SEQUENCE CHARACTERISTICS:
        (A) LENGTH: 1712 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "intron 2"

(iii) HYPOTHETICAL: NO (xi) SEQUENCE DESCRIPTION: SEQ ID NO:12:

```
GTGAGACTCC TGGCGGCGTG GCAGCCTCGT GGCCACAGCC AGCACCCCTC CCTCCAGCCC       60

TTTGGATGAA GCTTAGCGGG CGCTTCCTCA CCGCGCACCT GTGACCCCTC GTTGAGCTCA      120

TTATGGGCTG AAGCTCGGAG AGGGGAATGC TTCCCCCGTG GCTAGGAAAG TAGAACTTCA      180

GCAATGCCCA CATCTCAGAG GGGCAAGGCC ACCAGCCCAC AGGGTCTGGA ATGAGCAAAG      240

GCGCTGCCAC CCCTCTCTGT GTGTCGTTAT TCCTGAGTCA GTCACCCCAA AAGTCGGTTA      300

TCGAACGTTT GATTTTCTTT GAAATACCAT GAATTTCATT CATTCACTCA TTCATTCAAC      360

AAACTTTTTT TTTTTTTTTT TTTTTGAGAC AGAGTCTGGC TCTTTCGCCC AGGCTGGAGT      420

GCAGTGGCGC CATCTCGGCT CACTGCAAGC TCCGCCTCCC GGGTTCACGC CATTCTCCTG      480

CCTCACCCTC CCGAGTAGCT GGGACTACAG GCGCCCGCCG CCACGCGCGG CTATTTTTTT      540

TTGTATTTTT AGTAGAGACG GGGTTTCACC GTGTTAGCCA GGATGGTCTC GATCTCCTGA      600

CCTCGTGATC CTCCCGCCTC GGCCTCCCAA AGTGCTGGGA TTACAGGCGT GAGCCACCGT      660

GCCCAGCCTC ATTCAACAAA CTTTTAGTGT GCATCTACTG TGGAGCAGGC ACTGGGGACA      720

CAGGAGGAAA CAGCAGGGAG GCTCTTCAGG GAAGGCAGAA ATGTGGGGTT TGCATTGTCT      780

TTGGGACCGG GTTATTCATC TGTATTCACT GCAACAACTT TGCAAATGCT TCTTGGGTAC      840

TGGCTCTGTG CTGGGCCCTG GAAACCCAGA GATGAATCAG CCCCTGGGCT TGAGAGCAAG      900

AAGGGGCCAA AGAGCTATTA ATAATGTAAC ATGATGCGTG ACATTCCAGG CTTGCAGCAG      960

AGTGCAGTGG GTCCCCAGGG AAGGAGAAAG TTCCTTCTGC TTCATGGAAG AGGAGATTTG     1020
```

```
TAAATTGGGA GTAGGGTAGG CAAAGTGCGT GTGGAGGGGT GTGGTCAGTA GGGCATTCCA    1080

AGCCGAGGCG ACAGCCATGC CAAAGGCAGG CAGGCAAGAG ACGATCAGCC TGTTTAGAGG    1140

GAGATTCCAC AGCCAGGGCT GCCTGGAGCT TAGCAGGATG GAGCAGAAGA TGGGGCACAA    1200

AGGGAGACTA GGATCTGATT CTGAAGAGCT GTTCCATTTG GGGCTTTGCC CTGCAGGCAA    1260

TAGGGAGGCA TGAATCGGGG TGTTGAGGAG TGAGGAGGTT AAGCAGAGGA GTGGCAGGCT    1320

ATGTGCTCTA GAGAGAATGC AGTTGTTCAG CACTTAGGCC AAAGCCTGGC TTGACAGTAG    1380

GCGCTCAATA AATACCCGTG GAATGAATGA ATGTAGCAGC TGCTGCAGGA GTGGGGATGG    1440

GGGCTGGAAC CAGGGCACTG AAGAGGAGGG GCCGTCCAAG GCTGGATCGA GGCTCTTGCT    1500

GGGGGCTCTT AATGCTTAGG CTGTGTCCCA GACTTCAGCC ATTTAACTCA GCACACATTC    1560

ATGGAGCTCC GACTGTGTGC CGGCTGCTGG GAACAGAACA AGGGCAAGGC AGACAAGTCC    1620

CCACAGACAT TAGAAAGCAA TCACAAGTGA GGGGGAAGGC AGCGGGGAA GGCTGAGAGG     1680

TGCTGACCCT CCACCACCTC CCTACCTGGC AG                                  1712
```

(2) INFORMATION FOR SEQ ID NO:13:

(i) SEQUENCE CHARACTERISTICS:
        (A) LENGTH: 170 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "intron 3"

(iii) HYPOTHETICAL: NO (xi) SEQUENCE DESCRIPTION: SEQ ID NO:13:

```
GTGAGAGGCC TGCCCTGGCT CCTGCGCCCT CTGCCGAGGC AGCTTCATTG AGGCCCTCCC      60

CTGCGCCCCC TGCCCTCCAG CCCTACTGCC CAGCCCCAGG TGTCGAGCCT CCTTCCCCAG     120

CCCCCTCTGG CCTGGGCCCC ACTGATGCAC TCTGCCTGCT TCTGAGCAAG               170
```

(2) INFORMATION FOR SEQ ID NO:14:

(i) SEQUENCE CHARACTERISTICS:
        (A) LENGTH: 388 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "intron 4"

(iii) HYPOTHETICAL: NO (xi) SEQUENCE DESCRIPTION: SEQ ID NO:14:

```
GTGAGCACCT CCACCCCCTC TCCAGCCAGC CTATGCAGGG CTTCAGCCTG GCCTCATCAT      60

TGAAAGGGCC CAGCATATCC GAGAAGGGCA GACAGCATCA TGGTCGCTCA TATCCCTGGT    120

GAAGAAACTG AGGCCCACAG GGAGGGGAAG AGTCACTTGT CCGGTGACCT AGGAGCAGGC    180

CTCCTGGTCA ACAGCCCCAC AGACCAATGG CTGCACCTCA GAAGAGGACT GAATAGCGGG    240

TGTTGCCCCC GAGTGCTCAG AGTCCCTAGG GAAGCTCACA CCTGCGCAAC CTTGTCCAGA    300

GTCCCCTGTG TATCCTGCCG GCACCTCCTC CAGGGAGCCT CTGAGTCTTG CCTAGTTGAG    360

CAGCAGCCCC CATCCCTGTC CTCCACAG                                       388
```

(2) INFORMATION FOR SEQ ID NO:15:

(i) SEQUENCE CHARACTERISTICS:
    (A) LENGTH: 667 base pairs
    (B) TYPE: nucleic acid
    (C) STRANDEDNESS: double
    (D) TOPOLOGY: linear (ii) MOLECULE TYPE: other nucleic acid
    (A) DESCRIPTION: /desc = "intron 5"

(iii) HYPOTHETICAL: NO (xi) SEQUENCE DESCRIPTION: SEQ ID NO:15:

```
GTGAGTGCAC TTGGGTGGCT GGGAGGGCTG GGGTGGCCTC TGAGGTTTGG GGAAGAGAGA      60
GGGCATGTGA GAGCAAGACA CATGGGTTCT GGGTGAAGAT GGAGGTAAGC GGGTGATATG     120
GAAATGGGGA TTGGTCTGGG GCTAGGGAAT GGGGCTCATG GGCCCTGCAG TGAGGAGTAA     180
TAACCAAGTG AGGACTGGGT TAACTCAGGG ACAGGGCAG  GATTCCTGGG GCTAATACTG     240
GCATGTGGCA GCAGGTTGAA GTTGAAGGAT AAGGGGATGG GTTTGGGATT CAGATAGTCT     300
TGGGTTTGAA TCTGCTTCAC CGCTTACCAG CTAGGGGTGT TGGACAAGGC TTGTCACCTC     360
TCTGTGCTAG CTTCCCCACC GATGTGATTG GTACAGCTCC CTGCTCAGAT TGTAATGAGC     420
ATGCAATGAG AGAAGGCTAC TGGCACATAG TACGTGCTCA ACAAAAATGA CACATGGGGA     480
AAGTGAGAGA AGTGCAGGGC TGCTCTGGGG CCCTGTACAA GATTCCCATT TGTCAGTGAA     540
GGGAGGAGCG GAAGAGGCTG GGAGTGGGTC TGAGAAGTAC ACAATGGGAA GTGGGACAAG     600
AGTTGGAAGC CCCGTGGGAG CCGGCGGGAC CAGGTGCCTC TCTTCTGCAG CTGAAGTTCC     660
TCCGCAG                                                                667
```

(2) INFORMATION FOR SEQ ID NO:16:

(i) SEQUENCE CHARACTERISTICS:
        (A) LENGTH: 223 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "intron 6"

(iii) HYPOTHETICAL: NO (xi) SEQUENCE DESCRIPTION: SEQ ID NO:16:

```
GTGAGCCTGC TGTTGGGCTC GAGGCCCCAC CTCAAAGCAT CTTGGATAGA GTCCTGAGCC      60
TGAAGCCCTG AGAGAGGCCA GGGGAGGTGG AGGAGACCTG GTCTCAGCCC TGACCCCCAG     120
AGAAGACACT GAGGGGCCCC AGCCTCCAGG CCAATGGTAT GGGGAGGGAT CCAGACACCT     180
CAGGCAAGCC AGGCAGGCCC AACACTTTCC TGTCCTTCTG CAG                       223
```

(2) INFORMATION FOR SEQ ID NO:17:

(i) SEQUENCE CHARACTERISTICS:
        (A) LENGTH: 897 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "intron 7"

(iii) HYPOTHETICAL: NO (xi) SEQUENCE DESCRIPTION: SEQ ID NO:17:

```
GTAAGCCCTG AGACCCTCCT GGGGAGGTGG GAGATGCAGA GGAAGCTAGA GCCACCTCCC      60
```

```
CTGGGAAGCT GTTCCATCTG TTCCCAGCCA GAGCCCACCC CTAGTAGCCT TGTGCAAACA      120

GGAAGATCAT GAAGGGAAGT TGGTAGGATT AAAGTCATCC CTGCTGTTGT TTGGGCCTCA      180

GTTTCCACCT CTATAAAATG GGGAGGCGAC AGAAGTTCCA TGCATGCAAA CTTTGGATCG      240

AAGACCTCTG AATTGGAATA CTAGTTTCAC AACATCCCRG CTGTGTGGCC TGAGACAAAC      300

CACTTAGCCA CTGCACCCCT CTGAACCTCA ATGTGTCATT TGTAAAGCAA TGGTAATGAG      360

ATAATCCATC TAAGGTGCTT CGCTCATCAC CCGACCCATG CACGCGCTTC TGGTAGCTAT      420

GCATATTTCC ATCATGAATT CCCTTCGCCT GCAGCCTCAG CTTAGGCTGG AGGAAGATCA      480

CCTTTTTTTG TTTTGGGGTG AGGGGGTTGT TGTTATTTTG AGTCAGGATC TCACTCTGTC      540

ACCTAGGCTG CACTGCAGTG CTATCACAAC TCAACTGCAG CTTCGACCTT CTGGGCTCAA      600

GTGAGCCACC TCAGTCTCCC GAGTAGCTGG GACTATAGGT GCAGGCTGCC ATGCCCGGCT      660

AATTTTTTTA TTTTTGTAGA GATGGTGATT CACCATGTTG CCCAGGCTGG TCTCGAACTC      720

CTGGGCTCAA GCAATATGCC CGCTTCGGCC TTCCAAAATG TTGGGATTAC AGGCGTGAGC      780

CACCATGCCG AGCTGAGGAT CACTTGTTTT AACTGCTGGG AATCTCCCTT CGTTGGGCCT      840

GGCTGTCGGG AAACCTGGGT CACAAGCATG ACCCTTCCCC GTCCCCCTC ACCCCAG         897
```

(2) INFORMATION FOR SEQ ID NO:18:

(i) SEQUENCE CHARACTERISTICS:
        (A) LENGTH: 199 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "intron 8"

(iii) HYPOTHETICAL: NO (xi) SEQUENCE DESCRIPTION: SEQ ID NO:18:

```
GTTTGGCTTG GATACAGCCC CCAACCACCA TCTTTGGGGA AGAATGGGGC TCACATTGAC       60

TCCAAGGTCA TAGGGTCACA GTGGGTCAGG GACACAGCTG GGCCAGGCCC CAAGTGTCCT      120

GCTCCCACAT GGGGCTTGGG CAAGAGGGTG GGGCCCTGGG ACTGCCCTGC CTGCTCACAC      180

CCCTGCCTCY GGCTCCCAG                                                  199
```

(2) INFORMATION FOR SEQ ID NO:19:

(i) SEQUENCE CHARACTERISTICS:
        (A) LENGTH: 104 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "intron 9"

(iii) HYPOTHETICAL: NO (xi) SEQUENCE DESCRIPTION: SEQ ID NO:19:

```
GTGAGTGTCA GGGTGGAGAA GACGGCAGGG CAGGGGGTAC AAAGGGGAGA GGACGGGAGA       60

GGGGAGTTGG AGACCAGTAT GAGCTGCAGC CGTTTCCCTC CCAG                      104
```

(2) INFORMATION FOR SEQ ID NO:20:

(i) SEQUENCE CHARACTERISTICS:
        (A) LENGTH: 461 base pairs
        (B) TYPE: nucleic acid

```
        (C) STRANDEDNESS: double
        (D) TOPOLOGY: linear (ii) MOLECULE TYPE: other nucleic acid
         (A) DESCRIPTION: /desc = "intron 10(5')"

(iii) HYPOTHETICAL: NO (xi) SEQUENCE DESCRIPTION: SEQ ID NO:20:

GTAAGCACAC CAGGGCTGGG TGATCCGATG TTTTAGGAAG CAGTTTGGGA TCCGAGGGCT      60

TGAAAGAGCA CGGAGGTGAT TTTCTGGTAG TCCAAGTGGC CTGGTAATGC AACCACTGGC     120

CAAGCAGCAG GGAGCACTTG GCCCTGGAG GCGTGCAAGG CCAGGGCTTG CACTGTGAGC      180

TCCCTGAAAG CAAAAATCAT GTCCAGCTGA CCTCTGTGTC CCCAGCATCC AGCCTTTGCT    240

GCTCAGAGAA TGTTACATGG AGGTTCCTGC ACCAGGTGAG GGACTGAGCA AGATCTTAGT    300

TTTGGGGTTG GTTTTAGCCA TGGTGCTGTA TCTTTAAATG AAATCTTCCA AAGAGACAAT    360

ACATAACGCA GGTGAAAGAN GANCTGGTCT CATCCAAGTC AGGACANNGA GCTGATCTAC    420

AGCTTCCAAT CCCACTCAGA AACCCTCTGC CCCCAANGGG G                        461

(2) INFORMATION FOR SEQ ID NO:21:

(i) SEQUENCE CHARACTERISTICS:
         (A) LENGTH: 508 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "intron 10(3')"

(iii) HYPOTHETICAL: NO (xi) SEQUENCE DESCRIPTION: SEQ ID NO:21:

GCACTTTTGG GAGGCCAAGG GCAAGAGAAT CGCTTGAGCT CAGGAGTTCA AAACCAGCCT     60

TGGGCAACAC AGTGAGACTT TGTCTGTACA CACACACACA CACACAAATT TTTAATGAAG    120

AAAATAGAGG CCGGGTATGG TGGCTCACGC CTGTAATCCC AGCACTTTGG GAGGCTGAGG    180

CAGGTGGATC ACTCGAGGTC AGAAGTTCGA GACCAGCCTG GCCAACATGA TGAAACCTGG    240

CTCTACTAAA AATACAAAAA TTATCTGGGC ATGGTGGTGG CGGGCGCCTA TAGTCCCAGC    300

TACTCAGGAG GCTGAAGCAG GAGGATTTCT TGAACCCAGG AGGTGGAGGT TGCAGTGAGC    360

TGAGATCAGG GCCACTGCAC TCCAGCCTGG GCAACAGAGC GAGACTCCAT CTAAAAAAAA   420

AAAAAAAAAG TACTCTATGG GTGTCCTGAG ATGCCCTGGA GCAGAGACCT GGCTCCAGGG    480

ACCATGCTGA CTTCAGCCTC TACCACAG                                      508

(2) INFORMATION FOR SEQ ID NO:22:

(i) SEQUENCE CHARACTERISTICS:
         (A) LENGTH: 662 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "intron 11"

(iii) HYPOTHETICAL: NO (xi) SEQUENCE DESCRIPTION: SEQ ID NO:22:

GTCCGGGCAA TGGGTGGGTG GGGGGCTGGA TTAGGAGGTG GTTTATCTTN GGGAAGGACC     60

GCTGCAATGG AGGGACGGCC ATCCTGTTCT GGCCAGCCCA ACCTAGCTGT CTGCAGCCTT    120
```

```
                                          -continued

GCTGGCGCCC CNTACTGGCC AAGCTTAACT GCAGGGGAGA GAACTGGGTA GGGAGGTACC      180

CGCCCAACCA AGTAGCCCAG GCACTGGTTC TGGGCCGCCT CAATGTGCNT CAGTTTCCCC      240

ATCTGTAAAA AAAAAAATGG GTTGAACTGT CATCCCTCAG GGCCCATCTA ACTGTAAAAT      300

TCTCAGTTGA AGGAGAGCTA AGGTTTTGAC CAAAAACAAG GTCATGGGCT ATTTCCTCAA      360

GGGGCAATGG AGTGGAGAAT CCAGAGAGAA TGAAGCTGGC AGGGCAGACA GGCTGAGAGC      420

ACTGTGGAAA GGGCAGGCTG TGGAATCTGG AATCCCATCA TGTTAGACTC AGAGGCCCTG      480

AGAGACATCC TTATCCAGCA GCCTCATTTA CAGACCAGGA AACTGAGGCC CAGAAAGAAG      540

GGGCCAGTTA TGGTGACAGA GGGGTTGGGT CAGAGCCCAG ACTGGATGGG CAGAGGGCAG      600

TGGAGCTGGG TCCAGATTTA GACCCAGCAT TTTCTAAGAG CTCCTGTTCC CGGGTGTTTT      660

AG                                                                    662
```

NITROBENZYLMERCAPTOPURINERIBOSIDE (NBMPR)-INSENSITIVE, EQUILIBRATIVE, NUCLEOSIDE TRANSPORT PROTEIN, NUCLEIC ACIDS ENCODING THE SAME AND METHODS OF USE

CROSS-REFERENCE TO RELATED APPLICATIONS

The present Application is a Divisional Application of U.S. Ser. No: 09/058,389 filed on Apr. 9, 1998, now U.S. Pat. No. 6,130,065, which is a non-provisional application claiming the priority of provisional U.S. Ser. No. 60/043,659 filed on Apr. 11, 1997. Applicants claim the benefits of these Applications under 35 U.S.C. §§119(e) and 120. The contents of U.S. Ser. No: 09/058,389 filed on Apr. 9, 1998 is hereby incorporated by reference in its entirety.

RESEARCH SUPPORT

The research leading to the present invention was supported in part by R01-CA55056 and Cancer Center CORE Support grant P30-CA21765 from the National Cancer Institute. The government may have certain rights in the present invention. Support for this invention was also provided by the AMERICAN LEBANESE SYRIAN ASSOCIATED CHARITIES.

FIELD OF THE IVENTION

The invention relates generally to the equilibrative transport of nucleosides into cells, and more particularly to nitrobenzylmercaptopurineriboside (NBMPR)-insensitive, equilibrative, nucleoside transport proteins (iENTPs), to nucleic acids which encode the proteins, methods of use of the proteins and nucleic acids, and antibodies to the proteins.

BACKGROUND OF THE INVENTION

Aside from being potential precursors to the building blocks of nucleic acids, the natural nucleosides are important metabolites having many physiological effects in assorted organs. For example, adenosine and its corresponding nucleotides are local signaling molecules that act through purinergic receptors to affect such varied physiological functions as lipolysis, neurotransmitter release, coronary vasodilation, cardiac contractility, renal vasoconstriction, and bronchial constriction; and thus extracellular adenosine concentrations can have significant effects on cardiac and vascular functions as well as play a role in neuromodulation [reviewed by Griffith et al. Biochim. Biophys. Acta Rev. Biomembr., 1286:153–181 (1996); Cass, in *Drug Transport in Antimicrobial Therapy and Anticancer Therapy* (N. H. Georgopapadakou, ed.(Marcel Dekker)), 403–451 (1995)]. In addition, nucleoside analogs are presently employed as anti-retroviral drugs, and as anticancer drugs. Although some extracellular nucleosides can passively permeate the plasma membrane, most participate in some form of protein mediated transport performed by nucleoside transport proteins. Nucleoside transport proteins play an important role in the uptake and efflux of physiological nucleosides used in DNA and RNA synthesis, lipid and glycogen metabolism, and glycoprotein and glycolipid synthesis. Furthermore nucleoside transport proteins mediate the uptake and efflux of a number of antitumor and antiviral nucleoside analogs in cells [Cass, 1995, supra]. Nucleoside transport inhibitors are currently being investigated as modulators of adenosine action in cerebral and cardiac ischemia to provide protection from reperfusion injury [Rongen et al., *J. Clin. Invest.* 95:658–668 (1995); Parkinson et al., *Gen. Pharmacol.* 25:1053–1058 (1994)].

The first nucleoside transporters studied functioned as facilitated diffusion systems. Such equilibrative nucleoside transport proteins were initially classified solely by their sensitivity to nitrobenzylmercaptopurineriboside (NBMPR). As the study of these proteins progressed, additional characteristics such as permeant selectivity and tissue distribution have been used to further distinguish these proteins [Griffith and Jarvis, *Biochim. Biophys. Acta Rev. Biomembr.*, 1286:153–181(1996)]. More recently, sodium-dependent concentrative nucleoside transport proteins have also been identified.

At least five distinct nucleoside transport activities have been identified that differ in their permeant selectivity, sensitivity to inhibitors and distribution in normal tissues and tumors [Griffith and Jarvis, 1996, supra]. Two of these activities exhibit equilibrative mechanisms that mediate both the influx and efflux of nucleosides across the plasma membrane, while the other three activities exhibit concentrative, sodium-dependent mechanisms that under physiological conditions mediate only the influx of nucleosides.

The major equilibrative carrier in most cells, es (equilibrative, sensitive) is highly sensitive to the inhibitor NBMPR, having $IC_{50}$ values of 0.1 to 1 nM. A human homolog of this protein (hENT1) has recently been cloned (Griffiths et al., Nature Med. 3:89–93 (1997). It has 10 to 11 predicted membrane spanning regions and has some structural similarities to the equilibrative glucose carriers. It does not however, share sequence homology with the glucose transporter family and appears to represent a new family of membrane transport proteins designated ENT for equilibrative nucleoside transporter.

Many cells also contain a second equilibrative transporter ei (equilibrative, insensitive) that is insensitive to nanomolar concentrations of NBMPR, but can be inhibited by higher ($\mu$M) concentrations [Belt, *Mol. Pharmacol.*, 24:479–484 (1983); Plagemann and Wohlheuter, *Biochim. Biophys. Acta*, 773:39–52 (1984)]. This protein, an NBMPR-insensitive equilibrative nucleoside transport protein (iENTP) has remained elusive. Both of the equilibrative transporters accept a broad range of physiological nucleosides and their cytotoxic and antiviral analogs as permeants, although there appear to be differences in their affinity for some nucleosides [Griffith and Jarvis, 1996, supra].

iENTPs also are present in most tumor cells, although the level of iENTP appears to be variable. The concentration of iENT in a particular tumor cell is likely to be a major determinant in the ability of that cell to grow following the administration of an es transport inhibitor to block the nucleoside salvage pathway, together with an inhibitor of de novo nucleoside synthesis, such as trimetrexate, methotrexate, and tomudex. The level of iENTP in a tumor cell is also likely to be a determinant of the success of using es inhibitors to block the efflux of cytotoxic and antiviral nucleoside analogs from cells. Under such circumstances, cells with higher concentrations of iENTP will have a higher efflux of cytotoxic and antiviral nucleoside analogs, unless an inhibitor of the iENTP is also administered.

NBMPR and its congeners are the most specific and potent inhibitors of the es transporter currently available. The.es transporter has a high-affinity binding site for NBMPR that overlaps at least in part with the substrate binding site [Jarvis, in *Adenosine Receptors*, D. M. F. Cooper and C. Londos, eds., (New York: Alan R. Liss, Inc.), pp. 113–123 (1988)]. NBMPR binds to this site with a dissociation constant of 0.1 to 1 nM and completely inhibits nucleoside uptake via es at concentrations in the nanomolar range [Paterson and Cass, in *Membrane Transport of Antineoplastic Agents*, I. D. Goldman, ed., (New York: Pergamon Press), pp. 309–329 (1986); Gati and Paterson, in *The red cell membrane: structure, function, and clinical implications*, P. Agre and J. C. Parker, eds., (New York: Marcel Decker), pp. 635–661 (1989); Jarvis, 1988, supra; Plagemann et al., *Biochim. Biophys. Acta.*, 969:1–8 (1988)]. At high concentrations (>1 uM), however, NBMPR also inhibits the ei transporter [Paterson et al., *Mol. Parmacol.*, 18:40–44 (1980); Belt, *Mol. Pharmacol.*, 24:479–484 (1983); Plagemann and Wohiheuter, *Biochim. Biophys. Acta.*, 773:39–52 (1984)].

Dipyridamole also binds to the NBMPR-binding site of es [Jarvis, *Mol. Pharmacol.*, 30:659–665 (1986)], but is a less potent inhibitor of es than NBMPR [Plagemann and Wohlheuter, *Curr. Topics Membr. Trans.*, 14:225–330 (1980); Paterson and Cass, 1986, supra; Plagemann and Woffedin, *Biochim. Biophys. Acta.*, 969:1–8 (1988)].

Dipyridamole also inhibits the ei transporter, but its potency against this transporter has been unclear. It has been suggested that the es transporter and the ei transporter are equally sensitive to dipyridamole since the curves for inhibition of nucleoside transport are monophasic in cells that possess both transporters [Jarvis, 1988, supra; Plagemann et al., 1988, supra]. However, recent studies with Ehrlich ascites tumor cells in which the es transporter was blocked by addition of low concentrations of NBMPR, suggest that the ei transporter is significantly less sensitive to dipyridamole than es [Hammond, *J. Pharmacol. Exp. Ther.*, 259:799–807 (1991)].

In addition to the two equilibrative nucleoside transporters there are at least three $Na^+$-dependent, concentrative nucleoside transport activities that differ from each other, and from the equilibrative transporters, in their substrate specificity. Two of these, cif and cit (also called N1 and N2), exhibit selectivity for purine and pyrimidine nucleosides respectively [Vijayalakshmi et al., *J. Biol. Chem.*, 263:19419–19423 (1988) and Williams et al., *Biochem. J.*, 264:223–231 (1991)]; while the third, cib (also called N3), has a broader selectivity accepting both purine and pyrimidine nucleosides [Wu et al., *J. Biol. Chem.*, 267:8813–8818 (1992); Huang et al., *J. Biol. Chem.*, 268:20613–20620 (1993)]. All three of the concentrative nucleoside transporters are insensitive to NBMPR and dipyridamole at concentrations up to 10 $\mu$M; and under physiological conditions mediate only the influx of nucleoside into cells. These concentrative transport activities have been observed predominantly in normal tissues such as kidney [Le Hir and Dubach et al., Pflugers Arch., 401:58–63 (1984); Williams et al., Biochem. J., 264:223–231 (1989); Williams et al., *Biochem. J.*, 274:27–33 (1991); Le Hir et al., *Pflugers Arch.*, 401:58–63 (1990)] and intestine Schwenk et al., *Biochim. Biophys. Acta.*, 805:370–374 (1984); Vijayalakshtni et al., *J. Biol. Chem.*, 263:19419–19423 (1988); Williams et al., *Biochem. J.*, 274:27–33 (1991), and appear to be the major nucleoside transport activity in the specialized epithelial cells of these tissues [Williams et al., *Biochem. J.*, 274:27–33 (1989); Vijayalakshmi et al., *J Biol. Chem.*, 263:19419–19423 (1988)]. However, low levels of $Na^+$-dependent nucleoside transport have been observed in some tumor cells lines (Lee et al., *Biochem. J.*, 274:85–90 (1991); Belt et al., *Mol Pharmacol.*, 24:479–484 (1993); Crawford et al.,*J. BioL Chem.*, 265:13730–13734 (1990b); Dagnino et al., *Cancer Res.*, 50:6549–6553 (1990)].

cDNA clones have recently been obtained for two of the concentrative nucleoside transporters. Cass and co-workers have cloned rCNT1 from rat intestine. This cDNA encodes a 71 Kd protein with cit-type transport activity in transient expression studies in Xenopus oocytes [Huang et al., J. Biol. Chem., 269:17757–17760 (1994)] and COS cells [Fang et al., Biochem. J., 317:457–465 (1996)]. The second transporter, rSPNT (rCNT2) was cloned from rat liver and encodes a 72 Kd protein that has cif-type transport activity in expression studies in Xenopus oocytes. The CNT1 and SPNT transporters are 64% identical in their deduced amino acid sequences, and have significant homology with the bacterial nupC nucleoside transporters. They do not, however, have significant homology with any known mammalian proteins, and thus represent a new family of mammalian membrane transporters. It should be noted that rCNT1 and rSPNT do not share homology with SNST [Pajor et al., *J. Biol. Chem.*, 267:3557–3560 (1992)], a member of the sodium-dependent glucose transporter family that has weak nucleoside transport activity when expressed in Xenopus oocytes. It is not yet known whether SNST represents a significant nucleoside transport activity in mammalian cells. The human homolog of CNTI has recently been cloned [Ritzel et al. *Am. J. Physiol.* (1997)].

The isolation and cloning of nucleoside transport proteins allows the biochemical characteristics of these transport proteins to be individually investigated and exploited. Such analysis is important for drug development, for example, in which drugs can be more readily designed to inhibit specific transport mechanisms. Unfortunately, heretofore, no NBMPR-insensitive equilibrative transport protein has been isolated or cloned, which has severely hampered analogous studies with this major class of nucleoside transporters.

The citation of any reference herein should not be deemed as an admission that such reference is available as prior art to the instant invention.

SUMMARY OF THE INVENTION

Nucleosides play a central role in cellular metabolism. The nucleoside salvage pathway is an important means employed by cells to maintain the requisite amount of these important metabolites. The initial step in the nucleoside salvage pathway is their transport across the plasma membrane. The key mode of transport of nucleosides into the cell is performed by nucleoside transport proteins contained in the plasma membranes. The present disclosure reports the first isolation and cloning of a cDNA encoding an NBMPR-insensitive equilibrative nucleoside transporter.

The present invention provides a purified transmembrane protein with nucleoside transport activity and the active fragments thereof. The transmembrane protein transports nucleosides across the plasma membrane through a facilitated diffusion process. More specifically, the transmembrane protein is an equilibrative nucleoside transport protein which is insensitive to nitrobenzylmercaptopurineriboside (NBMPR). In one embodiment the NBMPR insensitive, equilibrative nucleoside transport protein (iENTP) contains approximately 450 amino acid residues, and 8 to 12 putative transmembrane domains. In one such embodiment the iENTP is a vertebrate protein. In a preferred embodiment the iENTP is a mammalian protein. In a more preferred embodiment the iENTP is a human protein containing 456 amino acids and has 10 to 11 putative transmembrane domains.

One aspect of the present invention provides an isolated nucleic acid which encodes an iENTP of the present invention that includes exons and introns as shown in FIG. 6. In a preferred embodiment of this type, the isolated nucleic acid contains the nucleotide sequences of SEQ ID NO:5 and SEQ ID NO:10. The introns of the gene are individually part of the present invention,.having nucleotide sequences of SEQ ID NOs:11, 12, 13, 14, 15, 16, 17, 18, and 19 for introns 1–9 respectively. The 5' portion of intron 10 has the nucleotide sequence of SEQ ID NO:20 whereas the 3' portion of intron 10 has the nucleotide sequence of SEQ ID NO:21. Intron 11 has the nucleotide sequence of SEQ ID NO:22. Nucleic acid probes which hybridize to the isolated nucleic acid are also included in the present invention. In a preferred embodiment of this type, the nucleic acid probes hybridize to the untranslated portion of the nucleic acid.

The present invention further provides an isolated nucleic acid that contains a nucleotide sequence of the genomic 5' flanking region of a gene encoding an iENTP. In a preferred embodiment of this type, the isolated nucleic acid has the nucleotide sequence of SEQ ID NO:6. The present invention also includes nucleic acid probes which hybridize to the nucleic acid sequence of SEQ ID NO:6.

Another aspect of the present invention includes isolated nucleic acids encoding the iENTPs and active fragments thereof. One such isolated nucleic acid encodes an amino acid sequence of a transmembrane protein that functions as an equilibrative nucleoside transport protein that is insensitive to NBMPR. In a particular embodiment the nucleic acid encodes an iENTP that contains approximately 450 amino acid residues. In one embodiment of this type, the isolated nucleic acid has a nucleotide sequence with at least 80% similarity with the coding sequence of the human iENTP (hENT2), SEQ ID NO:1. In another embodiment of this type, the isolated nucleic acid has a nucleotide sequence with at least 80% identity with the coding sequence of the human iENTP (hENT2), SEQ ID NO:1. In still another embodiment the isolated nucleic acid has the nucleotide sequence of nucleotides 238–1605 of SEQ ID NO:1. In yet another embodiment of this aspect of the invention, an isolated nucleic acid encodes an iENTP having the amino acid sequence of hENT2, SEQ ID NO:2. In a related embodiment an isolated nucleic acid encodes SEQ ID NO:2 comprising one or more conservative substitutions thereof.

The iENTPs of the present invention, as well as the corresponding nucleic acids which encode them can be obtained from any natural source preferably from a vertebrate cell, more preferably from a mammalian cell, and most preferably from: a human cell.

The present invention also includes oligonucleotides that hybridize to the nucleic acids encoding the iENTIPs of the present invention. In one embodiment the oligonucleotide consists of at least 18 nucleotides. In a preferred embodiment, the oligonucleotide consists of at least 27 nucleotides. In a more preferred embodiment, the oligonucleotide consists of at least 36 nucleotides. Oligonucleotides of the present invention can be used as nucleic acid probes, PCR primers, antisense nucleic acids, and the like, including for diagnostic and therapeutic purposes.

In one such embodiment the oligonucleotide hybridizes to SEQ ID NO:1, or more particularly hybridizes to the coding sequence of SEQ ID NO:1. In a related embodiment the oligonucleotide hybridizes to the nucleotides 512–579 of SEQ ID NO:1. In one embodiment, the hybridization is performed under moderate stringency. In another embodiment, the hybridization is performed under standard hybridization conditions. In yet a third embodiment, the hybridization is performed under stringent hybridization conditions.

Isolated DNAs that encode the iENTPs of the present invention and active fragments thereof are also part of the present invention. In one embodiment, the nucleotide sequence of the DNA has at least 80% similarity with the coding sequence of SEQ ID NO:1. In another embodiment, the nucleotide sequence of the DNA has at least 80% identity with the coding sequence of SEQ ID NO:1. In still another embodiment the DNA has the nucleotide sequence of nucleotides 238–1605 of SEQ ID NO:1. In yet another embodiment the DNA encodes an iENTP having the amino acid sequence of SEQ ID NO:2. In a related embodiment the DNA encodes an amino acid sequence of SEQ ID NO:2 comprising one or more conservative substitutions thereof. In a particular embodiment the DNA is a recombinant DNA (cDNA).

In another embodiment, an isolated or recombinant nucleic acid (including a DNA) has at least 80% similarity with the coding sequence of SEQ ID NO:7. In another embodiment, the nucleotide sequence of the nucleic acid has at least 80% identity with the coding sequence of SEQ ID NO:7. In still another embodiment the nucleic acid contains the nucleotide sequence of SEQ ID NO:7. In yet another embodiment the nucleic acid encodes a protein containing the amino acid sequence of SEQ ID NO:8. In a related embodiment the nucleic acid encodes an amino acid sequence of SEQ ID NO:8 comprising one or more conservative substitutions thereof. In a particular embodiment the DNA is recombinant (cDNA).

All of the isolated nucleic acids and recombinant DNAs of the present invention can further comprise a heterologous nucleotide sequence. Such heterologous nucleotide sequences can encode, for example, a fusion peptide (e.g., a FLAG-tag) or a chimeric protein partner such as a fusion protein.

The present invention also includes DNA constructs comprising the isolated DNAs encoding the iENTPs of the present invention. In one such embodiment the DNA is operatively linked to an expression control sequence. In one embodiment the DNA is operatively linked to an expression control sequence and encodes the amino acid sequence of SEQ ID NO:2. In another embodiment the DNA is operatively linked to an expression control sequence and encodes the amino acid sequence of SEQ ID NO:2 comprising one or more conservative substitutions thereof. In a particular embodiment the DNA is a recombinant DNA (cDNA).

Also included in the present invention are transfected or transduced cells which are transfected or transduced with the recombinant DNA constructs of the present invention. The transfected or transduced cells can be either a prokaryotic cell, or a eukaryotic cell. In one such embodiment, the transfected cell is a COS cell. In another embodiment, the transduced cell is a hematopoietic stem cell. In a particular embodiment, the transfected cell is a human T-cell leukemia CEM cell. In a preferred embodiment the transfected or transduced cell is transfected or transduced with a DNA construct containing a DNA that is operatively linked to an expression control sequence and encodes the amino acid sequence of SEQ ID NO:2. In a related embodiment the transfected or transduced cell is transfected or transduced with a DNA construct containing a DNA that is operatively linked to an expression control sequence and encodes the amino acid sequence of SEQ ID NO:2 comprising one or more conservative substitutions thereof.

Another aspect of the present invention includes the isolated iENTPs of the present invention and active fragments thereof. In its broadest embodiment the isolated iENTP is a transmembrane protein that is NBMPR insensitive, and functions as an equilibrative nucleoside transport protein. In a particular embodiment, the iENTP has approximately 450 amino acids. In one embodiment the iENTP is encoded by a nucleotide sequence having at least 80% similarity with the coding sequence of SEQ ID NO:1. In another embodiment the iENTP is encoded by a nucleotide sequence having at least 80% identity with the coding sequence of SEQ ID NO:1. In still another embodiment the iENTP has an amino acid sequence of SEQ ID NO:2 comprising one or more conservative substitutions thereof. In a preferred embodiment the isolated iENTP has an amino acid sequence of SEQ ID NO:2.

In another embodiment the iENP is encoded by a nucleotide sequence having at least 80% similarity with the coding sequence of SEQ ID NO:7. In another embodiment the iENTP is encoded by a nucleotide sequence having at least 80% identity with the coding sequence of SEQ ID NO:7. In still another embodiment the IENT? has an amino acid sequence of SEQ ID NO:8 comprising one or more conservative substitutions thereof. In a preferred embodiment the isolated iENTP has an amino acid sequence of SEQ ID NO:8.

The present invention also includes modified iENTPs of the present invention, such as tagged proteins, labeled proteins, fusion proteins and the like. Such modified iENTPs may be used for example as antigens or for marker purposes. In a particular embodiment of this type, the fusion protein comprises an iENTP protein or active fragment thereof having an amino acid sequence of SEQ ID NO:2 or SEQ ID NO:2 comprising a conservative substitution thereof. In preferred embodiments the modified iENTP retains its activity as an NBMPR insensitive equilibrative nucleoside transport protein.

In a specific embodiment, an iENTP fusion protein can be expressed. An iENTP fusion protein comprises at least a functionally active portion of a non-iENTP protein joined via a peptide bond to at least a functionally active portion of an iENTP polypeptide. In a particular embodiment, an iENTP fusion protein or peptide contains an iENTP or fragment thereof and a FLAG-tag. In an alternative embodiment, an iENTP fusion protein or peptide contains an iENTP or fragment thereof and green fluorescent protein or derivatives thereof, as exemplified in U.S. Pat. No. 5,625,048 Issued Apr. 4, 1997 and International Publication No: WO 97/26333, hereby incorporated by reference in their entireties, can also be used.

The non-iENTP sequences of the iENTP fusion protein can be amino- or carboxy-terminal to the iENTP sequences. More preferably, for stable expression of an iENTP fusion protein (including a proteolytically inactive iENTP fusion protein), the portion of the non-iENTP fusion protein is joined via a peptide bond to the amino terminus of the iENTP protein. A recombinant DNA molecule encoding such a fusion protein comprises a sequence encoding at least a functionally active portion of a non-iENTP protein joined in-frame to the iENTP coding sequence. In one such embodiment the DNA molecule encodes a cleavage site for a specific protease, e.g., thrombin or Factor Xa, preferably at the iENTP-non-iENTP juncture. In a specific embodiment, the fusion protein is expressed in *Escherichia coli*.

Antibodies to the iENTPs of the present invention are also part of the present invention. In a particular embodiment the antibody is raised against an iENTP having an amino acid sequence of SEQ ID NO:2. In another such embodiment the antibody is raised against an iENTP having an amino acid sequence of SEQ ID NO:2 comprising one or more conservative substitutions thereof. In still another embodiment the antibody is raised against a portion of, or alternatively all of the N-terminal 92 amino acids of SEQ ID NO:2, i.e., amino acids 1–92 of SEQ ID NO:2.

In one embodiment the antibody is a polyclonal antibody. In another embodiment the antibody is a monoclonal antibody. In yet another embodiment the monoclonal antibody is a chimeric antibody. The present invention also includes an immortal cell line that produces a monoclonal antibody of the present invention.

Still another aspect of the present invention includes a transfected or transduced cell in which all detectable nucleoside transport activity is performed by the nucleoside transport protein encoded by a nucleic acid of the present invention. In one embodiment of this type, the transfected or transduced cell is a vertebrate cell. In a preferred embodiment the transfected or transduced cell is a mammalian cell. In a more preferred embodiment the transfected or transduced cell is a human cell. In one such embodiment, the transfected cell is a human T-cell leukemia CEM cell. In a more particular embodiment of this type the transfected human [@00ce]ll is a CEM/N1-7 cell. In a preferred embodiment of this aspect of the present invention, all detectable nucleoside transport activity is performed by an iENTP having the amino acid sequence of SEQ ID NO:2, or an active fragment of that iENTP. In a related embodiment the iENTP has the amino acid sequence of SEQ ID NO:2 comprising a conservative substitution thereof, or an active fragment of that iENTP.

The present invention also includes a nucleoside transport deficient subline of a human T-cell leukemia cell line CEM, transfected with an Epstein-Barr Nuclear Antigen 1 expression cassette, in which the cell line is capable of supporting the episomal replication of an Epstein-Barr virus-based mammalian expression vector. In one particular embodiment of 15 this type the expression vector is pDR2. In a preferred embodiment of this type the cell line has a stable transfection frequency with pDR2 of approximately $10^{-2}$. In one particular embodiment the nucleoside transport deficient subline is CEM/C19.

Ribozymes specifically designed to modify the nucleic acids of the present invention are also contemplated as part of the present invention. Similarly antisense nucleic acids that hybridize under physiological conditions to an MRNA encoding an iENTP of the present invention is also included in the present invention. In one such embodiment, the antisense nucleic acid hybridizes to the mRNA that corresponds to the sense strand of nucleotides 238–1605 of the nucleotide sequence of SEQ ID NO:1.

A related aspect of the invention is a knockout mouse for the iENTPs of the present invention. One such embodiment comprises a first and a second allele which naturally encode and express the nucleoside transport protein having the amino acid sequence of SEQ ID NO:2. Both the first allele and the second allele each contain a defect which prevents the knockout mouse from expressing a nucleoside transport protein that is both insensitive to NBMPR and can function as an equilibrative nucleoside transport protein. Such a knockout mouse is particularly susceptible to drugs such as NBMPR.

The present invention also includes methods of making and using the iENTPs, antibodies to the iENTPs, the nucleic acids encoding the iENTPs, oligonucleotides that hybridize to these nucleic acids, DNA constructs containing these nucleic acids, cells containing these constructs, as well as to the other compositions and processes of the present invention.

Accordingly, one aspect of the present invention includes a method of isolating a cDNA encoding a nucleoside transport protein. This process comprises transfecting a nucleoside transport protein deficient cell with an expression vector from an expression vector library, wherein the expression vector library contains a vector comprising a cDNA encoding a nucleoside transport protein. The cDNA encoding the nucleoside transport protein is expressed in the transfected cell. An expression vector containing the cDNA encoding a nucleoside transport protein is selected by culturing the transfected cell under conditions in which the cell growth is dependent on the expression of the nucleoside transport protein. Therefore the selected expression vector contains the cDNA encoding a nucleoside transport protein. The selected expression vector is extracted from the transfected cell. A host cell is transfected with the selected expression vector, and the cDNA encoding the nucleoside transport protein is isolated.

In a specific embodiment of this type includes a method of isolating a cDNA encoding an NBMPR insensitive, equilibrative nucleoside transport protein (iENTP cDNA). This process comprises transfecting a nucleoside transport protein deficient cell with an expression vector from an expression vector library, wherein a cDNA library containing an iENTP cDNA has been subcloned into the expression vector library, and wherein the iENTP cDNA is expressed in the transfected cell. An expression vector containing the iENTP cDNA is selected by culturing the transfected cell under conditions in which the cell growth is dependent on the expression of the iENTP and its corresponding transport activity, and wherein the selected expression vector contains the iENTP cDNA. The selected expression vector is extracted from the transfected cell. A host cell is transfected with the selected expression vector, and the cDNA encoding the NBMPR insensitive, equilibrative nucleoside transport protein is isolated. In a preferred embodiment of this type the transfected cell is a human cell that expresses EBNA-1 and the human cell is CEM/C19.

Another aspect of the present invention includes a method of making an NBMPR insensitive, equilibrative nucleoside transport protein of the present invention through introducing an expression vector comprising a nucleic acid encoding the iENTP or an active fragment thereof into a host cell, and expressing the nucleic acid in the host cell. In one embodiment the host cell is a prokaryotic cell. In another embodiment the host cell is a eukaryotic cell. In one specific embodiment, the eukaryotic cell is an insect cell. In a particular embodiment the iENTP has an amino acid sequence of SEQ ID NO:2. In another particular embodiment the iENTP has an amino acid sequence of SEQ ID NO:2 comprising a conservative substitution thereof. In one embodiment, the method further comprises purifying the iENTP.

The present invention includes methods for obtaining a purified NBMPR insensitive, equilibrative nucleoside transport protein (iENTP) or an active fragment thereof, from a cell that expresses the iENTP which comprises lysing the cell, and purifying the NBMPR insensitive, equilibrative nucleoside transport protein. In one embodiment the purifying step includes extracting the iENTP from the plasma membrane of the cell. In another such embodiment the purifying step also includes fractionating the proteins contained in the cell. In a particular embodiment, the iENTP is obtained from a natural source. In a preferred embodiment the natural source is a mammalian cell. In another particular embodiment the iENTP is a recombinant protein obtained from a prokaryotic cell. In still another embodiment the iENTP is a recombinant protein obtained from a eukaryotic cell. In one preferred embodiment the iENTP has an amino acid sequence of SEQ ID NO:2. In another preferred embodiment the iENTP has an amino acid sequence of SEQ ID NO:2 comprising a conservative substitution thereof.

Yet another aspect of the invention includes a method of identifying a ligand of an iENTP of the present invention which comprises contacting a potential ligand with the isolated iENTP under physiological conditions (e.g., neutral pH, buffered solution with approximately 150 mM salt) and detecting whether the potential ligand binds to the iENTP wherein a potential ligand is selected as a ligand if it binds to the iENTP. The ligand and/or the iENTP can be labeled such as with a label defined below. Similarly, either the iENTP or ligand can be attached to a solid support. The binding can be detected with any of the standard protein-ligand binding assays known in the art as exemplified below. Once a ligand is identified its dissociation constant can be determined. Alternatively, the detecting step may be performed by determining the dissociation constant initially. In either case a potential ligand is selected as a ligand when the dissociation constant is less than $10^-M$. In one such embodiment the ligand is a permeant of the iENTP. In another embodiment, the ligand is an inhibitor of the iENTP. In yet another embodiment, the ligand is both a permeant and an inhibitor of the iENTP. In one preferred embodiment the iENTP has an amino acid sequence of SEQ ID NO:2. In another preferred embodiment the iENTP has an amino acid sequence of SEQ ID NO:2 comprising a conservative substitution thereof.

The present invention also includes specific methods of identifying a permeant of an NBMPR insensitive, equilibrative nucleoside transport protein (iENTP). In one such embodiment a nucleoside or nucleoside analog is contacted with a transfected or transduced cell of the present invention in which all detectable nucleoside transport activity is performed by an iENTP of the present invention. The nucleoside transport of the nucleoside or nucleoside analog by the transfected or transduced cell is evaluated, wherein the nucleoside or nucleoside analog is identified as a permeant when the transport of the nucleoside or nucleoside analog into the transfected or transduced cell is determined to follow a facilitated diffusion process. In one such embodiment the nucleoside or nucleoside analog is an antiviral nucleoside analog. In another embodiment the nucleoside or nucleoside analog is an antitumor nucleoside analog. In one particular embodiment of this type the transfected or transduced cell is a transfected or transduced human cell. In one preferred embodiment the iENTP has an amino acid sequence of SEQ ID NO:2. In another preferred embodiment the iENTP has an amino acid sequence of SEQ ID NO:2 comprising a conservative substitution thereof.

The present invention further includes specific methods of selecting drugs that inhibit an NBMPR insensitive, equilibrative nucleoside transport protein. One such embodiment comprises contacting a potential drug with a transfected or transduced cell of the present invention in which all detectable nucleoside transport activity is performed by an iENTP of the present invention. The nucleoside transport activity of the cell is evaluated. A potential drug is selected as a drug when a decrease in the nucleoside transport activity is determined relative to that determined when the evaluating was performed in the absence of the potential drug.

In one embodiment of this type the nucleoside transport activity of the transfected or transduced cell is evaluated as a function of the determination of the trans-stimulation of a permeant. In another embodiment the nucleoside transport activity of the transfected or transduce cell is evaluated as a function of the determination of the direct transport of a permeant. In still another embodiment the nucleoside transport activity of the transfected or transduced cell is evaluated as a function of the determination of the countertransport of a permeant. In one specific embodiment, the nucleoside transport activity of the transfected or transduced cell is evaluated as a function of the toxicity of a nucleoside analog which is a permeant of the iENTP, such as tubercidin, 2-chloro-2'-deoxyadenosine, or Ara-C. In yet another embodiment, the nucleoside transport activity of the transfected or transduced cell is evaluated as a function of toxicity in the presence of an antimetabolite. In yet another embodiment the nucleoside transport activity of the transfected or transduced cell is evaluated as a function of two of these determinations. In still another embodiment the nucleoside transport activity of the transfected or transduced cell is evaluated as a fuinction of all of these determinations.

Another embodiment of a method of selecting a drug that inhibits an NBMPR insensitive, equilibrative nucleoside transport protein (iENTP) comprises detecting the mutual inhibition (i.e. mutual competition) of a potential drug with a perrneant, such as uridine for the iENTP in a transfected or transduced cell of the present invention in which all detectable nucleoside transport activity is performed by an iENTP of the present invention. A potential drug is selected as a drug when mutual inhibition is detected. This embodiment may be used alone or in conjunction with the other determinations described above.

For any of the drug assays of the present invention the iENTP. functions as an equilibrative nucleoside transport protein, is insensitive to NBMPR, and contains approximately 450 amino acid residues. In one particular embodiment the iENTP has an amino acid sequence of SEQ ID NO:2. In another embodiment the iENTP has an amino acid sequence of SEQ ID NO:2 comprising a conservative substitution thereof. In a preferred embodiment the transfected or transduced cell is a human transfected or transduced cell.

Accordingly, it is a principal object of the present invention to provide a purified NBMPR-insensitive, equilibrative nucleoside transport protein (iENTP).

It is a further object of the present invention to provide an isolated nucleic acid encoding a iENTP.

It is a further object of the present invention to provide a DNA construct containing a nucleic acid encoding a iENTP.

It is a further object of the present invention to provide an antibody specific for a purified iENTP.

It is a further object of the present invention to provide a method of producing an iENTP, including through modification of a iENTP, and through recombinant technology.

It is a further object of the present invention to provide a method of selecting a drug that preferentially inhibits an iENTP-dependent nucleoside transport pathway.

It is a further object of the present invention to provide a method of screening drug libraries for drugs that preferentially inhibit an iENTP.

It is a further object of the present invention to provide a cell in which the only detectable facilitated diffusion pathway for nucleosides includes an iENTP.

It is a further object of the present invention to provide a cell where the NBMPR-insensitive facilitated diffusion pathway for nucleosides includes a modified iENTP.

It is a further object of the present invention to provide a method of cancer chemotherapy by transducing hematopoietic stem cells ex vivo with a cDNA encoding an iENTP, introducing the transduced cells into an animal subject, and then treating the animal subject with an antimetabolite and NBMPR.

It is a further object of the present invention to provide a novel method of hematopoietic cell-directed gene therapy using an expression vector encoding the iENTP.

These and other aspects of the present invention will be better appreciated by reference to the following drawings and Detailed Description.

BRIEF DESCRIPTION OF THE DRAWINGS

FIG. 1 shows uridine uptake in N1-7 and C19 cells.

FIGS. 2A and 2B depict the comparison of the amino acid sequences of proteins related to hENT2. Two related sequences found in the Genbank database were aligned with hENT2 using the Pileup program in the GCG suite of sequence analysis software. Residues that are identical or have conservative substitutions in at least 8 of the 10 sequences are shown on a black background, and conservative substitutions in at least 5 of the 10 sequences are shown on a grey background. Putative transmembrane domains are shown by dashed lines (===), the N-glycosylation consensus sequence ****, and the start site for mouse and human HNP36 by#.

DETAILED DESCRIPTION OF THE INVENTION

Figure 1A:
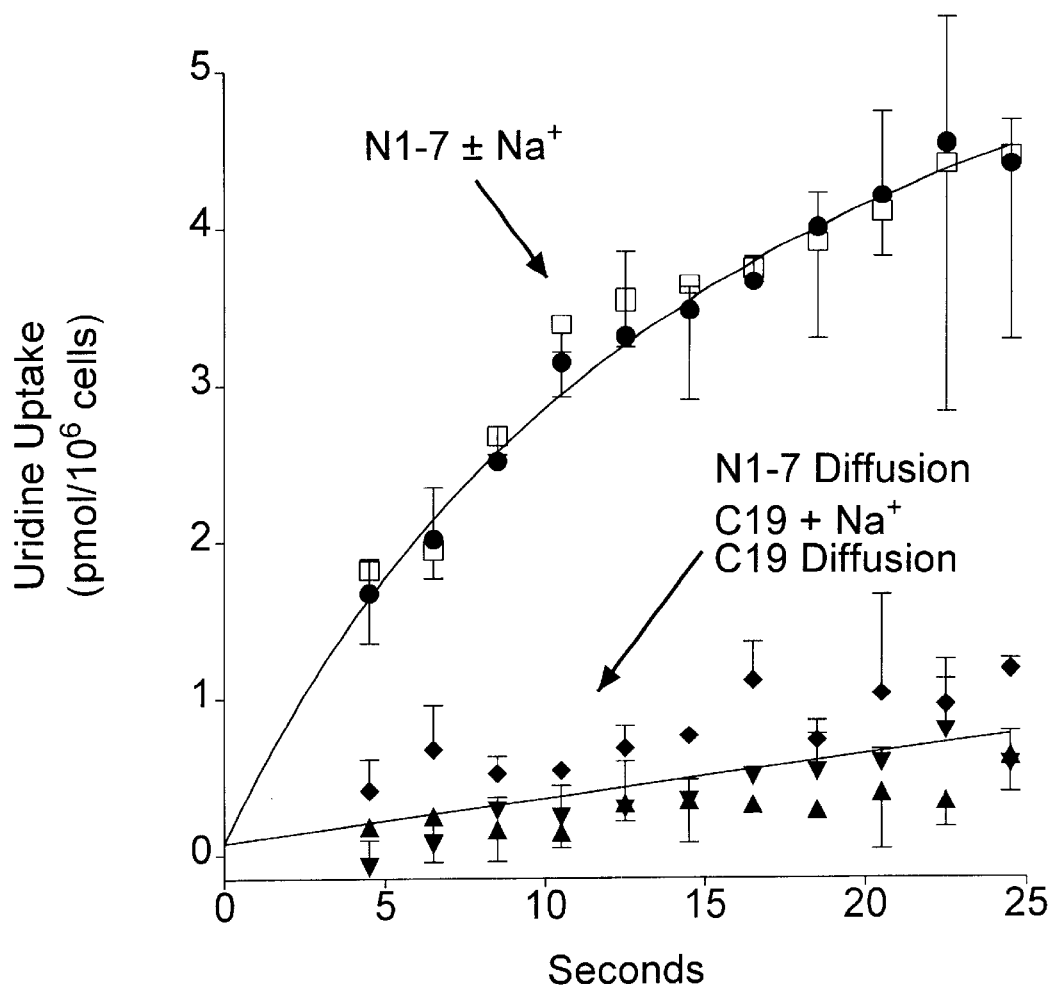
FIG. 1A depicts $^3$H-uridine uptake (10 $\mu$M at 2.5 $\mu$Ci/ml) by CEM/N1-7 (•, □, ♦) and CEM/C19 (▲,▼) cells which was determined at 22° C. in Na$^+$ (filled symbols) or Na$^+$-free (▽) in the presence (♦, ▼) or absence (•, □, ▲) of a large excess (4 mM) unlabeled uridine as described in the methods. The values shown are means of duplicate assays and have been corrected for extracellular water space.

The present invention in its broadest embodiment provides an equilibrative nucleoside transport protein which is insensitive to nitrobenzylmercaptopurineriboside, NBMPR, [6-[(4-nitrobenzyl)thio-9-β-D-ribofuranosyl purine]. The NBMPR-insensitive nucleoside transport protein (iENTP) is a transmembrane protein that serves to transport nucleosides across the plasma membrane through a facilitated diffusion process. The present invention also provides nucleic acids encoding the iENTPs of the present invention which can be used to transfect or transduce mammalian cells for various medical purposes. For example, such a transfected or transduced cell can be used as a screening tool for identifying antitumor and antiviral nucleoside analogs that can be preferentially transported into cells by this specific nucleoside transport protein. In addition, hematopoietic cells transduced with an iENTP of the present invention can be used in cancer chemotherapy protocols in which both the de novo nucleoside biosynthesis and the major nucleoside salvage pathway of the hematopoietic cells are purposely disabled. In such instances the expression of the iENTP uniquely provides the transduced cells with an alternative means of obtaining the required nucleosides.

Therefore, if appearing herein, the following terms shall have the definitions set out below.

As used herein "iENTP" and "ei" transporter are interchangeable names for an NBMPR-insensitive equilibrative nucleoside transport protein, which is a transmembrane protein that functions in the facilitated diffusion of nucleosides across cell membranes. As disclosed herein, "hENT2" is a human iENTP that has an amino acid sequence of SEQ ID NO:2. The natural nucleic acid sequence encoding hENT2 consists of nucleotides 238–1605 of SEQ ID NO:1.

A nucleoside transporter may be classified as being either "NBMPR-insensitive" or "NBMPR-sensitive." This classification system is widely accepted in the field [See Griffith et al., Biochim. Bioph. Acta 1286:153–181 (1996)] to distinguish two major classes of nucleoside transport proteins. "NBMPR-sensitive" indicates that the nucleoside transporter has a high sensitivity to the inhibitor NBMPR i.e., $IC_{50}$ values of 0.1 to 1 nanomolar. "NBMPR-insensitive" indicates that the nucleoside transporter is insensitive to nanomolar concentrations of NBMPR, but can be inhibited by higher (e.g., micromolar) concentrations.

As used herein an "active fragment" of an iENTP is a polypeptide or glycopolypeptide that has an amino acid sequence that corresponds to that of a full-length iENTP except the active fragment has at least one less amino acid than the corresponding full-length iENTP; further an "active fragment" of an IENP is NBMPR-insensitive, and has at least 20% of the nucleoside transport activity of the corresponding full-length iENTP, (determined under conditions in which the full-length iENTP has nucleoside transport activity.)

As used herein a "functional iENTP" is a iENTP that is NBMPR-insensitive and has at least 20% of the nucleoside transport activity of the corresponding native iENTP.

As used herein, an "antimetabolite" is a compound that interferes with the synthesis and/or metabolism of nucleotides or nucleosides. In one instance an antimetabolite can inhibit de novo nucleotide synthesis. In another instance an antimetabolite can be a nucleoside analog that interferes with a nucleoside and/or nucleotide-dependent process. Antimetabolites include trimetrexate, methotrexate (MTX), N-(phosphonacetyl)-L-aspartic acid (PALA), and 5-fluorouracil (5-FU).

As used herein "facilitated diffusion" is a carrier-mediated transport system that operates along a concentration gradient of the permeating solute. At equilibrium, the solute will attain the same concentration on either side of the membrane, as in simple diffusion. The transport of a permeant "is determined to follow a facilitated diffusion process" when the kinetic determinations for the transport process are consistent with that predicted for a facilitated diffusion process [See Stein, Transport and Diffusion Across Cell Membranes, Academic Press, London (1986)].

As used herein the term "approximately" is used to signify that a value is within ten percent of the indicated value i.e., a protein containing "approximately" 450 amino acid residues can contain between 405 and 495 amino acid residues.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such solvent preferences.

As used herein a "ligand" of an iENTP can be either a natural or artificial binding partner for the iENTP which binds to the iENTP under physiological conditions forming a binding complex. In preferred embodiments the iENTP-ligand binding complex has a dissociation constant of less than $10^{-5}$ M. Ligands include perrneants, and/or inhibitors and activators of the iENTP-dependent nucleoside salvage pathway.

As used herein a "permeant" is a nucleoside or nucleoside analog that binds to an iENTP and is transported by the iENTP across a membrane by a facilitated diffusion process.

As used herein the "iENTP-dependent nucleoside salvage pathway" is used to denote an iENTP-dependent transport of nucleosides across the plasma membrane of a cell.

As used herein a cell has "detectable nucleoside transport activity" when the rate of nucleoside uptake of the cell is greater than that determined for simple diffusion. The rate of diffusion is measured by the uptake of $^3$H-uridine (1–10 μM) over a thirty second time course, at 22° C. in the presence of a large excess (1–10 mM) of unlabeled uridine, or a competing nucleoside. For example, see FIG. 1, where the uptake of $^3$-uridine by CEM/C19 cells is not significantly different in the presence or absence of a large excess of unlabeled uridine. Similarly, a cell has "no detectable nucleoside transport activity" when the rate of nucleoside uptake of the cell is not significantly different than that determined for a simple diffusion process, as determined by the method above.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. The transfecting DNA can be maintained in an episome as exemplified in the transfection studies using the CEM/N1-7 cell described herein. A cell has been "transduced" by exogenous or heterologous DNA when the exogenous or heterologous DNA is introduced by a viral vector.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another embodiment the heterologous nucleotide can function as a means of detecting a nucleotide sequence of the present invention. A heterologous nucleotide sequence can comprise non-coding sequences including restriction sites, regulatory sites, promoters and the like.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the negative gene). Allelic variations or naturally-occurring mutational events do not give rise to a heterologous region of DNA as defined herein.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5x or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. "Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

iENTPs: Proteins and Polypeptides

The present invention provides isolated iENTPs and active fragments thereof. An iENTP is a transmembrane protein that contains approximately 450 amino acid residues, 8 to 12 putative transmembrane domains, is NBMPR insensitive, and functions as an equilibrative nucleoside transport protein. iENTPs represent one class of five, or more, classes of nucleoside transporters found in mammalian cells (Griffith et al., 1996, supra; Cass, 1995, supra). In preferred embodiments the iENTP is a mammalian protein. In one embodiment the IENTP is encoded by a nucleotide sequence having at least 80% similarity with the coding sequence of SEQ ID NO:1. In another embodiment the IENTP is encoded by a nucleotide sequence having at least 80% identity with the coding sequence of SEQ ID NO:1. In still another embodiment the iENTP has an amino acid sequence of SEQ ID NO:2 comprising one or more conservative substitutions thereof. In a preferred embodiment the isolated iENTP is the human homolog (hENT2) having an amino acid sequence of SEQ ID NO:2. The iENTPS of the present invention may be used in assays to identify novel drugs, and the like, and in protein structure and mechanistic studies.

The hENT2 protein is 50% identical (having 69% similarity) to the HENT1 protein, the human homologue of the NBMPR-sensitive equilibrative nucleoside transport protein. As found for the concentrative transporters, hENT1 and hENT2 do not share significant homology with other known membrane transport proteins, and appear to represent a new family of transport proteins.

Surprisingly, the carboxy-terminal portion of the hENT2 protein is nearly identical to a 326 residue predicted peptide (hHNP36) in the Genbank database that has been identified as growth factor-induced "delayed early response" gene of unknown function [Williams et al. Biochem. Biophy. Res. Comm. 213:325–333 (1995)]. Inspection of the hHNP36 nucleotide sequence revealed two potential open reading frames with hHNP36 translated from the second start codon. While hENT2 also has two potential start codons, they are within the same open reading frame. The full length cDNA of hHNP36 (2281 bp) is nearly identical to hENT2, but contains a 68 bp deletion beginning at position 338. This deletion shifts the initial reading frame relative to hENT2 and would result in a truncated 22 Kd peptide with only 51% identity to the hENT2 protein. Transient transfection studies with full length hENT2 and a 5'-truncated construct that lacks the first start codon (predicted protein 99% identical to hHNP36) demonstrated that a functional nucleoside transport protein is not produced from the second start codon. These data indicate that the hHNP36 peptide appears to be a truncated, non-functional form of hENT2.

The high degree of homology between hENT2 and hHNP36 was completely unexpected, and could not have been predicted from the earlier work of Williams etal. [Williams et al., 1995, supra]. HNP36 had been identified as a 36 Kd peptide by in vitro translation of both the human and mouse mRNA homologs, but no data was provided regarding its function. It was only reported that HNP36 was localized in the nucleolus, as determined by immunostaining studies in mouse cells [Williams et al., 1995, supra]. Therefore, knowledge of the 36 Kd peptide in the absence of the teachings provided by the present invention, could not have led to the iENTPs of the present invention.

The possible identity of hENT2 with a full-length, in frame natural analog of hHNP36 is consistent with the iENTP being a "delayed early response" gene. When quiescent cells are stimulated to proliferate there is a sequential expression of cellular genes whose products are thought to mediate the long-term responses to the growth factors. Therefore iENTPs are likely to play an important role in the proliferative response, when quiescent cells are stimulated into cycle by growth factors.

Modified iENTPs: The present invention also provides active fragments of the iENTPs and modified iENTPs of the present invention, such as tagged proteins, labeled proteins, fusion proteins and the like. Such modified iENTPs may be used for example as antigens or for marker purposes. In a particular embodiment of this type, the fusion protein comprises an iENTP protein or active fragment thereof having an amino acid sequence of SEQ ID NO:2 or SEQ ID NO:2 comprising a conservative substitution thereof. Modified iENTPs of the present invention retain their activity as NBMPR insensitive equilibrative nucleoside transport proteins. One particular use of the iENTP fusion proteins of the present invention is for the production of the iENTP-antibodies of the present invention.

An iENTP fusion protein comprises at least a portion of a non-iENTP protein joined via a peptide bond to at least a portion of an iENTP polypeptide. In preferred embodiments the portion of the iENTP is functional. The non-iENTP sequences can be amino- or carboxy-terminal to the iENTP sequences. More preferably, for stable expression of a proteolytically inactive iENTP fusion protein, the portion of the non-iENTP fusion protein is joined via a peptide bond to the amino terminus of the iENTP protein. A recombinant DNA molecule encoding such a fusion protein comprises a sequence encoding at least a portion of a non-iENTP protein joined in-frame to the iENTP coding sequence, and preferably encodes a cleavage site for a specific protease, e.g., thrombin or Factor Xa, preferably at the iENTP-non-iENTP juncture. In a specific embodiment, the fusion protein is expressed in *Escherichia coli*. Such a fusion protein can be used to isolate the iENTPs of the present invention, through the use of an affinity column which is specific for the protein fused to the iENTP. The purified iENTP may then be released from the fusion protein through the use of a proteolytic enzyme and the cleavage site such as has been referred to above.

In one such embodiment, a chimeric iENTP can be prepared, e.g., a glutathione-S-transferase (GST) fusion protein, a maltose-binding (MBP) protein fusion protein, or a poly-histidine-tagged fusion protein, for expression in a eukaryotic cell. Expression of an iENTP as a fusion protein can facilitate stable expression, or allow for purification based on the properties of the fusion partner. For example, GST binds glutathione conjugated to a solid support matrix, MBP binds to a maltose matrix, and poly-histidine chelates to a Ni-chelation support matrix. The fusion protein can be eluted from the specific matrix with appropriate buffers, or by treating with a protease specific for a cleavage site usually engineered between the iENTP and the fusion partner (e.g., GST, MBP, or poly-His) as described above. Alternatively the chimeric iENTP protein may contain the green fluorescent protein, and be used to determine the intracellular localization of the iENTP in the cell.

Genes Encoding iENTPs

The present invention contemplates isolation of a gene encoding an iENTP of the present invention, including a full length, or naturally occurring form of iENTP, and antigenic fragments thereof from any animal, particularly mammalian, and more particularly human, source. Such nucleic acids may be used for designing primers for RT-PCR, and for making probes that are useful for determining the expression of iENTP messenger RNA in tissues and tumors. Similarly such nucleic acids can be used to determine the expression of iENTP messenger RNA in normal tissues and tumors by Northern Blot analysis, RNA protection assays and the like. As used herein, the term "gene" refers to an assembly of nucleotides that encode a polypeptide, and includes cDNA and genomic DNA nucleic acids.

Figure 6:
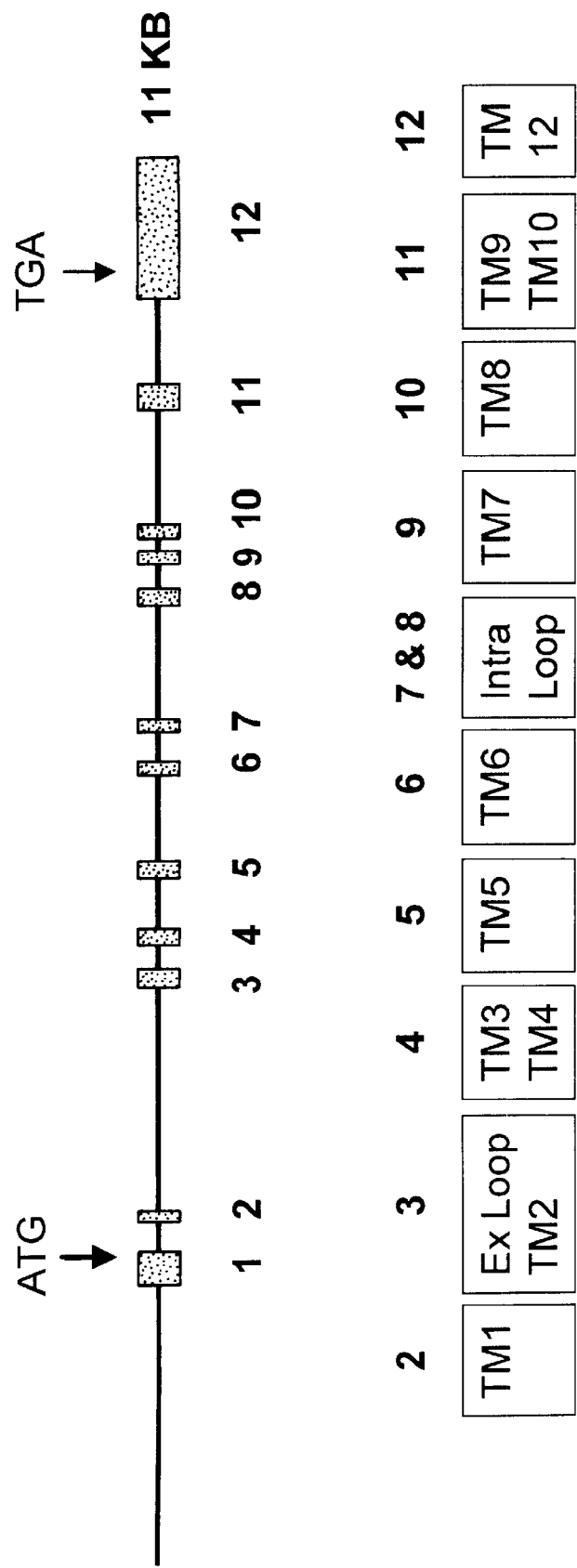
FIG. 6 shows the exon structure of an iENTP of the present invention. As shown, each exon approximately defines a different functional domain. TM is short for transmembrane.
Figure 7:
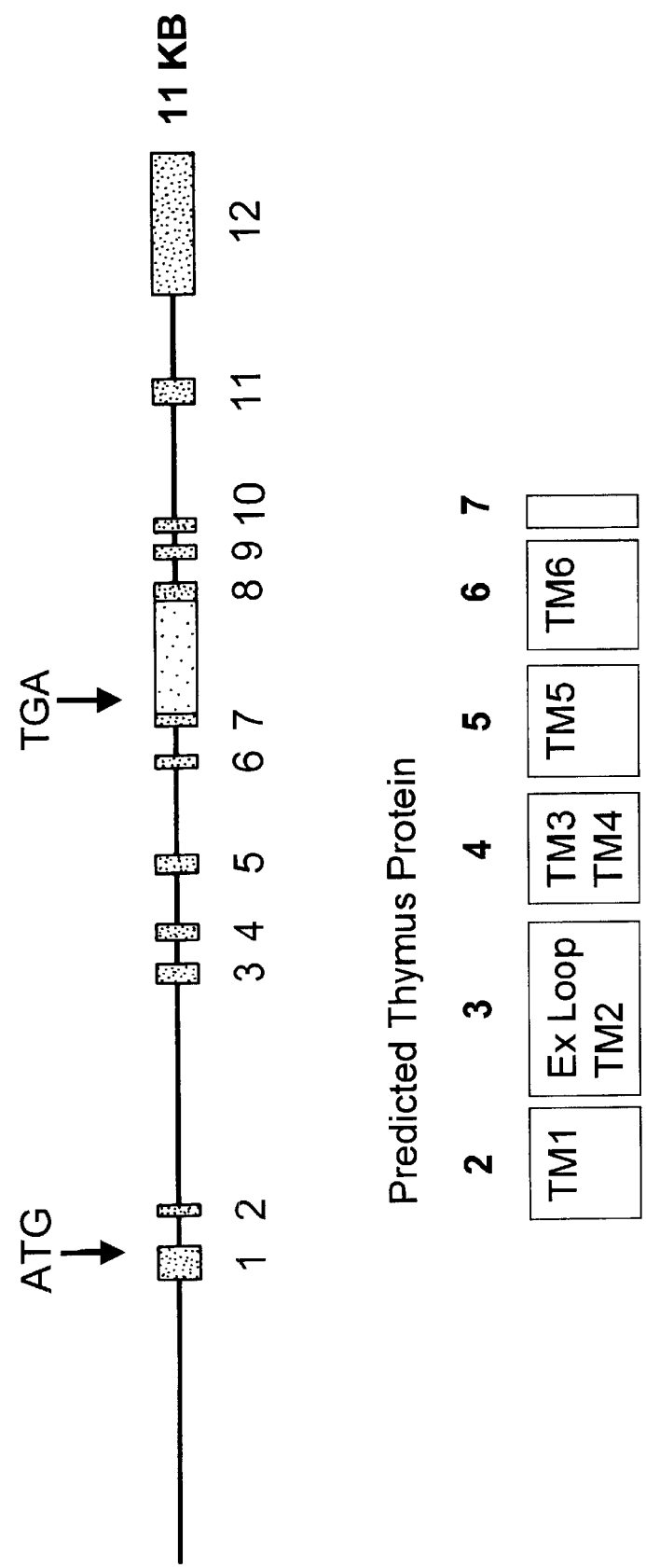
FIG. 7 shows the 3.5 KB message isolated from Thymus which is apparently a splice variant of an iENTP.

The present invention provides the primary structure of genes encoding iENTPs as exemplified in FIG. 6 and FIG. 7. Furthermore, the present invention provides the genetic information that allows the determination of tissue specific regulatory elements of genes encoding the iENTPs of the present invention. Such regulatory elements may be contained in SEQ ID NO:6.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A gene encoding iENTP, whether genomic DNA or cDNA, can be isolated from any source, particularly from a human cDNA or genomic library. In view and in conjunction with the present teachings, methods well known in the art, as described above can be used for obtaining iENTP genes from any source (see, e.g., Sambrook et al., 1989, supra).

Accordingly, any animal cell or transformed animal cell line potentially can serve as the nucleic acid source for the molecular cloning of a iENTP gene. The DNA may be obtained by standard procedures known in the art from cloned DNA (e.g., a DNA "library"), and preferably is obtained from a cDNA library prepared from tissues with high level expression of the protein, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. 1, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired iENTP gene may be accomplished in a number of ways. For example, the generated DNA fragments may be screened by nucleic acid hybridization to a labeled probe of the present invention (Benton and Davis, 1977, Science 196:180; Grunstein and Hogness, 1975, Proc. Natl. Acad. Sci. U.S.A. 72:3961). For example, a set of oligonucleotides corresponding to the sequence information provided by the present invention can be prepared and used as probes for DNA encoding iENTP (e.g., in combination with a poly-T primer for RT-PCR). Preferably, a probe is selected that is highly unique to iENTP of the invention. Those DNA fragments with substantial homology to the probe will hybridize. As noted above, the greater the degree of homology, the more stringent hybridization conditions can be used.

Further selection can be carried out on the basis of the properties of the gene, e.g., if the gene encodes a protein product having the isoelectric, electrophoretic, amino acid composition, or partial amino acid sequence of the iENTP as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for iENTP.

An iENTP gene of the invention can also be identified by MRNA selection, i.e., by nucleic acid hybridization followed by in vitro translation. In this procedure, nucleotide fragments are used to isolate complementary mRNAs by hybridization. Such DNA fragments may represent available, purified iENTP DNA, or may be synthetic oligonucleotides designed from the partial amino acid sequence information. Immunoprecipitation analysis or functional assays (e.g., nucleoside transport activity) of the in vitro translation products of the products of the isolated mRNAs identifies the MRNA and, therefore, the complementary DNA fragments, that contain the desired sequences. In addition, specific mRNAs may be selected by adsorption of polysomes isolated from cells to immobilized antibodies specifically directed against iENTP.

A radiolabeled iENTP cDNA can be synthesized using the selected MRNA (from the adsorbed polysomes) as a template. The radiolabeled mRNA or cDNA may then be used as a probe to identify homologous iENTP DNA fragments from among other genomic DNA fragments.

The present invention also relates to cloning vectors containing genes encoding analogs and derivatives of iENTP of the invention, that have the same or homologous functional activity as iENTP, and homologs thereof from other species. The production and use of derivatives and analogs related to iENTP are within the scope of the present invention. In a specific embodiment, the derivative or analog is functionally active, i.e., capable of exhibiting nucleoside transport activity.

iENTP derivatives can be made by altering encoding nucleic acid sequences by substitutions, additions or deletions that provide for functionally equivalent molecules. Preferably, derivatives are made that have enhanced or increased functional activity or greater specificity with regard to a particular permeant relative to native iENTP. Alternatively, such derivatives may encode soluble fragments of zENTP extracellular domain that have the same or greater affinity for the natural permeants of the iENTPs of the present invention. Such soluble derivatives also may be potent inhibitors of the nucleoside transport activity of the iENTP.

Due to the degeneracy of nucleotide coding sequences, other DNA sequences which encode substantially the same amino acid sequence as a iENTP gene may be used in the practice of the present invention. These include but are not limited to allelic genes, homologous genes from other species, and nucleotide sequences comprising all or portions of iENTP genes which are altered by the substitution of different codons that encode the same amino acid residue within the sequence, thus producing a silent change. Likewise, the iENTP derivatives of the invention include, but are not limited to, those containing, as a primary amino acid sequence, all or part of the amino acid sequence of a iENTP protein including altered sequences in which functionally equivalent amino acid residues are substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure, which induces β-turns in the protein's structure.

The genes encoding iENTP derivatives and analogs of the invention can be produced by various methods known in the art. The manipulations which result in their production can occur at the gene or protein level. For example, the cloned iENTP gene sequence can be modified by any of numerous strategies known in the art (Sambrook et al.,1989, supra). The sequence can be cleaved at appropriate sites with restriction endonuclease(s), followed by further enzymatic modification if desired, isolated, and ligated in vitro. In the production of the gene encoding a derivative or analog of iENTP, care should be taken to ensure that the modified gene remains within the same translational reading frame as the iENTP gene, uninterrupted by translational stop signals, in the gene region where the desired activity is encoded.

Additionally, the iENTP-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity or specificity for a particular permeant, of the mutated iENTP gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transduction, transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2 μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of iENTP

The present invention provides for expressing the nucleic acids which encode the iENTPs active fragments thereof, derivatives or analog thereof, or a functionally active derivative, including a chimeric protein, thereof, that has been inserted into an appropriate expression vector, i.e., a vector which contains the necessary elements for the transcription and translation of the inserted protein-coding sequence. Such elements are termed herein a "promoter." Thus, the nucleic acid encoding an iENTP of the invention is operationally associated with a promoter in an expression vector of the invention. Both cDNA and genomic sequences can be cloned and expressed under control of such regulatory sequences. An expression vector also preferably includes a replication origin. One particular use for such expression vectors is to express an iENTP in large quantities that can be used for functional and structural studies of the purified transport protein.

The necessary transcriptional and translational signals can be provided on a recombinant expression vector, or they may be supplied by the native gene encoding iENTP and/or its flanking regions.

Potential chimeric partners for the iENTP of the present invention include substitute lectin domains, either from naturally occurring multivalent lectin receptors, such as mannose receptor of macrophages, natural lectins, or other sources.

Potential host-vector systems include but are not limited to mammalian cell systems, infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on th e host-vector system utilized, any one of a number of suitable transcription and translation elements may be used.

A recombinant iENTP protein of the invention, or functional f ragment, derivative, chimeric construct, or analog thereof, may be expressed chromosomally, after integration of the coding sequence by recombination. In this regard, any of a number of amplification systems may be used to achieve high levels of stable gene expression (See Sambroek et al., 1989, supra).

The cell containing the recombinant vector comprising the nucleic acid encoding iENTP is cultured in an appropriate cell culture medium under conditions that provide for expression of iENTP by the cell.

Any of the methods previously described for t he insertion of DNA frag ments into a cloning vector may be use d to construct expression vectors containing a gene consisting of appropriate transcriptional/translational control signals and the protein coding sequences. These methods may include in vitro recombinant DNA and synthetic techniques and in vivo recombination (genetic recombina tion).

Expression of iENTP may be controlled by any promoter/ enhancer element Known in the art, but these regulatory elements must be functional in the host selected for expression. Promoters which may be used to control iENTP gene expression include, those described in Example 1 below, as well as the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 198 1, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A . 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander etal., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing a nucleic acid encoding an iENTP of the invention can be identified by four general approaches: (a) PCR amplification of the desired plasmid DNA or specific MRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding iENTP is inserted within the "selection marker" gene sequence of the vector, recombinants containing the iENTP insert can be identified by the absence of the iENTP gene function. In the fourth approach, recombinant expression vectors can be identified by assaying for the activity, biochemical, or immunological characteristics of the gene product expressed by the recombinant, provided that the expressed protein assumes a finctionally active conformation. This last approach has been used in Example 1, below.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, xbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terrninal peptide for ProBond purification, and blue/white recombinant screening of plaques; Invitrogen (220)) can be used. Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE 14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV irnmediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the iENTP protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

In a preferred embodiment the expression vector is pDR2 (Clonetech). In another preferred embodiment the expression vector is pcDNA3 (Invitrogen).

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, the transmembrane iENTP expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, iENTP activity. Furthermore, different vector/host expression systems may affect processing reactions, such as proteolytic cleavages, to a different extent. Vectors are introduced into the desired host cells by methods known in the art, e.g., transfection, transduction, electroporation, microinjection, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

The present invention also provides cell lines made from cells transfected or transduced with the iENTPs of the present invention. In preferred embodiments of this type the cells are mammalian cells. In one such embodiment the iENTP is introduced into a COS-1 cell with a pcDNA3 expression vector, as exemplified below. The iENTP expressed in a human cell line is preferentially hENT2. In one such embodiment, the human cell expresses hENT2 as its only detectable nucleoside transport protein. In a particular embodiment of this type, the human cell is the T-cell leukemia cell line CEM, transfected with an Epstein-Barr Nuclear Antigen 1 expression cassette with a pDR2 expression vector capable of supporting the episomal replication of an Epstein-Barr virus-based mammalian expression vector encoding the hENT2. Such a transfected cell expresses the iENTP as its only nucleoside transport protein and is therefore a valuable tool for further characterization of the iENTPs of the present invention. Heretofore, such characterization appeared to be an impossible task, as all known cell lines expressing an iENTP had also been shown to have one or more additional nucleoside transport activities. Such a cell line also is a valuable tool for determining whether antiviral and antitumor nucleoside analogs can enter cells via the ei transporter and/or for identifying specific inhibitors of iENTPs as discussed below. In one particular embodiment of this type, the cell is an CEM/N1-7 cell exemplified below.

Such a cell line also can be used in expression cloning of proteins using an episomally replicating Epstein-Barr virus based vector that requires the expression of EBNA-1 in trans, and requires nucleoside transport in the selection process (e.g. HAT selection (with adenine substituted for hypoxanthine since the line is HPRT deficient)). Such procedures and cell lines are especially useful for proteins that are expressed in larger quantities in a T-cell background.

General Protein Purification Procedures

The initial step for purifying the iENTPs of the present invention, active fragments thereof, and related tagged or fusion proteins generally consists of lysing the cells containing the iENTPs. Cell lysis can be achieved by a number of methods including through the use of a physical means such as a French press, a sonicator, or a blender; or through chemical means including enzymatic extractions (with for example, lysozyme or pancreatin), and/or organic extractions or solubilizations with detergents, such as sodium dodecyl sulfate (SDS), Triton X-100, nonidet P-40 (NP40), digoxin, sodium deoxycholate, and the like, including mixtures thereof, or through a combination of chemical and physical means. For example, solubilization can be enhanced by sonication of the suspension. Subsequent steps of purification include salting in or salting out, such as in ammonium sulfate fractionations; solvent exclusion fractionations, e.g., an ethanol precipitation; detergent extractions to free the membrane bound iENTPs of the present invention using such detergents as Triton X-100, Tween-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl] aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as PHENYLSEPHAROSE and a high salt buffer; affinity-binding, using, e.g., placing a nucleoside or nucleoside analog on to an activated support; immuno-binding, using e.g., an antibody to an iENTP of the present invention bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a buffered solution. Unless otherwise specified, generally 25–100 mM concentrations are used. Low concentration buffers generally infer 5–25 mM concentrations. High concentration buffers generally infer concentrations of the buffering agent of between 0.1–2M concentrations. Typical buffers can be purchased from most biochemical catalogues and include the classical buffers such as Tris, pyrophosphate, monophosphate and diphosphate. The Good buffers [Good, et al., *Biochemistry*, 5:467 (1966); Good et. al. *Meth. Enzymol.*, 24: Part B, 53 (1972); and Fergunson, et. al *Anal. Biochem.* 104:300, (1980)] such as Mes, Hepes, Mops, tricine and Ches.

Materials to perform all of these techniques are available from a variety of sources such as Sigma Chemical Company in St. Louis, Mo.

Antibodies to iENTPs

According to the invention, an iENTP obtained from a natural source or produced recombinantly or by chemical synthesis, and fragments or other derivatives or analogs thereof, including fusion proteins, may be used as an immunogen to generate antibodies that recognize the iENTP polypeptide. Such antibodies include but are not limited to polyclonal, monoclonal, chimeric, single chain, Fab fragments, and an Fab expression library. The anti-iENTP antibodies of the invention may be cross reactive, e.g., they may recognize an iENTP from different species. Polyclonal antibodies have greater likelihood of cross reactivity. Alternatively, an antibody of the invention may be specific for a single form of the iENTP, such as murine iENTP. Preferably, such an antibody is specific for human iENTP.

Various procedures known in the art may be used for the production of polyclonal antibodies to an iENTP of the present invention or derivative or analog thereof. For the production of antibody, various host animals can be immunized by injection with an iENTP or a derivative (e.g., fragment or fusion protein) thereof, including but not limited to rabbits, mice, rats, sheep, goats, etc. In one embodiment, an iENTP or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward an iENTP of the present invention, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et. al., in *Monoclonal Antibodies and Cancer Therapy*, Alan R. Liss, Inc., pp. 77–96 (1985)]. In an additional embodiment of the invention, monoclonal antibodies can be produced in gern-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicingthe genes from a mouse antibody molecule specific for an iENTP, for example, together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce iENTP-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for an iENTP or its derivatives, or nalogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment,.the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an iENTP, for example the predicted extracellular loop, amino acids 35–64 of SEQ ID NO:2, one may assay generated hybridomas for a product which binds to an iENTP fragment containing such epitope. For selection of an antibody specific to an iENTP from a particular species of animal, one can select on the basis of positive binding with an iENTP expressed by or isolated from cells of that species of animal.

The foregoing antibodies can be used in methods known in the art relating to the localization and activity of the iENTP, e.g., for Western blotting, imaging iENTP in situ, measuring levels thereof in appropriate physiological samples, etc. using any of the detection techniques mentioned above or known in the art. More particularly, the antibodies of the present invention can be used in flow cytometry studies, in immunohistochemical staining, and in immunoprecipitation which serves to aid the determination of the level of expression of an iENTP in a tumor or normal cell or tissue.

In a specific embodiment, antibodies that agonize or antagonize the activity of an iENTP can be generated. Such antibodies can be tested using the assays described infra for identifying ligands.

Labels

Suitable labels include enzymes and proteins such as green fluorescent protein, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procebures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et. al.

As exemplified herein, proteins, including the iENTPs of the present invention and antibodies thereto, can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^{3}H$]-amino acids (with the tritium substituted at non-labile positions).

Solid Supports

A solid phase support for use in the present invention will be inert to the reaction conditions for binding. A solid phase support for use in the present invention must have reactive groups in order to attach a binding partner, such as an oligonucleotide encoding an iENTP, an iENTP, or an antibody to an iENTP, or for attaching a linker or handle which can serve as the initial binding point for any of the foregoing. In another embodiment, the solid phase support may be a useful chromatographic support, such as the carbohydrate polymers SEPHAROSE, SEPHADEX, and agarose. As used herein, a solid phase support is not limited to a specific type of support. Rather a large number of supports are available and are known to any person having skill in the art. Solid phase supports include silica gels, resins, derivatized plastic films, glass beads, cotton, plastic beads, alumina gels, magnetic beads, membranes (including but not limited to nitrocellulose, cellulose, nylon, and glass wool), plastic and glass dishes or wells, etc. For example, solid phase supports used for peptide or oligonucleotide synthesis can be used, such as polystyrene resin (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California). In synthesis of oligonucleotides, a silica based solid phase support may be preferred. Silica based solid phase supports are commercially available (e.g., from Peninsula Laboratories, Inc.; and Applied Biosystems, Inc.).

Identification of Ligands for the iENTPs

Identification and isolation of a gene encoding an iENTP of the present invention provides for expression of iENTP in quantities greater than can be isolated from natural sources, or in indicator cells that are specially engineered to indicate the activity of iENTP expressed after transfection or transduction of the cells. Accordingly, in addition to rational design of permeants and/or inhibitors based on the structure of iENTP, the present invention contemplates an alternative method for identifying specific ligands (including permeants and/or inhibitors and the like) of an iENTP using various screening assays known in the art.

Any screening technique known in the art can be used to screen for ligands to an iENTP. The present invention contemplates screens for small molecule ligands or ligand analogs and mimics, as well as screens for natural ligands that bind to iENTP and its activity. Inhibitors can include analogues of lidoflazine, mioflazine, and draflazine and the like [Griffith et al., Biochem. Pharmacol., 40:2297–2303 (1990); Baer et al., Naunyn Schmiedebergs Arch. Pharmacol. 343:365–369 (1991); Pirovano et al., Eur. J. Pharnacol. MoL Pharmacol., 189:419–422 (1990); Pirovano et al., Nucleosides Nucleotides, 10:1177–1179 (1991); Kruidering et al., Nucleosides Nucleotides, 10: 1223–1224 (1991); Hammond, J. Pharmacol. Exp. Ther. 259:799–807 (1991); Van Belle et al., Nucleosides Nucleotides, 10:975–982 (1991)]. Natural products libraries also can be screened using assays of the invention for potential ligands to iENTP. In addition, a large number of nucleoside analogues have been identified in the art and can be used in such screens.

Knowledge of the primary sequence of the iENTPs of the present invention, and the similarity of that sequence with proteins of known function, can provide an initial clue as to new ligands of the protein. Identification and screening of ligands is further facilitated by determining structural features of the iENTP, e.g., using X-ray crystallography, neutron diffraction, nuclear magnetic resonance spectrometry, and other techniques for structure determination. These techniques provide for the rational design or identification of ligands.

Another approach uses recombinant bacteriophage to produce large libraries. Using the "phage method" [Scott and Smith, 1990, Science 249:386–390 (1990); Cwirla, et al., Proc. Natl. Acad. Sci., 87:6378–6382 (1990); Devlin et al., Science, 249:404406 (1990)], very large libraries can be constructed ($10^6$–$10^8$ chemical entities). A second approach uses primarily chemical methods, of which the Geysen method [Geysen et al., Molecular Immunology 23:709–715 (1986); Geysen et al. J. Immunologic Method 102:259–274 (1987)] and the method of Fodor et al. [Science 251:767–773 (1991)] are examples. Furka et al. [14th International Congress of Biochemistry, Volume 5, Abstract FR:013 (1988); Furka, Int. J. Peptide Protein Res. 37:487–493 (1991)], Houghton [U.S. Pat. No. 4,631,211, issued December 1986] and Rutter et al. U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90:10700–4 (1993); Ohlmeyer et al., Proc. Natl. Acad. Sci USA 90:10922–10926 (1993); Lam et al., International Patent Publication No. WO 92/00252; Kocis et al., International Patent Publication No. WO 9428028, each of which is incorporated herein by reference in its entirety], and the like can be used to screen for iENTP ligands according to the present invention.

The screening can be performed with recombinant cells that express the iENTP, or alternatively, using purified protein, e.g., produced recombinantly, as described above or from natural sources. For example, the ability of labeled, soluble or solubilized iENTP or fragment thereof that includes the permeant-binding portion of the molecule, to bind the permeant or inhibitor thereto, can be used to screen libraries, as described in the foregoing references.

One such procedure comprises contacting a potential ligand with the isolated iENTP under physiological conditions and detecting whether the potential ligand binds to the IENTP. A potential ligand is selected as a ligand if it binds to the iENTP. The binding can be detected with any of the standard protein-ligand binding assays known in the art as exemplified below. Either the iENTP or the ligand can be appropriately labeled as described above. Similarly, either the iENTP or ligand can be attached to a solid support. Once a ligand is identified, its dissociation constant can be determined. The ligand is selected when the dissociation constant is less than $10^{-5}$ M.

The present invention also provides specific methods of identifying a permeant of an iENTP using a recombinant cell that expresses the iENTP, i.e., a cell transfected or transduce with iENTP. In one such method, a potential permeant is contacted with a transfected or transduced cell in which all detectable nucleoside transport activity is performed by the IENTP. The nucleoside transport of the potential permeant is evaluated in the transfected or transduced cell. The potential permeant is identified as a permeant when the transport of the potential permeant in the transfected or transduced cell is determined to follow a facilitated diffusion process. Potential permeants can include antiviral nucleoside analogs, antitumor nucleoside analogs, or natural nucleosides. In preferred embodiments of this type, the transfected or transduced cell is a transfected or transduced human cell.

The present invention further provides specific methods for selecting a drug that inhibits an iENTP using a recombinant cell that expresses the iENTP as described above. In one such method, a potential drug is contacted with a transfected or transduced cell in which all detectable nucleoside transport activity is performed by the iENTP. The nucleoside transport activity of the cell is evaluated. A potential drug is selected as a drug when a decrease in the nucleoside transport activity is determined relative to that determined when the evaluating was performed in the absence of the potential drug. The nucleoside transport activity of the transfected or transduced cell can be evaluated from any number of ways including: as a function of the determination of the trans-stimulation of a permeant; as a function of cell toxicity; as a function of the determination of the direct transport of a permeant, as a finction of the determination of the countertransport of a permeant; as a finction of the toxicity of a nucleoside analog which is a permeant of the iENTP, such as tubercidin, 2-chloro-2'-deoxyadenosine or Ara-C (wherein a two-fold change or greater is considered significant); or as a function of two or more of these determinations.

A drug can also be selected using the iENTP-transfected or transduced cell described above by detecting the mutual inhibition (i.e. competition) of nucleoside transport in the transfected or transduced cell between a potential drug and a known permeant of the iENTP (such as adenosine). A potential drug is selected as a drug when mutual inhibition is detected. The inhibition may be measured by any known means including those described above.

Transgenic Vectors and Gene Therapy

The functional activity of iENTP can be evaluated transgenically. In this respect, a transgenic animal model can be used [Archibald et al., Int. Pat. Publ. WO90/05188; Hurwitz et al., Int. Pat. Publ. WO93/03164; Bleck et al., U.S. Pat. No. 5,530,177 issued Jun. 25, 1996; Drohan et al. U.S. Pat. No. 5,589,604]. The iENTP gene can be used in complementation studies employing a transgenic mouse for example. Transgenic vectors, including viral vectors, or cosmid clones (or phage clones) corresponding to the wild type locus of candidate gene, can be constructed using the isolated iENTP gene. Cosmids may be introduced into transgenic mice using published procedures [Jaenisch, Science, 240:1468–1474 (1988)]. In a genetic sense, the transgene acts as a suppressor mutation.

Alternatively, a transgenic animal model can be prepared in which expression of the iENTP gene is disrupted. Gene expression is disrupted, according to the invention, when no functional protein is expressed. One such method for preparing a such a "knockout mouse" is detailed by Capecchi et al., in U.S. Pat. No. 5,464,764. A standard procedure for evaluating the phenotypic effect of a gene product is to employ knock-out technology to delete the gene. Alternatively, recombinant techniques can be used to introduce mutations, such as nonsense and amber mutations, or mutations that lead to expression of an inactive protein.

The present invention also extends to the preparation of antisense nucleotides and ribozymes that may be used to interfere with the expression of the iENTPs at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific MRNA molecule [see Marcus-Sekura, Anal. Biochem. 172:298 (1988)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro [Marcus-Sekura, 1988, supra; Hambor et al., J Exp. Med. 168:1237 (1988)]. Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability t o excis e their ow n introns. By modifying the nucleotide sequence of these RNAs, researchers have been able to engineer molecules that recognize specific nucleotide sequences in an RNA molecule and cleave it [Cech, J. Am. Med. Assoc. 260:3030 (1988)]. Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific MRNA species, and eighteen base recognition sequences are preferable to shorter recognition sequences.

The DNA sequences encoding the iENTPs described and enabled herein may thus be used to prepare antisense molecules against and ribozymes that cleave mRNAs for the iENTPs, thus inhibit ing a cell f rom expre ssing the gene encoding the iENTP, thereby hindering or curtailing the nucleoside transport of a specific nucleoside or nucleoside analog into the cell.

In one embodiment, a gene encoding an iENTP or a ctive fragment thereof is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Examples of particular vectors include, but are not limited to, a defective herpes virus I (HSV1) vector [Kaplitt et al., Molec. Cell. Neurosci. 2:320–330 (1991)], an attenuated adenovirus vector, such as the vector described by Stratford-Perricaudet et al. [J. Clin. Invest. 90:626–630 (1992)], and a defective adeno-associated virus vector [Samulski et al., J. Virol. 61:3096–3101 (1987); Samulski et al., J. Virol. 63:3822–3828 (1989)].

Preferably, for in vitro administration, an appropriate immunosuppressive treatment is employed in conjunction with the viral vector, e.g., adenovirus vector, to avoid immunodeactivation of the viral vector and transduced cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, Nature Medicine (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al, 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, er al., *Proc. Natl. Acad. Sci. USA.* 85:8027–8031 (1988)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem. 267:963–967 (1992); Wu and Wu, *J. Biol. Chem.* 263:14621–14624 (1988); Hartmut et al., Canadian Patent Application No. 2,012,311, filed Mar. 15, 1990].

In a preferred embodiment of the present invention, a gene therapy vector as described above employs a transcription control sequence operably associated with the sequence for the iENTP inserted in the vector. That is, a specific expression vector of the present invention can be used in gene therapy.

Such an expression vector is particularly useful to regulate expression of a therapeutic iENTP gene. In one embodiment, the present invention contemplates constitutive expression of the iENTP gene, even if at low levels.

The present invention provides a method of using such expression vectors in cancer chemotherapy. Transducing normal hematopoietic stem cells ex vivo, with cDNA encoding the NBMPR-insensitive equilibrative nucleoside transport protein, would offer protection to the transduced cells in vivo, during antimetabolite therapy that is coupled with the administration of NBMPR, a potent inhibitor of the es nucleoside transporter. The transduced cells, which express the iENTP, would survive the NBMPR and antimetabolite therapy through the iENTP-dependent salvage of nucleosides from exogenous pools. In contrast, untransduced cells and tumor cells which do no express the iENTP, would be selectively diminished as the antimetabolite blocks de novo nucleoside biosynthesis, and NBMPR prevents nucleoside salvage via the es transporter.

The dosage of NBMPR to be administered can be empirically determined with initial studies in mouse models, and then in higher mammals. These are the type of studies that have become routine for those having skill in the art of chemotherapy. For example, normal mice can be treated by intraperitoneal administration with varying doses of methotrexate (MTX; 20 mg/kg–200 mg/kg) for five consecutive days, to determine cytotoxic effects on both normal myeloid progenitor cells and hematopoietic stem cells with this antimetabolite. Other nucleoside antimetabolites such as PALA, 5-fluorouracil, AraC, and AZT, can be similarly tested (as required) at clinically relevant dosages. The marrow from drug treated and untreated mice are examined for myeloid progenitor cell numbers to determine the degree of cytotoxic effects.

NBMPR (0.1 $\mu$M to 10 $\mu$M) and draflazine (0.1 $\mu$M to 10 $\mu$M) can be added in conjunction with the antimetabolite (at concentrations found to be cytotoxic in the above study) to murine bone marrow cells in an in vitro culture system optimized using medium supplemented with hematopoietic growth factors (IL-3 at 20 ng/ml, human IL-6 at 50 ng/ml, rat SCF at 50 ng/ml) and fetal bovine serum. The effect of NBMPR or draflazine on potentiating the activity of the antimetabolites are assessed by cell count measurements over a 24 hour period after treatment.

Hematopoietic stem cells can be transduced with either viral constructs (e.g., retrovirus, adeno-associated virus or lenti virus) containing a nucleic acid encoding an iENTP (e.g., hENT2) or a control nucleic acid, e.g., encoding MDRI [Pastan et al., *Proc. Nat. Acad. Sci.* 85:4486 (1988)]. Mice can then be transplanted with either hENT2 or MDR1 transduced cells e.g., the cells may be used as donors for bone marrow transplantation [Torok-Storb et al., *Bone Marrow Transplant.* 14: Suppl 4: S71–S73 (1994); Allay et al., *Blood* 88:645a (1996); PCT Application, US/96/17660, filed Nov. 4, 1996 designating the United States, entitled "In Vivo Selection of Primitive Hematopoietic Cells" having Sorrentino et al. as the Inventors, incorporated herein by reference in its entirety.] The mice are next subjected to antimetabolite treatment in the presence or absence of a nucleoside transport inhibitor (e.g., NBMPR or draflazine) over a period of about 10 or more days, and at the concentrations determined above. The in vivo enrichment of myeloid progenitors is assessed by comparing marrow cellularities between untreated control mice, transduced mice treated with the nucleoside transport inhibitor, and transduced mice not treated with nucleoside transport inhibitor.

In a related aspect, the present invention provides a method of overcoming a major limitation to successful hematopoietic cell-directed gene therapy. This major limitation is inefficient gene transfer into repopulating stem cells. The method is based on the selection of cells that express a desired heterologous gene due to linkage of the heterologous gene to a gene that encodes an iENTP.

Effective in vivo enrichment of transduced cells requires the elimination of unmodified hematopoietic cells. This can be effected by the administration of an antimetabolite such as trimetrexate (TMTX) in the presence of an es transporter inhibitor that preferentially inhibits the es transporter relative to the iENTP, (e.g., NBMPR). In the absence of expression of an iENTP, such a regimen has been shown to be toxic to hematopoietic progenitor cells both in vitro and in vivo [Allay et al., *Blood* 88: Supp.1, 645a (1996)]. In contrast, cells expressing iENTP can rely on the iENTP-dependent nucleoside salvage pathway in the presence of the inhibitors to de novo nucleoside synthesis and the es transporter-dependent nucleoside salvage pathway as described above. Therefore, linking the heterologous gene with the expression of the iENTP will ensure that surviving hematopoietic cells contain the desired heterologous gene when the cells are treated with drugs such as TMIX and NBMPR as described above.

Various therapeutic heterologous genes can also be inserted in a gene therapy vector of the invention such as but not limited to adenosine deaminase (ADA) to treat severe combined immunodeficiency (SCID); marker genes or lymphokine genes into tumor infiltrating (TIL) T cells [Kasis et al., *Proc. Natl. Acad. Sci. U.S.A.* 87:473 (1990); Culver et al., *ibid.* 88:3155 (1991)]; genes for clotting factors such as Factor VIII and Factor IX for treating hemophilia [Dwarki et al. *Proc. Natl. Acad. Sci. USA*, 92:1023–1027 (19950); Thompson, *Thromb. and Haemostatis*, 66:119–122 (1991)]; and various other well known therapeutic genes such as, but not limited to, β-globin, dystrophin, insulin, erythropoietin, growth hormone, glucocerebrosidase, β-glucuronidase, α-antitrypsin, phenylalanine hydroxylase, tyrosine hydroxylase, ornithine transcarbamylase, apolipoproteins, and the like. In general, see U.S. Pat. No. 5,399,346 to Anderson et al.

In another aspect, the present invention provides for regulated expression of the heterologous gene in concert with the expression of the iENTP. The present invention provides for co-expression of iENTP and a therapeutic heterologous gene under control of a specific DNA recognition sequence by providing a gene therapy expression vector comprising both a iENTP coding gene and a gene under control of, inter alia, the iENTP regulatory sequence. Concerted control of such heterologous genes may be particularly useful in the context of treatment for proliferative disorders, such as tumors and cancers, when the heterologous gene encodes a targeting marker or immunomodulatory cytokine that enhances targeting of the tumor cell by host immune system mechanisms. Examples of such heterologous genes for immunomodulatory (or immuno-effector) molecules include, but are not limited to, interferon-α, interferon-γ, interferon-β, interferon-ω, interferon-τ, tumor necrosis factor-α, tumor necrosis factor-β, interleukin-2, interleukin-7, interleukin-12, interleukin-15, B7-1 T cell co-stimulatory molecule, B7-2 T cell co-stimulatory molecule, immune cell adhesion molecule (ICAM) -1 T cell co-stimulatory molecule, granulocyte colony stimulatory factor, granulocyte-macrophage colony stimulatory factor, and combinations thereof.

The present invention may be better understood by reference to the following non-limiting Examples, which are provided as exemplary of the invention. These examples are presented in order to more fully illustrate the preferred embodiments of the invention. They should in no way be construed, however, as limiting the broad scope of the invention.

EXAMPLE 1

Molecular Cloning of the Equilibrative, Nitrobenzylmercaptopurineriboside (NBMPR)-Insensitive Nucleoside Transporter ei: a Delayed Early Response Gene

Introduction

Mammalian cells obtain nucleic acid precursors through the de novo synthesis of nucleotides and the salvage of exogenous nucleobases and nucleosides. The first step in the salvage of nucleosides is their transport across the plasma membrane. Several nucleoside transport activities, including both equilibrative and concentrative mechanisms, have been identified by their functional properties. Until recently, however, little has been known about the proteins that mediate these transport processes. Two of the concentrative transporters have now been cloned, and just recently the equilibrative NBMPR-sensitive transporter es was cloned (Griffiths et al, *Nature Med.* 3:89–93, 1997). The protein mediating equilibrative NBMPR-insensit ive t ransport (ei), however, has remained elusive. The cloning of a 2522 basepair (bp) cDNA from HeLa cells that encodes a functional ei transport protein is disclosed in this example. This cDNA was c loned by complementation of a defect in nucleoside transport in subline of CEM human leukemia cells. The cDNA encodes a 456-residue protein with 10 to 11 predicted membrane-spanning regions. Stable expression of this cDNA in nucleoside transport-deficient CEM cells, as well as transient expression in COS cells, conferred equilibrative, NBMPR-insensitive transport activity to the cells.

The predicted protein is highly homologous (50% identity, 69% similarity) to the recently cloned human NBMPR-sensitive equilibrative nucleoside transport hENT1, and thus has been designated hENT2. Surprisingly, the carboxy terminal portion of the predicted hENT2 protein is nearly identical to a 326 residue predicted peptide (hHNP36) in the Genbank database that has been identified as a growth factor-induced "delayed early response" gene of unknown function.

The transient transfection studies with full length hENT2 and a 5' truncated construct that lacks the first start codon (predicted protein 99% identical to hHP36) d emonstrated that a function al nucleoside transport protein is not produced from the second star codon. These data suggest that the hHNP36 protein is a truncated, non-functional form of hHP36. Since the hHNP36 cDNA was originally cloned as a delayed early response gene (der12), hHNT2 may be a delayed early response gene, and nucleoside transport may play an important role in the proliferative response when quiescent cells are stimulated into cycle by growth factors.

Materials and Methods

Cells and Growth Conditions. HeLa S3 cells and COS-1 cells from the American Type Culture Collection were grown at 37° C. in a humidified air and 5% $CO_2$ atmosphere in Dulbecco's Modified Eagle Medium (D-MEM). For HeLa S3 cells the medium was supplemented with 10% heat-inactivated fetal calf serum and for COS-1 cells with 5% heat-inactivated fetal calf serumplus 5% NuSerum IV (Collaborative Research Products). The CEM cell lines were grown as stationary suspension cultures at 37° C. in a humidified air and 5% $CO_2$ atmosphere in RPMI 1640 medium supplemented with 10% heat-inactivated horse serum and the following additions: CEM/AraC-8C, 0.25 μM tubercidin [4-amino-7-β-D-ribofuranosylpyrolo[2,3-d]pyrimidine]/0.5 μM AraC [1-β-D-arabinofuranosylcytosine]; CEM/C-19 cells, 0.25 μM tubercidin/0.5 μM AraC/50 μg/ml G418; N-1-7, 20 μM DUP-785 [6-fluoro-2(2'--fluoro-1, 1'-biphenyl-4-yl)-3-methyl-4-quinoline carboxylic acid sodium salt]/100 μM uridine [Dexter et al. Cancer Res. 45:5563 (1985)]. The nucleoside transport deficient cell line CEM/AraC-8C [Ullman et al.,*J. Biol. Chem.* 263:12391–12396 (1988)] was provided by Dr. Buddy Ullman, Oregon Health Sciences University, Portland Oreg. DUP-785 was provided by the National Cancer Institute.

Isolation of C-19 cells. A mixture containing CEM/AraC-8C cells ($2\times10^7$) and 10 μg of a plasmid mixture consisting of Sca 1-restricted pCMVEBNA (Clontech) and Sca 1-restricted pRSVneo at a 20:1 molar ratio was electroprated at 190 V at a capacitance of 960 μF utilizing a Gene Pulsar obtained from BioRad. After a 48 hour of recovery, the cells were selected in medium containing 200 μg/ml of G418 (Geneticin, obtained from Life Technologies) for 25 days. Surviving cells were cloned by plating in soft agarose (0.35%) containing 200 μg/ml G418. After 21 days colonies were transferred to liquid culture and grown for characterization.

Expression cloning. A Clontech HeLa S3 cell c-DNA library in the pDR2 vector was transfected into C-19 cells ($2 \times 10^8$) by electroporation as described above. In bulk culture, the electroporated cells were sequentially selected in medium containing 200 µg/ml hygromycin B (14 days), 20 µM DUP-785/100 µM uridine (27 days) and finally 20 µM DUP-785/100 µM uridine/1 µM NBMPR [(nitrobenzylmercaptopurineriboside), 6-[(4-nitrobenzyl)thio-9-β-D-ribofuranosyl purine] (14 days). Plasmids were extracted (utilizing a QIA-prep Spin Plasmid Miniprep Kit, Qiagen) from cells surviving selection and, subsequently used to transform electrocompetent WM 1100 *E. coli* cells (obtained from BioRad). Plasmids from individual *E. coli* colonies were analyzed by restriction digestion with BamH1 plus Xba1. Plasmids containing inserts were individually reintroduced into CEM/C19 cells which were then selected as before.

Sequencing of the pDR2/N171 insert. Both strands of the insert were sequenced to a level of 3 to 7-fold redundancy by Taq DyeDeoxy terminator cycle sequencing on an automated Model 373A DNA Sequencer, (obtained from Applied Biosystems). Northern analysis. PolyA+-RNA was isolated from the indicated cell lines using the FastTrack 2.0 kit from Invitrogen. The RNA (2 µg/lane) was separated on a formaldehyde reducing 1% agarose gel and transferred to charged nylon membranes (obtained from Hybond-N, Amersham Corp.). A BamHI/NheI cDNA fragment (1.8 kb) encompassing nucleotides 393–2183 was gel purified and labeled with $^{32}$P-dCTP using the Primelt kit from Strategene. Hybridization was carried out for 16 hours at 42° C. in 50% formamide containing 10% dextran sulfate. The blot was washed at high stringency (0.2× SSPE at 650° C.) and analyzed using a PhosphorImager and ImageQuant software. A multiple human tissue blot (obtained from Clontech) with 2 µg of polyA+ RNA/lane was also probed under identical conditions.

Transient Expression in COS-1 cells: The N1-71 clone contained a 1368 bp open reading frame with two potential start codons. The full orf plus the 3'-untranslated region were excised from pDR2/N1-71 in a BglI/XbaI fragment (233–2605) and directionally cloned into the multicloning site of pcDNA3 (Invitrogen) to give pcDNA3/N171orf1. Likewise, the second start site and 3'-untranslated region were excised in a BglII/XbaI fragment (bp 1104–2605) and ligated into pcDNA3 to give pcDNA3/N171orf2. These constructs were transfected into COS-1 cells by the DEAE-dextran method and uptake of uridine determined as described by Fang et al. [*Biochem. J.* 317:457465 (1996)].

Results

Cloning Strategy. Since an NBMPR-insensitive equilibrative nucleoside transport protein had not previously been identified, and there were no antibodies or affinity probes available, a cloning strategy based on the functional expression of ei transport activity in a nucleoside transport deficient cell line was devised. A nucleoside transport deficient subline of the human T-cell leukemia CEM [Ullman et al., *J. Biol.Chem.* 263:12391–12396 (1988)] was transfected with an EBNA-1 (Epstein-Barr Nuclear Antigen 1) expression cassette to produce a transport deficient cell line capable of supporting the episomal replication of the EBV-based mammalian expression vector pDR2. This cell line, designated CEM/C1 9, had a stable transfection frequency with pDR2 of approximately $10^{-2}$, which was four orders of magnitude greater than that of the parental EBNA-negative cell line. CEM/C19 cells were sensitive to the de novo uridylate synthesis inhibitor DUP-785, but could not be rescued from DUP-785 toxicity by uridine because of their transport defect. In contrast, transport competent CEM cells were readily rescued from DUP-785 toxicity by 100 µM uridine. CEM/C19 cells were transfected with a pDR2 human cDNA library from HeLa cells, which express es and ei transport activities [Dahlig-Harley et al., *Biochem J.* 200:295–305 (1981)] but do not have any detectable sodium-dependent nucleoside transport activity. Since CEM/C19 cells do not clone well in soft agar, batch cultures of transfected cells were subjected to sequential selection as follows: (1) hygromycin to select for transfected cells, (2) DUP-785 plus uridine to select for cells expressing any nucleoside transporter (all known transporters accept uridine as a permeant), and (3) DUP-785 plus uridine and NBMPR to select for cells expressing NBMPR-insensitive uridine transport activity. Surviving cell cultures were screened for NBMPR-insensitive uridine uptake, and plasmids extracted from positive cultures and rescued back into *E. coli*. Plasmids isolated from individual *E. coli* colonies were analyzed for the presence of inserts and reintroduced into CEM/C-19 cells. The cells were then selected for expression of NBMPR-insensitive uridine transport activity as before. A plasmid (pDR2/N1-7) containing a 2.6 Kb insert was identified that permitted cell survival upon reintroduction and selection. The cell line was designated CEM/N1-7 and used for further functional characterization of the plasmid.

Figure 1B:
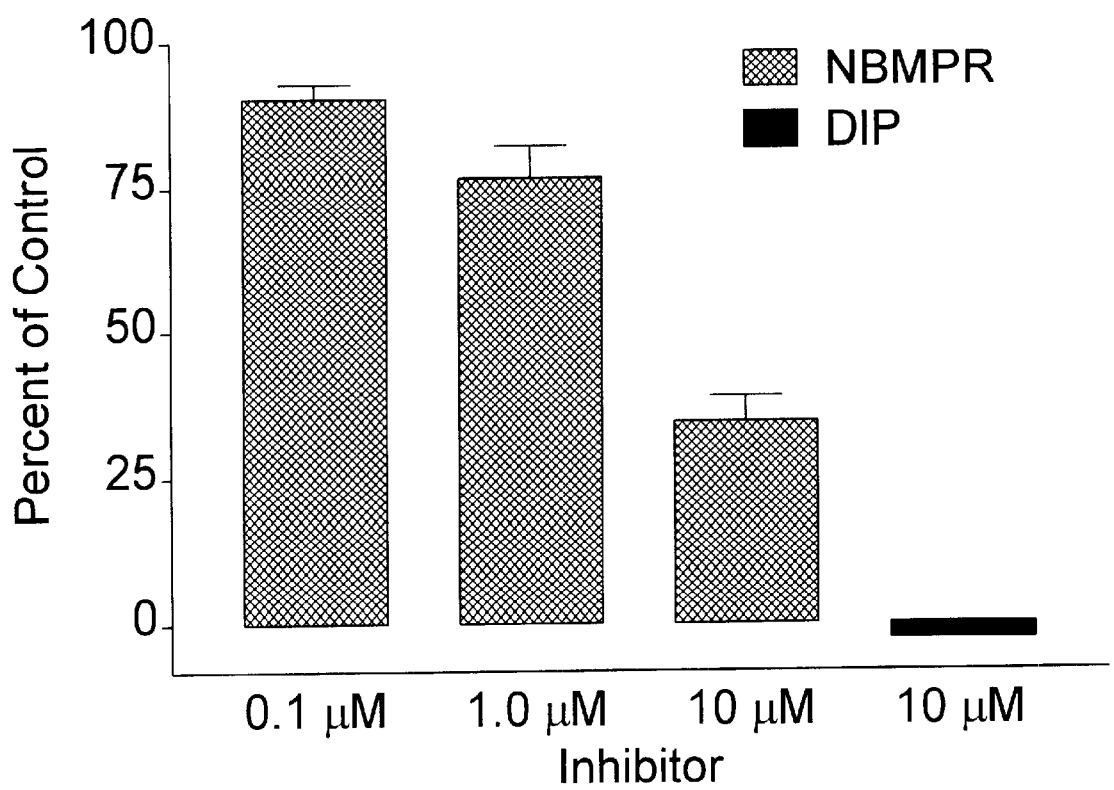
FIGS. 1B–1C depict the uptake of 10 $\mu$M $^3$H-uridine determined at 22° C. in Na$^+$buffer using a 7.5 second uptake interval in the presence of nucleoside transport inhibitors. The uptake interval was initiated by simultaneous addition of the label and inhibitory nucleobase, nucleoside or nucleotide. In the case of NBMPR and dipyridamole, the cells were incubated for 5 minutes at 22° C. in the appropriate concentration of inhibitor prior to starting the assay. Uridine uptake was also determined in the presence of a large excess (4 mM) of unlabeled uridine to determine the radioactivity associated with the extracellular water space and simple diffusion. This value was subtracted from the total uridine uptake values. The results are from triplicate. assays and are expressed as percent of uridine uptake in the absence of inhibitor.
Figure 1C:
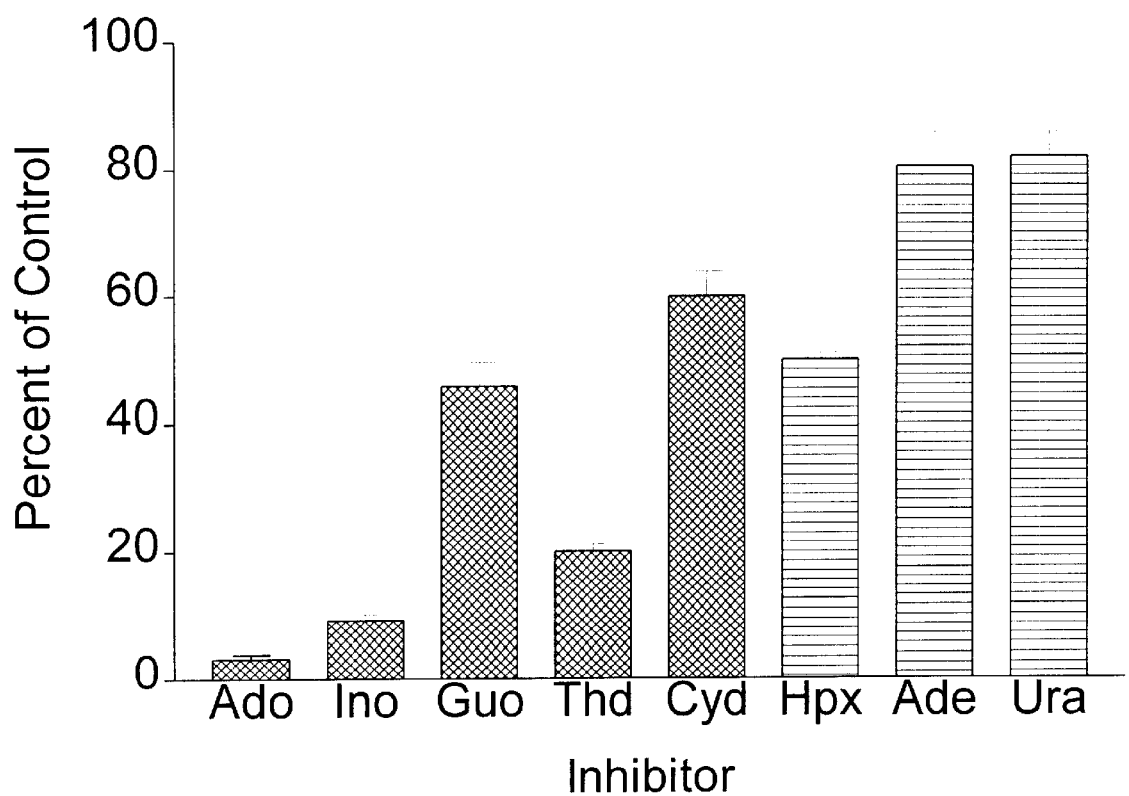

Uridine Transport in CEM/N1-7 Cells. To confirm the presence of uridine transport activity in the transfected cells, uridine influx was compared in CEM/N1-7 and CEM/C19 cells (FIG. 1A). CEM/N1-7 cells displayed a large component of uridine influx that was at least 10-fold greater than that of the CEM/C19 cells. Addition of a large excess of unlabeled uridine blocked uridine transport in the transfected cells, indicating the presence of a saturable carrier mediated process; but had no effect on uridine uptake in CEM/C19 cells, suggesting that the slow rate of uptake was due to simple diffusion. Removal of sodium from the buffer had no effect on transport in CEM/N1-7 indicating the presence of an equilibrative type transporter. Addition of NBMPR at a concentration of 0.1 µM, which is sufficient to block es mediated transport, had no effect on transport in CEM/N1-7 cells (FIG. 1B) suggesting that the cDNA insert encoded the NBMPR-insensitive equilibrative nucleoside transporter ei. Partial inhibition of transport at higher concentrations of NBMPR (FIG. 1B) was also consistent with the described properties of the human ei transporter in HeLa cells where the $IC_{50}$ values (concentration producing a 50% inhibition) for inhibition of uridine transport via es and ei are 1 nM and 6 µM, respectively [Dahlig-Harley et al., (1981), supra]. Also consistent with the ei transporter of HeLa cells [Dahlig-Harley et al., (1981), supra], transport in CEM/N1-7 cells was completely blocked by 10 µM DIP [dipyridamole, or bis(diethanolamino)-4,8-dipiperidinopyrimido-[5,4-d]-2,6-pyrimidine] (FIG. 1B). As expected from the permeant selectivity observed for ei activity in several cell lines [Plagemann et al., *Biochim. Biophys. Acta*, 947:405–444; Cass, Nucleoside Transport in N. H. Gergopapadakou (ed.), Drug Transport in Antimicrobial Therapy and Anticancer Therapy, pp. 403–451, New York: Marcel Dekker (1995); Griffeth and Jarvis, 1996, supra], uridine influx in CEM/N1-7 cells was inhibited by both purine and pyrimidine nucleosides (FIG. 1C), but not by the corresponding nucleotides. Interestingly, uridine transport in CEM/N1-7 cells was inhibited by the nucleobase hypoxanthine, but not by the other nucleobases tested (FIG. 1C). While ei activity is generally considered a nucleoside transporter, previous studies have suggested that it may also transport hypoxanthine (reviewed in [Griffith and Jarvis, 1996, supra]). This was recently confirmed by Jarvis and colleagues [Osses et al.,

*Biochem. J.*, 317:843–848 (1996)] by direct measurements of hypoxanthine in human vascular endothelial cells. In summary, the uridine transport activity demonstrated in CEM/N1-7 cells was $Na^+$-independent, inhibited by physiological nucleosides, such as hypoxanthine and dipyridamole, but relatively insensitive to inhibition by NBMPR. All these features are consistent with those of an ei transporter, ie., an iENTP.

Rescue and analysis of the plasmid. Plasmids were extracted from CEM/N1-7 cells and rescued back into *E. coli*. Restriction analysis of the plasmids from individual *E. coli* colonies demonstrated the presence of a single plasmid containing a 2.6 Kb insert which appeared to be identical to the plasmid initially introduced into CEM/C19 cells to create the CEM/N1-7 cell line. The insert from one of the recovered cloned plasmids (designated N1-71) was sequenced. The N1-71 cDNA was 2522 basepairs and contained a 1368 basepair open reading frame that encodes a 456 residue protein with 10 to 11 predicted membrane spanning regions (FIG. 2).

The N1-71 protein exhibits 50% identity (69% similarity) to the recently cloned human NBMPR sensitive nucleoside transport protein hENT1, FIG. 2 [Griffiths et al. *Nature Med*. 3:89–93 (1997)], and thus has been designated hENT2, as a member of this family of proteins. As noted previously members of this family can also be found in yeast and nematodes [Griffiths et al. (1997), supra]. Analysis of the aligned sequences shown in FIG. 2 predict 10 transmembrane domains for this family of proteins, although analysis of either hENT1 [Griffiths et al. (1997), supra] or hENT2 alone predict 11 transmembrane domains. As seen with other membrane transporter families, the most highly conserved regions of the ENT proteins fall in the transmembrane domains. All members of the family have an extracellular loop, with an N-glycosylation site between transmembrane domains 1 and 2 in nine of the ten reported family members. The length of the extracellular loop is variable, and there is very little conservation of sequence within the loop except for the N-glycosylation site.

Figure 3:
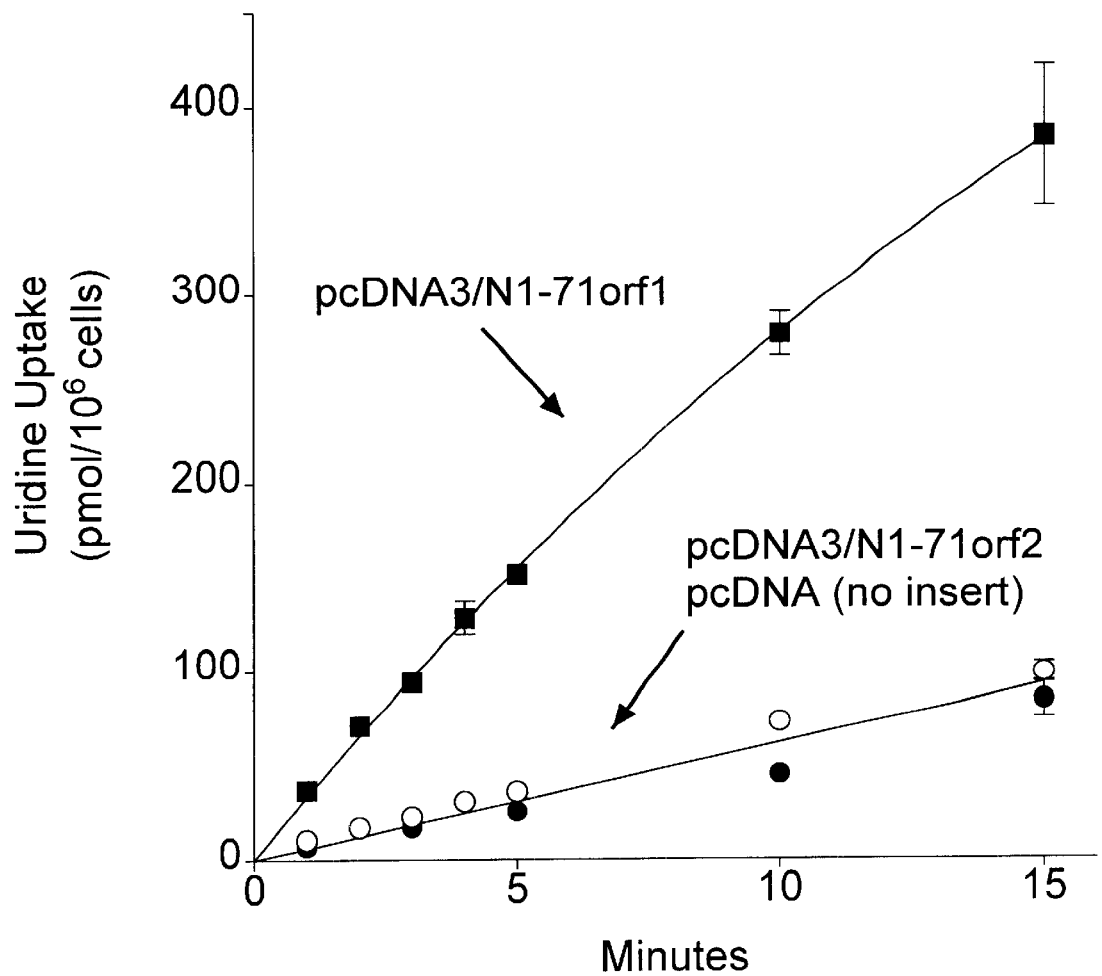
FIG. 3 shows uridine uptake by COS-1 cells transiently transfected with pcDNA3/N1-71 constructs. COS-1 cells were transfected with pcDNA3/N1-71orf1 (■) or cDNA3/N1-71orf2 (○) as described in the methods. Control cells (•) were transfected with the pcDNA3 plasmid without an insert. Uptake of 10 $\mu$M $^3$H-uridine (2 $\mu$Ci/ml) was determined in sodium-free buffer 72 hours after transfection. 0.1 $\mu$M NBMPR was present in all assays to block the endogenous es transporter in COS-1 cells {4539}. The values shown are the average of triplicate determination.

Surprisingly, the carboxy terminal portion of the predicted hENT2 protein is also nearly identical to a 326 amino acid residue predicted peptide (hHNP36) in the Genbank database that has been identified as a growth factor-induced "delayed early response" gene of unknown function [Williams et al., *Biochem. Biophys. Res. Comm.*, 213:325–333 (1995)]. Inspection of the hHNP36 nucleotide sequence revealed two potential open reading frames with hHNP36 translated from the second start codon. While hENT2 also has two potential start codons, they are within the same open reading frame. The full length cDNA of hHNP36 (2281 bp) is nearly identical to hENT2, but contains a 68 bp deletion beginning at position 338. This deletion shifts initial reading frames relative to hENT2 and would result in a truncated 22 Kd protein with only 51% identity to the hENT2 protein. Transient transfection studies with full length hENT2 and a 5'-truncated construct that lacks the first start codon (predicted protein 99% identical to hHNP36 (FIG. 3)) demonstrated that a functional nucleoside transport protein is not produced from the second start codon. These data suggest that the hHNP36 protein is a truncated, non-functional form of hENT2.

Figure 4A:
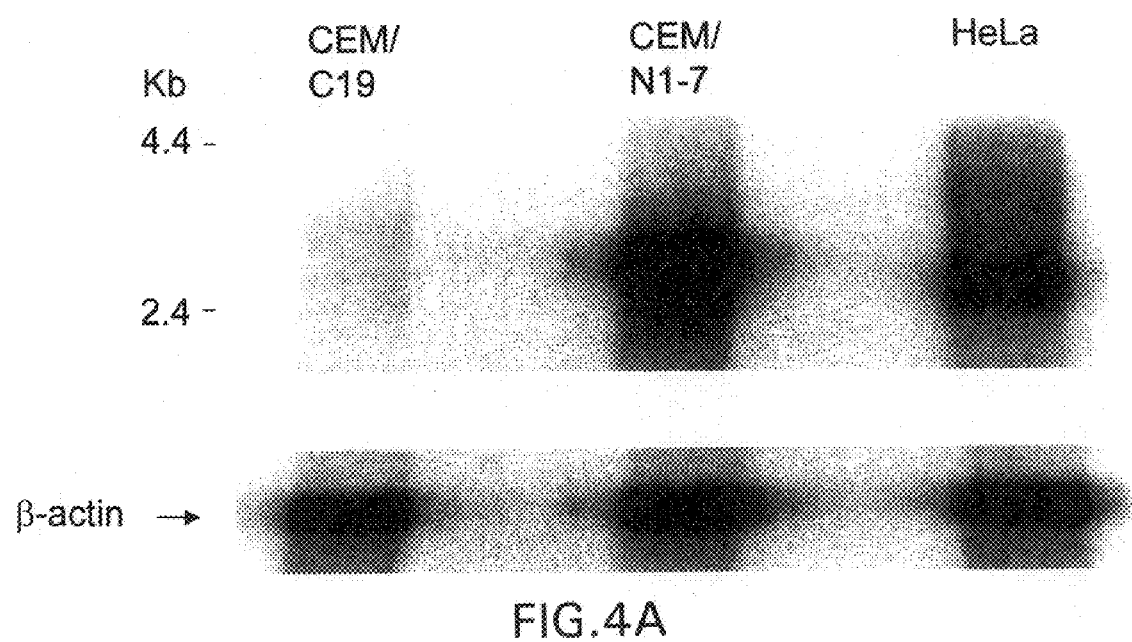
FIG. 4 demonstrates the expression of hENT2 in human cell lines and tissues. Northern blots of polyA+RNA from the indicated cell lines (FIG. 4A) and tissues (FIG. 4B) were hybridized with a BamHI/NheI fragment of hENT2 (1.8 kb, nucleotides 393–2183 of SEQ ID NO:1) and washed at high stringency as described in the methods.

Expression of hENT2 in human cell lines and tissues. Northern blots of polyA+ RNA from HeLa, parental CEM cells, the transport deficient recipient cell line CEM/C19, and the stable transfectant CEM/N1-7 were probed at high stringency using a $^{32}P$ labeled BamHI/NheI fragment of N1-71 that encompasses 90% of the coding region of hENT2. As shown in FIG. 4A, a single transcript of approximately 2.6 Kb was identified in HeLa cells, the cell line from which the cDNA library was derived. A slightly larger transcript (approximately 3.0 Kb) was observed in the stable transfectant CEM/N1-7. The larger size of the message in CEM/N1-7 cells can be accounted for by the fact that in these cells the message is derived from transcriptional start and termination sites of the pDR2 vector, which adds approximately 460 nucleotides to the insert. These data indicate that N1-71 represents the full length cDNA for the ei transporter. As shown in FIG. 4A, no message was detected in the transport deficient recipient cell line CEM/C19.

Figure 4B:
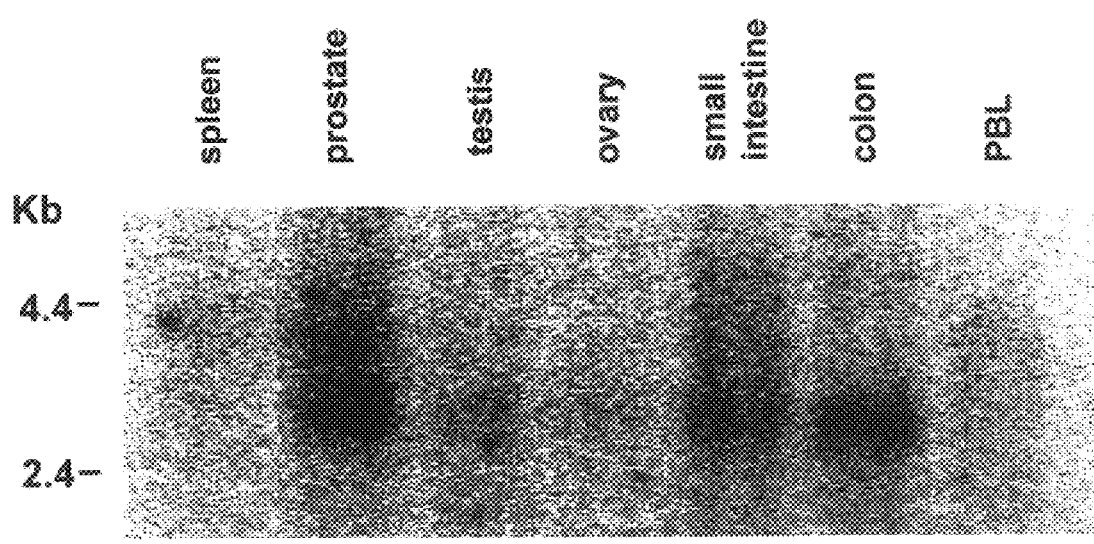

The tissue distribution of the ei transporter was examined using human multiple tissue blots from CLONTECH (FIG. 4B). As expected from previous functional studies of ei transport activity in cultured cell lines, ENT2 was found to be expressed in a number of tissues, and the level of expression was variable among tissues. A message of about 2.6 kbp was detected in most tissues, but a larger transcript (=4 kbp) was also observed in thymus, prostate, heart, brain, lung, skeletal muscle, and pancreas. The highest level of ENT2 expression was in skeletal muscle, with the 2.6-kbp message predominating. The high level of expression in skeletal muscle was unexpected, as this tissue is composed of nondividing, terminally differentiated cells. It is possible, however, that the ENT2 transporter plays a role in the efflux of inosine and hypoxanthine from muscle cells during the net degradation of purine nucleotides that occurs during strenuous exercise and/or in the re-uptake of these purines during the recovery process [Arabadjis et al., *Am. J. Physiol.*, 264: C1246–C1251 (1993); Norman et al., *Clin. Physiol.*, 7:503–510 (1987)].

EXAMPLE 2

Protection of Hematopoietic Stem Cells with a cDNA Encoding a NBMPR-insensitive Equilibrative Nucleoside Transport (iENTP) for use in Chemotherapy Introduction Antimetabolites such as trimetrexate, methotrexate, PALA and 5-fluorouracil are commonly used in the clinical treatment neoplastic disorders, including cancers. These drugs were designed to block de novo nucleotide synthesis, and thereby prevent the proliferation of the otherwise rapidly replicating tumor cells. One common problem associated with such treatments arises when the targeted tumor cells circumvent the cytotoxic effects of the de novo synthesis inhibitor by acquiring purine and pyrimidine nucleosides from exogenous pools through a nucleoside salvage pathway. In fact, tumor cells commonly express significant levels of nucleoside transporters.

Furthermore, nucleoside analogs such as cytosine arabinoside (Ara-C), 2-Chloro-2'-deoxyadenosine, AZT, and ddI are commonly used to treat viral and neoplastic disorders including AIDS and cancers. Nucleoside transporters are involved in the uptake and efflux of these drugs by cells. Thus the administration of NBMPR following the cytotoxic nucleoside may enhance the activity of these drugs by blocking their exit from the cell and prolonging the exposure of the cellular targets to the drug and its active metabolites. The major form of nucleoside transport seen in 9/9 leukemia, 4/4 rhabdomyosarcoma and 4/4 colon carcinoma cell lines is performed by an NBMPR-sensitive, equilibrative (es) transporter [Belt et al. *Advan. Enzyme Regul.*, 33:235–252 (1993)]. Therefore, supplementing the antimetabolite regimen with NBMPR serves to potentiate the desired cytotoxic effects in the tumor cells. Unfortunately, the es transporter is also the major nucleoside transporter in normal bone marrow cells [Belt et al. *Advan. Enzyme Regul.*, 33:235–252 (1993)], and thus administering NBMPR with the antimetabolites also potentiates an undesired cytotoxic effect in normal myeloid progenitors in bone marrow cells. Described herein, is a method of clinically treating viral and neoplastic disorders, including cancers and AIDS, which allows for the potentiation of the desired cytotoxic effects of antimetabolites in tumor cells by co-administering NBMPR, which also protects the hematopoietic stem cells from the undesired cytotoxic effects of such treatment.

Materials and Methods

Treatment of normal myeloid progenitor cells with antimetabolites to determine resistance. Normal mice are treated by intraperitoneal administration with varying doses of methotrexate (MTX; 20 mg/kg–200 mg/kg) for five consecutive days, to determine cytotoxic effects on normal myeloid progenitor cells and hematopoietic stem cells with this antimetabolite. Other nucleoside antimetabolites such as trimetrexate, PALA, 5-fluorouracil, AraC, and AZT, are similarly tested (as required) at clinically relevant dosages. The marrow from drug treated and untreated mice are examined for myeloid progenitor cell numbers to determine the degree of cytotoxic effects.

The use of NBMPR or draflazine to potentiate the activity of antimetabolite in vitro. NBMPR (0.1 μM to 10 μM) and/or draflazine (0.1 μM to 10 μM) are added in conjunction with (or directly before or after) an antimetabolite to murine bone marrow cells in an in vitro culture system optimized using medium supplemented with hematopoietic growth factors (IL-3 at 20 ng/ml, human IL-6 at 50 ng/ml, rat SCF at 50 ng/ml) and fetal bovine serum. The concentration of antimetabolite used is that found to be cytotoxic in the above study. The effect of NBMPR or draflazine on potentiating the activity of the antimetabolites are assessed by cell count measurements over a 24 hour period after treatment.

In vivo selection of myeloid progenitor cells using hENT2 cDNA. Hematopoietic stem cells are transduced with either viral constructs (retrovirus, adeno-associated virus or lenti virus) containing a nucleic acid encoding an iENTP (e.g., hENT2) or a control nucleic acid (e.g., encoding MDR1). Mice are then transplanted with either hENT2 or MDR1 transduced cells e.g., the cells may be used as donors for bone marrow transplantation [Torok-Storb et al., *Bone Marrow Transplant.* 14: Suppl 4: S71–S73 (1994); Allay et al, *Blood* 88:645a (1996); PCT Application, US/96/17660, filed Nov. 4, 1996 designating the United States, entitled "In Vivo Selection of Primitive Hematopoietic Cells" having Sorrentino et al. as the Inventors, incorporated herein by reference in its entirety]. The mice are next subjected to antimetabolite treatment in the presence of a nucleoside transport inhibitor (the antimetabolite and the nucleoside transport inhibitor also may be administered separately) or in the absence of a nucleoside transport inhibitor, e.g., NBMPR or draflazine, over a period of about 10 days or more, and at the concentrations determined above. The in vivo enrichment of myeloid progenitors is assessed by comparing marrow cellularities between untreated control mice, transduced mice treated with the nucleoside transport inhibitor, and transduced mice not treated with nucleoside transporter inhibitor.

Results

The solution presented herein relies on the transduction of normal hematopoietic stem cells ex vivo with a cDNA encoding an iENTP. Such a transduced cell when transplanted expresses iENTP in vivo and is thereby protected from the antimetabolite/NBMPR treatment by the iENTP-dependent nucleoside salvage pathway. In contrast, untransduced cells and tumor cells which do not express zENTP are selected against, due to the blockage of both their de novo nucleoside biosynthesis and their NBMPR-sensitive nucleoside salvage pathway by the nucleoside antimetabolite/NBMPR treatment. In the case of the nucleoside analogs, the transduced hematopoietic stem cells are protected by the efflux of the nucleoside analogs, via the iENTP-dependent transport pathway. Untransduced cells and tumor cells are selected against due to the retention of the nucleoside analog and its active metabolites in the cells when the NBMPR-sensitive transport pathway is blocked by NBMPR.

The dosage of NBMPR to be administered is empirically determined by studies in a murine models first, as described Materials and Methods, and subsequently in higher mammals and humans. The use of a nucleoside transporter to provide protection in hematopoietic stem cells provides for the use of any antimetabolite, and in particular, methotrexate, trimetrexate, PALA, 2CDA, ddC, and 5-fluorouracil which have already been used in the clinic for the treatment of neoplastic and viral disorders.

Figure 5:
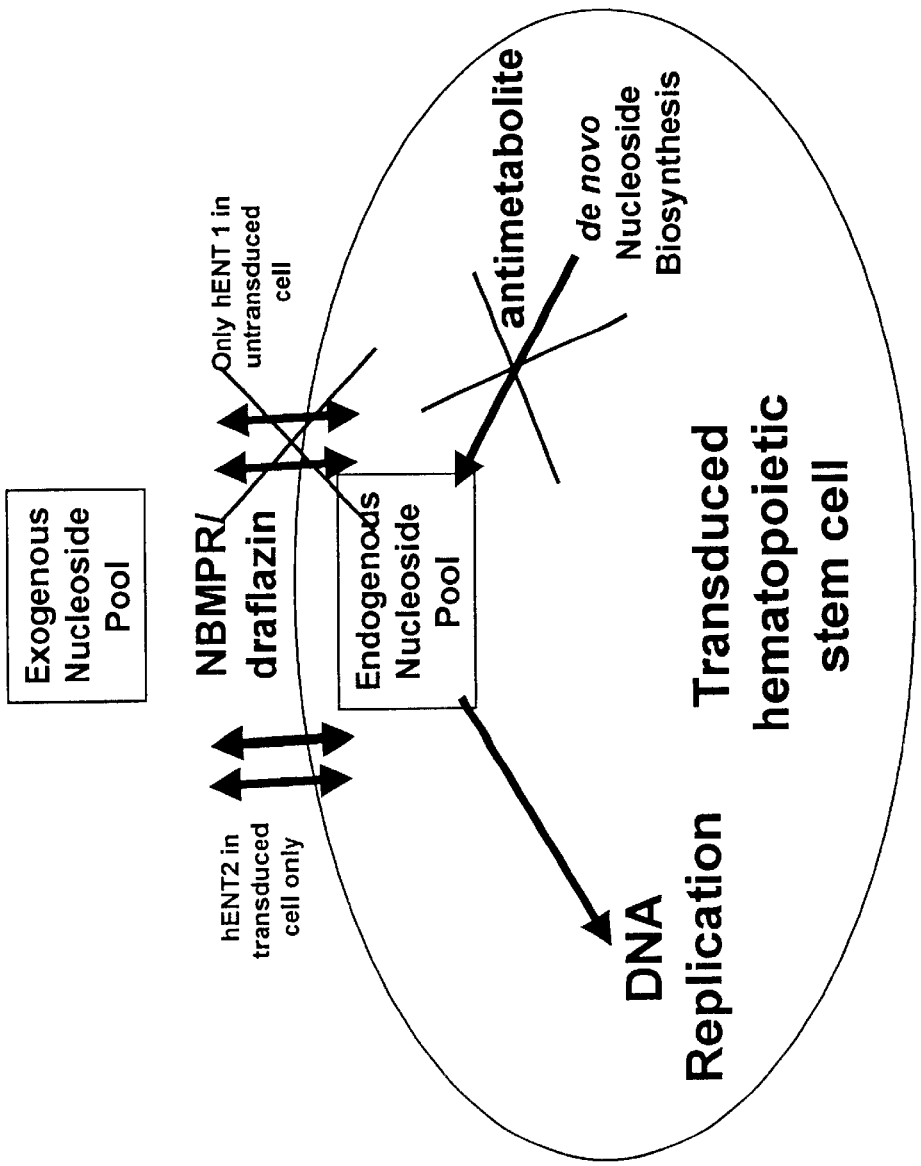
FIG. 5 is a schematic drawing showing the results of challenging CD34 positive hematopoietic stem cells with an antimetabolite and a nucleoside transport inhibitor, after the cells have been transduced, ex vivo, with a viral vector comprising a nucleic acid encoding hENT2. The antimetabolite (e.g., methotrexate, trimetrexate, 5-FU or PALA) plus the nucleoside transport inhibitor NBMPR or draflazine are administered to the cells thereby selectively enriching for cells that have been successfully transduced with hENT2. The enrichment is achieved because the antimetabolite prevents de novo synthesis of the nucleosides required for cell growth, and the transduced cells are uniquely resistant to NBMPR and draflazine and thereby retaining a functional salvage pathway for purine and pyrimidine nucleosides present in exogenous nucleoside pools. Although not shown, the ex vivo transduced cells may be transplanted into the animal subject and the antimetabolite and nucleoside transport inhibitor may be administered parenterally.

FIG. 5 is a schematic depicting the in vivo results following the ex vivo transduction of normal CD34 positive hematopoietic stem cells with viral vectors containing a nucleic acid encoding hENT2. Re-transplantation of the transduced cells is followed by intraperitoneally administering an antimetabolite (MTX, trimetrexate, 5-FU or PALA) together with a nucleoside transport inhibitor (e.g., NBMPR or draflazine). The combination of the antimetabolite and the nucleoside transport inhibitor selectively enriches for the hENT2 transduced cells which are resistant to both NBMPR and draflazine. These transduced cells are thereby protected from the antimetabolite/NBMPR regimen by the NBMPR-insensitive hENT2-dependent nucleoside salvage pathway which transports purine and pyrimidine nucleosides from exogenous pools through the plasma membrane.

EXAMPLE 3

Isolation of a BAC Containing the iENTP Gene

An iENTP cDNA was used to screen a BAC library (Genome Systems, Inc.). Of the three clones identified, one clone contained both the 5' and 3'-UTR (SEQ ID NO:5 and SEQ ID NO:10) as determined by Southern Analysis and PCR.

PCR sequencing of the BAC using iENTP primers identified 11 introns from the 5' UTR to 3' UTR nucleic acid. A BAC-specific primer for iENTP was used to identify a 2.4 kilobase sequence 5 prime to the cDNA (SEQ ID NO:6). In all, the iENTP gene was found to have at least 11 kilobases with 12 exons and 11 introns (FIG. 6).

EXAMPLE 4

Alternative Splice Sites

An alternative splice variant was identified in Thymus cells. A nucleic acid was identified having the nucleotide sequence of SEQ ID NO:9. A nucleotide sequence of SEQ ID NO:7 was then deduced which has the amino acid sequence of SEQ ID NO:8. A schematic drawing of the alternatively spliced nucleic acid is shown in FIG. 7. The identification of this alternative splice site indicates that there is tissue specific regulation of iENTP expression with alternative splicing.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

It is firther to be understood that all base sizes or amino acid sizes, and all molecular weight or molecular mass values, given for nucleic acids or polypeptides are approximate, and are provided for description.

Various publications, patent applications and patents are cited herein, the disclosures of which are incorporated by reference in their entireties.

What is claimed is:

1. An isolated nitrobenzylmercaptopurineriboside (NBMPR) insensitive, equilibrative nucleoside transport protein (iENTP) or active fragment thereof, wherein the iENTP:
   (a) functions as an equilibrative nucleoside transport protein; and
   (b) is insensitive to NBMPR; and wherein the iENTP comprises an amino acid sequence selected from the group consisting of SEQ ID NO:2 and SEQ ID NO:2 comprising a conservative amino acid substitution.

2. An isolated nitrobenzylmercaptopurineriboside (NBMPR) insensitive, equilibrative nucleoside transport protein (iENTP) having an amino acid sequence encoded by a nucleotide sequence with at least 80% identity with the coding sequence of SEQ ID NO:1; wherein said iENTP:
   (a) functions as an equilibrative nucleoside transport protein;
   (b) is insensitive to nitrobenzylmercaptopurineriboside (NBMPR); and
   (c) is a protein containing approximately 450 amino acid residues.

3. A fusion protein comprising a nitrobenzylmercaptopurineriboside (NBMPR) insensitive, equilibrative nucleoside transport protein (iENTP) or active fragment thereof, wherein the iENTP:
   (a) functions as an equilibrative nucleoside transport protein; and
   (b) is insensitive to NBMPR; and wherein the iENTP comprises an amino acid sequence selected from the group consisting of SEQ ID NO:2 and SEQ ID NO:2 comprising a conservative amino acid substitution.

* * * * *

UNITED STATES PATENT AND TRADEMARK OFFICE
CERTIFICATE OF CORRECTION

PATENT NO. : 6,423,829 B1  Page 1 of 1
DATED : July 23, 2002
INVENTOR(S) : Belt, Judith A., Crawford, Charles R. and Patel, Divyen H.

It is certified that error appears in the above-identified patent and that said Letters Patent is hereby corrected as shown below:

<u>Title page,</u>
Item [75], delete "Patel, Divyen H." as an inventor. Inventors are -- Belt, Judith A.; Crawford, Charles R. --

Signed and Sealed this

Twenty-sixth Day of November, 2002

Attest:

Attesting Officer

JAMES E. ROGAN
*Director of the United States Patent and Trademark Office*